US012758645B2

(12) United States Patent
Lelieveldt et al.

(10) Patent No.: US 12,758,645 B2
(45) Date of Patent: Oct. 13, 2026

(54) ANTIBODY-CONJUGATES FOR TARGETING OF TUMOURS EXPRESSING CARCINOEMBYRONIC ANTIGEN

(71) Applicant: Synaffix B.V., Oss (NL)

(72) Inventors: Lianne Lelieveldt, Nijmegen (NL); Remon van Geel, Lithoijen (NL); Sander Sebastiaan van Berkel, Oss (NL); Floris Louis van Delft, Nijmegen (NL)

(73) Assignee: Synaffix B.V., Oss (NL)

( * ) Notice: Subject to any disclaimer, the term of this patent is extended or adjusted under 35 U.S.C. 154(b) by 0 days.

(21) Appl. No.: 18/892,256

(22) Filed: Sep. 20, 2024

(65) Prior Publication Data

US 2025/0082770 A1 Mar. 13, 2025

Related U.S. Application Data

(63) Continuation of application No. PCT/EP2023/057565, filed on Mar. 23, 2023.

(30) Foreign Application Priority Data

Mar. 23, 2022 (EP) .................................... 22163928

(51) Int. Cl.
*A61K 47/68* (2017.01)
*A61P 35/00* (2006.01)
*C07K 16/30* (2006.01)

(52) U.S. Cl.
CPC .... *A61K 47/68037* (2023.08); *A61K 47/6853* (2017.08); *A61K 47/6889* (2017.08); *A61P 35/00* (2018.01); *C07K 16/3007* (2013.01)

(58) Field of Classification Search
None
See application file for complete search history.

(56) References Cited

U.S. PATENT DOCUMENTS 5,872,215 A 2/1999 Osbourne et al.
5,874,540 A 2/1999 Hansen et al.
5,876,691 A 3/1999 Chester et al.
6,676,924 B2 * 1/2004 Hansen .............. A61K 47/6853 424/1.49
7,232,888 B2 6/2007 Begent et al.
7,238,785 B2 7/2007 Govindan et al.
7,776,330 B2 8/2010 Yazaki et al.
7,803,372 B2 9/2010 Goldenberg et al.
8,394,926 B2 3/2013 Mayer et al.
8,642,742 B2 2/2014 Hofer et al.
8,715,662 B2 5/2014 Alberti
8,778,342 B2 7/2014 Goldenberg et al.
8,871,908 B2 10/2014 Liu et al.
9,068,008 B2 6/2015 Hofer
9,102,738 B2 8/2015 Terrett et al.
9,427,464 B2 8/2016 Nakamura et al.
9,505,845 B2 11/2016 Terrett et al.
9,617,345 B2 4/2017 Berne et al.
9,695,250 B2 7/2017 Fluhr et al.
9,777,070 B2 10/2017 Damelin et al.
9,850,312 B2 12/2017 Agatsuma et al.
10,179,171 B2 1/2019 Govindan et al.
10,457,739 B2 10/2019 Berne et al.
11,008,398 B2 5/2021 Agatsuma et al.
11,192,954 B2 12/2021 Tang et al.
11,338,043 B2 5/2022 Van Berkel et al.
12,397,063 B2 8/2025 Wijdeven et al.
12,440,573 B2 10/2025 Lelieveldt et al.
2004/0001825 A1 1/2004 Govindan et al.
2005/0147614 A1 7/2005 Begent et al.
2007/0212350 A1 9/2007 Govindan et al.
2008/0131363 A1 6/2008 Govindan et al.
2013/0344509 A1 12/2013 Nakamura et al.
2015/0125386 A1 * 5/2015 Hansen .............. A61K 51/1048 424/1.49
2015/0315196 A1 * 11/2015 Howard .................. A61P 35/02 540/496
2016/0297890 A1 10/2016 Agatsuma et al.
2018/0200273 A1 7/2018 Nguyen et al.
2019/0153071 A1 5/2019 Klein et al.
2020/0140815 A1 5/2020 Terrett et al.
2021/0393792 A1 12/2021 Wijdeven et al.
2023/0330245 A1 10/2023 Hoogenboom et al.
2025/0090679 A1 3/2025 Wijdeven et al.
2025/0099601 A1 3/2025 Lelieveldt et al.

(Continued)

FOREIGN PATENT DOCUMENTS

CN 107735090 A 2/2018
CN 107735104 A 2/2018
CN 113710277 A 11/2021

(Continued)

OTHER PUBLICATIONS

Lloyd et al. Protein Engineering, Design & Selection 22: 159-168 (Year: 2009).*
Edwards et al., J Mol Biol. 334(1): 103-118 (Year: 2003).*
Poosarla et al., Biotechn. Bioeng., 114(6): 1331-1342 (Year: 2017).*
Tong et al., Molecules 26: 5847 (Year: 2021).*
PCT/EP2023/057565, Mar. 23, 2023, Lianne Lelieveldt et al.
Geel et al., "Chemoenzymatic Conjugation of Toxic Payloads to the Globally Conserved N-Glycan of Native mAbs Provides Homogeneous and Highly Efficacious Antibody-Drug Conjugates", Bioconjugate Chemistry. 2015, 26(11): 2233-2242.
Ashraf et al., "Humanised IgG1 antibody variants targeting membrane-bound carcinoembryonic antigen by antibody-dependent cellular cytotoxicity and phagocytosis", British Journal of Cancer, Nature Publishing Group UK, London. 2009. 101(10): 1758-1768,.

(Continued)

*Primary Examiner* — Phuong Huynh
(74) *Attorney, Agent, or Firm* — COOLEY LLP; John P. Rearick; Todd K. Macklin

(57) ABSTRACT

The present invention provides antibody-conjugates for targeting CEA-expressing cells, in particular tumor cells. The invention further provides methods for preparing the antibody-conjugates, compositions thereof, and methods of using the same.

7 Claims, 15 Drawing Sheets

Specification includes a Sequence Listing.

(56) References Cited

U.S. PATENT DOCUMENTS

2025/0205353 A1 6/2025 Lelieveldt et al.

FOREIGN PATENT DOCUMENTS

| | | | |
|---|---|---|---|
| CN | 113816969 A | 12/2021 | |
| EP | 0296597 A2 | 12/1988 | |
| EP | 0721470 A1 | 7/1996 | |
| EP | 2922875 B1 | 3/2017 | |
| EP | 2911699 B1 | 11/2017 | |
| EP | 3088419 B1 | 10/2018 | |
| EP | 3483183 B1 | 4/2021 | |
| NL | 2026947 B1 | 7/2022 | |
| WO | WO-1995006067 A1 | 3/1995 | |
| WO | WO-1997014796 A1 | 4/1997 | |
| WO | WO-1997020932 A1 | 6/1997 | |
| WO | WO-2003074566 A2 | 9/2003 | |
| WO | WO-2004032857 A2 | 4/2004 | |
| WO | WO-2007071426 A1 | 6/2007 | |
| WO | WO-2007095506 A1 | 8/2007 | |
| WO | WO-2007095748 A1 | 8/2007 | |
| WO | WO-2007095749 A1 | 8/2007 | |
| WO | WO-2008144891 A1 | 12/2008 | |
| WO | WO-2009073546 A2 | 6/2009 | |
| WO | WO-2009102820 A2 | 8/2009 | |
| WO | WO-2011136645 A1 | 11/2011 | |
| WO | WO-2011155579 A1 | 12/2011 | |
| WO | WO-2012040824 A1 | 4/2012 | |
| WO | WO-2013068946 A2 | 5/2013 | |
| WO | WO-2013077458 A1 | 5/2013 | |
| WO | WO-2014065661 A1 | 5/2014 | |
| WO | WO-2015012904 A2 | 1/2015 | |
| WO | WO-2015069430 A2 | 5/2015 | |
| WO | WO-2015098099 A1 | 7/2015 | |
| WO | WO-2015168019 A2 | 11/2015 | |
| WO | WO-2016022027 A1 | 2/2016 | |
| WO | WO-2016053107 A1 | 4/2016 | |
| WO | WO-2016150899 A2 | 9/2016 | |
| WO | WO-2016170186 A1 | 10/2016 | |
| WO | WO-2017004144 A1 | 1/2017 | |
| WO | WO-2017137456 A1 | 8/2017 | |
| WO | WO-2017137457 A1 * | 8/2017 | ............. A61K 38/07 |
| WO | WO-2017137458 A1 | 8/2017 | |
| WO | WO-2017137459 A1 | 8/2017 | |
| WO | WO-2018126092 A1 | 7/2018 | |
| WO | WO-2019065964 A1 | 4/2019 | |
| WO | WO-2019110725 A1 | 6/2019 | |
| WO | WO-2019236954 A1 | 12/2019 | |
| WO | WO-2020094670 A1 | 5/2020 | |
| WO | WO-2020200880 A1 | 10/2020 | |
| WO | WO-2020219287 A1 | 10/2020 | |
| WO | WO-2021015622 A1 | 1/2021 | |
| WO | WO-2021053587 A1 | 3/2021 | |
| WO | WO-2021144313 A1 | 7/2021 | |
| WO | WO-2021144314 A1 | 7/2021 | |
| WO | WO-2021214221 A1 | 10/2021 | |
| WO | WO-2021214222 A1 | 10/2021 | |
| WO | WO-2021214223 A1 | 10/2021 | |
| WO | WO-2021214227 A1 | 10/2021 | |
| WO | WO-2021248048 A2 | 12/2021 | |
| WO | WO-2022049211 A1 | 3/2022 | |
| WO | WO-2022058395 A1 | 3/2022 | |
| WO | WO-2022242681 A1 | 11/2022 | |
| WO | WO-2023079057 A1 | 5/2023 | |
| WO | WO-2023099682 A1 | 6/2023 | |
| WO | WO-2023180484 A1 | 9/2023 | |
| WO | WO-2023180485 A1 | 9/2023 | |
| WO | WO-2023180489 A1 | 9/2023 | |

OTHER PUBLICATIONS

Verkade et al., "A Polar Sulfamide Spacer Significantly Enhances the Manufacturability, Stability, and Therapeutic Index of Antibody-Drug Conjugates", Antibodies. 2018, 7(1): 12.

Dotan Efrat et al., "Phase I/II Trial of Labetuzumab Govitecan (Anti-CEACAM5/ SN-38 Antibody-Drug Conjugate) in Patients With Refractory or Relapsing Metastatic Colorectal Cancer", Journal of Clinical Oncology. 2017. 35(29).

Gazzah et al., "Safety, pharmacokinetics, and antitumor activity of the anti-CEACAM5-DM4 antibody-drug conjugate tusamitamab ravtansine (SAR408701) in patients with advanced solid tumors: first-in-human dose-escalation study", Annal of Oncology. 2022. 33(4): 416-425.

International Search Report for International Application No. PCT/EP2023/057565 dated Jul. 7, 2023.

PubChem Compound Summary for CID 129896990, Spdb-DM4.

Bacac et al., "A novel carcinoembryonic antigen T-cell bispecific antibody (CEA TCB) for the treatment of solid tumors," Clinical Cancer Research, (Jul. 1, 2016); 22(13):3286-3297. doi: 10.1158/1078-0432.CCR-15-1696. Epub Feb. 9, 2016. PMID: 26861458.

Baek et al., "A highly-specific fully-human antibody and CAR-T cells targeting CD66e/CEACAM5 are cytotoxic for CD66e-expressing cancer cells in vitro and in vivo," Cancer Letters, (Jan. 28, 2022); 525:97-107. doi: 10.1016/j.canlet.2021.10.041. Epub Nov. 3, 2021. PMID: 34740610.

Beauchemin et al., "Carcinoembryonic antigen-related cell adhesion molecules (CEACAMs) in cancer progression and metastasis," Cancer Metastasis Reviews, (Aug. 2013), 29 pages. doi: 10.1007/s10555-013-9444-6. PMID: 23903773.

Beck et al., "Strategies and challenges for the next generation of antibody-drug conjugates," Nature Reviews Drug Discovery, (May 2017); 16(5):315-337. doi: 10.1038/nrd.2016.268. Epub Mar. 17, 2017. PMID: 28303026.

Bourgeaux et al., "Two-step enzymatic synthesis of UDP-N-acetylgalactosamine," Bioorganic & Medicinal Chemistry Letters, (Dec 15, 2005); 15(24):5459-5462. doi: 10.1016/j.bmcl.2005.08.088. Epub Oct. 3, 2005. PMID: 16203137.

Boxer et al., "Factors influencing variability of localisation of antibodies to carcinoembryonic antigen (CEA) in patients with colorectal carcinoma—implications for radioimmunotherapy," British Journal of Cancer, (Jun. 1992); 65(6):825-831. doi: 10.1038/bjc1992.176. PMID: 1616854.

Chari et al., "Antibody-drug conjugates: an emerging concept in cancer therapy," Angewandte Chemie International Edition, (Apr. 2014); 53(15):3796-3827. doi: 10.1002/anie.201307628.

Chau et al., "The value of routine serum carcino-embryonic antigen measurement and computed tomography in the surveillance of patients after adjuvant chemotherapy for colorectal cancer," Journal of Clinical Oncology, (Apr. 15, 2004); 22(8):1420-1429. doi: 10.1200/JCO.2004.05.041. Epub Mar. 8, 2004. PMID: 15007086.

Cook et al., "Pretargeted PET imaging using a site-specifically labeled immunoconjugate," Bioconjugate Chemistry, (Aug. 17, 2016); 27(8):1789-1795. doi: 10.1021/acs.bioconjchem.6b00235. Epub Jul. 14, 2016. PMID: 27356886.

Damelin et al., "A PTK7-targeted antibody-drug conjugate reduces tumor-initiating cells and induces sustained tumor regressions," Science Translational Medicine, (Jan. 11, 2017); 9(372):eaag2611, 12 pages. doi: 10.1126/scitranslmed.aag2611. PMID: 28077676.

Decary et al., "Preclinical activity of SAR408701: a novel anti-CEACAM5-maytansinoid antibody-drug conjugate for the treatment of CEACAM5-positive epithelial tumors," Clinical Cancer Research, (Dec 15, 2020); 26(24):6589-6599. doi: 10.1158/1078-0432.CCR-19-4051. Epub Oct. 12, 2020. PMID: 33046521.

Dufner et al., "Harnessing phage and ribosome display for antibody optimisation," Trends in Biotechnology, (Nov. 2006); 24(11):523-529. doi: 10.1016/j.tibtech.2006.09.004. Epub Sep. 26, 2006. PMID: 17000017.

Flamini et al., "Free DNA and carcinoembryonic antigen serum levels: an important combination for diagnosis of colorectal cancer," Clinical Cancer Research, (Dec 1, 2006); 12(23):6985-6988. doi: 10.1158/1078-0432.CCR-06-1931. PMID: 17145818.

Fu et al., "Antibody drug conjugate: the 'biological missile' for targeted cancer therapy," Signal Transduction and Targeted Therapy, (Mar. 22, 2022); 7(1):93, 25 pages. doi: 10.1038/s41392-022-00947-7. PMID: 35318309.

(56) References Cited

OTHER PUBLICATIONS

Galm et al., "Antitumor antibiotics: bleomycin, enediynes, and mitomycin," Chemical Reviews, (Feb. 2005); 105(2):739-758. doi: 10.1021/cr030117g. PMID: 15700963.
Genbank, Accession No. AAA51967.1, "carcinoembryonic antigen [Homo sapiens]," [sequence database entry], National Center for Biotechnology Information (NCBI), submitted Nov. 1, 1994. [Accessed Mar. 3, 2026, publicly available at URL: https://www.ncbi.nlm.nih.gov/protein/AAA51967.1/], 5 pages.
Gold et al., "Specific carcinoembryonic antigens of the human digestive system," Journal of Experimental Medicine, (Sep. 1, 1965); 122(3):467-481. doi: 10.1084/jem.122.3.467. PMID: 4953873.
Goldenberg, "Cancer imaging with CEA antibodies: historical and current perspectives," International Journal of Biological Markers, (Jul.-Sep. 1992); 7(3):183-188. PMID: 1431343.
Govindan et al., "CEACAM5-targeted therapy of human colonic and pancreatic cancer xenografts with potent labetuzumab-SN-38 immunoconjugates," Clinical Cancer Research, (Oct. 1, 2009); 15(19):6052-6061. doi: 10.1158/1078-0432.CCR-09-0586. Epub Sep. 29, 2009. PMID: 19789330.
Guan et al., "Highly efficient synthesis of UDP-GalNAc/GlcNAc analogues with promiscuous recombinant human UDP-GalNAc pyrophosphorylase AGX1," Chemistry—A European Journal, (Dec 3, 2010); 16(45):13343-13345. doi: 10.1002/chem.201002315. PMID: 21031374.
Hamann et al., "Gemtuzumab ozogamicin, a potent and selective anti-CD33 antibody-calicheamicin conjugate for treatment of acute myeloid leukemia," Bioconjugate Chemistry, (Jan.-Feb. 2002); 13(1):47-58. doi: 10.1021/bc010021y. PMID: 11792178.
Hammarström, "The carcinoembryonic antigen (CEA) family: structures, suggested functions and expression in normal and malignant tissues," Seminars in Cancer Biology, (Apr. 1999); 9(2):67-81. doi: 10.1006/scbi.1998.0119. PMID: 10202129.
Hansen et al., "Characterization of second-generation monoclonal antibodies against carcinoembryonic antigen," Cancer, (Jun. 1, 1993); 71(11):3478-3485. doi: 10.1002/1097-0142(19930601)71:113478:AID-CNCR28207111043.0.CO;2-A. PMID: 7683969.
Harwood et al., "Mapping epitope characteristics on carcinoembryonic antigen," British Journal of Cancer, (Jul. 1986); 54(1):75-82. doi: 10.1038/bjc1986.154. PMID: 2425837.
Hefta et al., "Carcinoembryonic antigen is anchored to membranes by covalent attachment to a glycosylphosphatidylinositol moiety: identification of the ethanolamine linkage site," Proceedings of the National Academy of Sciences of the United States of America, (Jul. 1988); 85(13):4648-4652. doi: 10.1073/pnas.85.13.4648. PMID: 3387431.
Hermanson, "Bioconjugate Techniques," 3rd ed., Chapter 3, Elsevier (Aug. 2013), pp. 229-258, 44 total pages.
Iwano et al., "Impact of different selectivity between soluble and membrane-bound forms of carcinoembryonic antigen (CEA) on the target-mediated disposition of anti-CEA monoclonal antibodies," Drug Metabolism and Disposition, (Nov. 2019); 47(11):1240-1246. doi: 10.1124/dmd.119.088179. Epub Sep. 18, 2019. PMID: 31533926.
Kuespert et al., "CEACAMs: their role in physiology and pathophysiology," Current Opinion in Cell Biology, (Oct. 2006); 18(5):565-571. doi: 10.1016/j.ceb.2006.08.008. Epub Aug. 17, 2006. PMID: 16919437.
Kuroki et al., "Nonspecific cross-reacting antigen-50/90 (NCA-50/90) as a new tumor marker," Anticancer Research, (Nov.-Dec. 1999); 19(6C):5599-5606. PMID: 10697625.
Kuroki et al., "Three different NCA species, CGM6/CD67, NCA-95, and NCA-90, are comprised in the major 90- to 100-kDa band of granulocyte NCA detectable upon SDS-polyacrylamide gel electrophoresis," Biochemical and Biophysical Research Communications, (Jan. 31, 1992); 182(2):501-506. doi: 10.1016/0006-291X(92)91760-N. PMID: 1370882.
Ledermann et al., "Repeated antitumour antibody therapy in man with suppression of the host response by cyclosporin A," British Journal of Cancer, (Nov. 1988); 58(5):654-657. doi: 10.1038/bjc.1988.279. PMID: 3265333.
Li et al., "Preparation of well-defined antibody-drug conjugates through glycan remodeling and strain-promoted azide-alkyne cycloadditions," Angewandte Chemie International Edition, (Jul. 2014); 53(28):7179-7182. doi: 10.1002/anie.201402606. Epub May 23, 2014. PMID: 24862406.
Mackness et al., "Antibody Fc engineering for enhanced neonatal Fc receptor binding and prolonged circulation half-life," mAbs, (Oct. 2019); 11(7):1276-1288. doi: 10.1080/19420862.2019.1633883. Epub Jul. 18, 2019. PMID: 31216930.
Maderna et al., "Recent advances in the development of new auristatins: structural modifications and application in antibody drug conjugates," Molecular Pharmaceutics, (Jun. 1, 2015); 12(6):1798-1812. doi: 10.1021/mp500762u. Epub Mar. 5, 2015. PMID: 25697404.
Medchemexpress, "Master of Bioactive Molecules | Inhibitors, Screening Libraries & Proteins," [website], medchemexpress.com, initial publication date unknown; last updated 2025. [Accessed May 7, 2025, publicly available at URL: https://www.medchemexpress.com/.], 2 pages.
Moon et al., "Antibody conjugates of 7-ethyl-10-hydroxycamptothecin (SN-38) for targeted cancer chemotherapy," Journal of Medicinal Chemistry, (Nov. 13, 2008); 51(21):6916-6926. doi: 10.1021/jm800719t. Epub Oct. 22, 2008. PMID: 18939816.
Nap et al., "Specificity and affinity of monoclonal antibodies against carcinoembryonic antigen," Cancer Research, (Apr. 15, 1992); 52(8):2329-2339. PMID: 1559235.
Niu et al., "Molecular targeting of CEACAM6 using antibody probes of different sizes," Journal of Controlled Release, (Jul. 10, 2012); 161(1):18-24. doi: 10.1016/j.jconrel.2012.04.043. Epub May 5, 2012. PMID: 22568933.
Okajima et al., "Datopotamab deruxtecan, a novel TROP2-directed antibody-drug conjugate, demonstrates potent antitumor activity by efficient drug delivery to tumor cells," Molecular Cancer Therapeutics, (Dec 2021); 20(12):2329-2340. doi: 10.1158/1535-7163.MCT-21-0206. Epub Aug. 19, 2021. PMID: 34413126.
PCT Application No. PCT/EP2019/080295, International Search Report and Written Opinion mailed Jan. 31, 2020, Applicant: Synaffix BV, 12 pages.
PCT Application No. PCT/EP2023/057560, International Search Report and Written Opinion mailed Jul. 4, 2023, Applicant: Synaffix BV, 12 pages.
PCT Application No. PCT/EP2023/057561, International Search Report and Written Opinion mailed Jul. 4, 2023, Applicant: Synaffix BV, 12 pages.
Pedley et al., "Comparative radioimmunotherapy using intact or $F(ab')_2$ fragments of $^{131}$I anti-CEA antibody in a colonic xenograft model," British Journal of Cancer, (Jul. 1993); 68(1):69-73. doi: 10.1038/bjc1993.288. PMID: 8318423.
Peng et al., "The CEA/CD3-bispecific antibody MEDI-565 (MT111) binds a nonlinear epitope in the full-length but not a short splice variant of CEA," PLoS One, (2012); 7(5): e36412, 14 pages. doi: 10.1371/journal.pone.0036412. Epub May 4, 2012. PMID: 22574157.
Pouilly et al., "Evaluation of analogues of GalNAc as substrates for enzymes of the mammalian GalNAc salvage pathway," ACS Chemical Biology, (Apr. 20, 2012); 7(4):753-760. doi: 10.1021/cb200511t. Epub Feb. 9, 2012. PMID: 22276930.
Richman et al., "Monoclonal antibodies to human colorectal epithelium: markers for differentiation and tumour characterization," International Journal of Cancer, (Mar. 15, 1987); 39(3):317-328. doi: 10.1002/ijc2910390309. PMID: 2434440.
Rudikoff et al., "Single amino acid substitution altering antigen-binding specificity," Proceedings of the National Academy of Sciences of the United States of America, (Mar. 1982); 79(6):1979-1983. doi: 10.1073/pnas.79.6.1979. PMID: 6804947.
Sakurai et al., "Conformational epitopes specific to carcinoembryonic antigen defined by monoclonal antibodies raised against colon cancer xenografts," Journal of Surgical Oncology, (Sep. 1989); 42(1):39-46. doi: 10.1002/jso.2930420110. PMID: 2475724.
Saunders, "Conceptual approaches to modulating antibody effector functions and circulation half-life," Frontiers in Immunology, (Jun. 7, 2019); 10:1296, 20 pages. doi: 10.3389/fimmu.2019.01296. PMID: 31231397.
Sheahan et al., "Differential reactivities of carcinoembryonic antigen (CEA) and CEA-related monoclonal and polyclonal antibodies

(56) References Cited

OTHER PUBLICATIONS in common epithelial malignancies," American Journal of Clinical Pathology, (Aug. 1990); 94(2):157-164. doi: 10.1093/ajcp/94.2.157. PMID: 1695478.

Shinmi et al., "Novel anticarcinoembryonic antigen antibody-drug conjugate has antitumor activity in the existence of soluble antigen," Cancer Medicine, (Apr. 2017); 6(4):798-808. doi: 10.1002/cam4.1003. Epub Feb. 17, 2017. PMID: 28211613.

Stewart et al., "Humanisation and characterisation of PR1A3, a monoclonal antibody specific for cell-bound carcinoembryonic antigen," Cancer Immunology, Immunotherapy, (Feb. 1999); 47(6):299-306. doi: 10.1007/s002620050534. PMID: 10203059.

Strickland et al., "Preclinical evaluation of carcinoembryonic cell adhesion molecule (CEACAM) 6 as potential therapy target for pancreatic adenocarcinoma," Journal of Pathology, (Jul. 2009); 218(3):380-390. doi: 10.1002/path.2545. PMID: 19334050.

Strop et al., "Location matters: site of conjugation modulates stability and pharmacokinetics of antibody drug conjugates," Chemistry & Biology, (Feb. 21, 2013); 20(2):161-167. doi: 10.1016/j.chembiol.2013.01.010. PMID: 23438745.

Strop et al., "RN927C, a site-specific Trop-2 antibody-drug conjugate (ADC) with enhanced stability, is highly efficacious in preclinical solid tumor models," Molecular Cancer Therapeutics, (Nov. 2016); 15(11):2698-2708. doi: 10.1158/1535-7163.MCT-16-0431. Epub Aug. 31, 2016. PMID: 27582525.

U.S. Appl. No. 19/284,359, filed Jul. 29, 2025, Inventor: Wijdeven et al.

U.S. Appl. No. 19/293,866, filed Aug. 7, 2025, Inventor: Wijdeven et al.

U.S. Appl. No. 19/355,628, filed Oct. 10, 2025, Inventor: Lelieveldt et al.

Ward et al., "Targeting FcRn for the modulation of antibody dynamics," Molecular Immunology, (Oct. 2015); 67(2 Pt A):131-141. doi: 10.1016/j.molimm.2015.02.007. Epub Mar. 9, 2015. PMID: 25766596.

Witzens-Harig et al., "Tumor cells in multiple myeloma patients inhibit myeloma-reactive T cells through carcinoembryonic antigen-related cell adhesion molecule-6," Blood, (May 30, 2013); 121(22):4493-4503. doi: 10.1182/blood-2012-05-429415. Epub Apr. 19, 2013. PMID: 23603913.

Wu et al., "Humanization of a murine monoclonal antibody by simultaneous optimization of framework and CDR residues," Journal of Molecular Biology, (Nov. 19, 1999); 294(1):151-162. doi: 10.1006/jmbi.1999.3141. PMID: 10556035.

Zhu et al., "Site specific antibody drug conjugation through an engineered glycotransferase and a chemically reactive sugar," mAbs, (Sep./Oct. 2014); 6(5):1190-1200. doi: 10.4161/mabs.29889. Epub Oct. 30, 2014. PMID: 25517304.

* cited by examiner

2a $R^1$ = OH; $R^2$ = $(CH_2)_2SH$
2b $R^1$ = OH; $R^2$ = $CH_2N_3$
2c $R^1$ = OH; $R^2$ = $CF_2N_3$
2d $R^1$ = $N_3$; $R^2$ = $CH_3$

A

B

C

D

E

F

G

H

I

J

K

L

M

N

O

P

Q

R

S

T

MMAE

MMAF calicheamicin derivative amanitin derivative

PBD dimer exatecan

PNU-159,682 derivative maytansin derivative

R = $CH_3$ (SN-38)
or $N(CH_3)_2$ (topotecan)

silatecan exatecan

R = OH
$NH_2$
NHMe belotecan

R = H (AMDCPT)
Gly (G-AMDCPT)

lurtotecan

R = H (DXd)
or cyclopropyl, cyclobutyl

R = (fluoro)alkyl exatecan-S

3 R =

4 R =

R =

5a n = 0
5b n = 1

6 R =

A

B

ANTIBODY-CONJUGATES FOR TARGETING OF TUMOURS EXPRESSING CARCINOEMBYRONIC ANTIGEN

RELATED APPLICATIONS

This application is a continuation of International Patent Application No. PCT/EP2023/057565, filed Mar. 23, 2023, which claims priority to European Patent Application Serial No. 22163928.9, filed Mar. 23, 2022, the entire disclosures of which are hereby incorporated herein by reference.

SEQUENCE LISTING

The content of the electronically submitted Sequence Listing (Name: "P6108677PCT.xml"; Size: 85,000 bytes; Date of Creation: Mar. 23, 2023) submitted in this application is incorporated herein by reference in its entirety.

FIELD OF THE INVENTION

The present invention is in the field of bioconjugation. More specifically, the present invention relates to antibody-drug conjugates for targeted treatment of patients with cancer, in particular carcinoembyronic antigen (CEA)-expressing tumours.

BACKGROUND

A promising approach for targeted treatment of tumours entails the conjugation of a multitude (2 to 8) of highly toxic payloads to a monoclonal antibody, thereby generating an antibody-drug conjugate (ADCs). ADCs are well known in the art, as for example described by Chari et al., *Angew. Chem. Int. Ed.* 2014, 53, 3796 and Beck et al., *Nat. Rev. Drug Discov.* 2017, 16, 315-37. Mechanistically, the antibody is designed to bind with high specificity to tumour-associated receptor that is overexpressed versus healthy tissue. The ADC is thought to internalize into the tumour cell after binding to the receptor, then to release the toxic payload upon degradation of the antibody and/or the linker in the lysosome.

Current ADCs are commonly prepared by various conjugation technologies (summarized in FIG. 1), mostly based on conjugation to cysteine side chains with maleimides or to lysine side chains with activated esters. To generate an ADC based on native cysteines naturally engaged in disulfide bonds, the thiol in the side-chain can be liberated by subjection of the antibody to a suitable reducing agent such as TCEP or DTT, followed by treatment with a maleimide-functionalized linker-drug. The resulting ADC will typically consist of a mixture of positional isomers, in case only the total of eight free thiols are not comprehensively alkylated. Alternatively, to generate a site-specific ADC, an antibody can be generated by mutating one or more amino acids at defined positions in the sequence to cysteines, the side-chain of which can be selectively liberated for alkylation by a reduction-oxidation sequence. Commonly employed cysteines for site-specific conjugation are LC-41C (light chain 41C), HC-41C (heavy chain 41C), LC-80C, HC-118C, HC-265C, HC-140C, LC-149C, LC-124C, LC-180C, HC-190C, HC-160C, LC-183C, HC-290C, LC-205C, HC-220C, HC-239C, HC-442C. An additional cysteine can also be inserted into the sequence, for example HC-i239C. Besides maleimides as alkylating agents, reaction of cysteine side chain with haloacetamide or vinylbenzene derivatives has also been reported. Besides reaction to natural amino acid side chains, specific unnatural (non-canonical) amino acids can also be engineered into the amino acid sequence of an antibody, thereby providing a unique handle for chemical conjugation, such as ketone, acetylene, azide, cyclic alkyne or cyclic alkene, for reaction with oxime, azide, alkyne or tetrazine, respectively. However, a disadvantage of the latter approach is that the natural sequence of the antibody must be re-engineered, which besides being time-consuming and costly, may lead to instability issues.

Conjugation through the glycan by an oxidation-ligation sequence is known in the art and has for example been described by Hamann et al. (*Bioconjugate Chem.* 2002, 13, 47-58). Chemoenzymatic conjugation through the glycan is known in the art and has been described for the use of sialyltransferase by Boons et al, *Angew. Chem. Int. Ed.* 2014, 53, 7179, and for the use of a mutant galactosyltransferase by Zhu et al, *mAbs* 2014, 6, 1 and Cook et al, *Bioconjugate Chem.* 2016, 27, 1789.

Chemoenzymatic conjugation through the glycan including first trimming of the glycan is known in the art and has been described by van Geel et al, *Bioconjugate Chem.* 2015, 26, 2233 and is schematically depicted in FIG. 2. In short, the monoclonal antibody is treated with an endoglycosidase to trim the glycan down to the core GlcNAc (attached directly to Asn-297), followed by transfer of an azido-modified sugar under the action of a glycosyltransferase. Various structures of UDP-azidosugars are depicted in FIG. 3. One particularly suitable combination involves that transfer of GalNAz 2b (2-azidoacetyl-N-galactosamine) under the action of a mutant galactosyltransferase GalT(Y289L) as disclosed in WO 2007/095506, EP 2911699 B1 and van Geel et al. An alternative powerful combination entails 6-azidoGalNAc 2d with native GalNAc-transferase, as has been disclosed in PCT/EP2016/059194. Another useful combination entails GlcNAz with a-1,3-mannosyl-glycoprotein-2-b-N-acetylglucosaminyltransferase (MGAT1) as disclosed in WO2021/248048.

Various cyclooctynes for application in metal-free click chemistry are known in the art (FIG. 4). In particular, various cyclooctynes such as DIBO (I), DBCO/DIBAC (J), s-DIBO (K), BCN (L) and TMTHSI (T) are regularly applied for conjugation to azide.

A payload for an ADCs is typically a highly cytotoxic molecule, with $IC_{50}$-value in low nanomolar or picomolar range, in particular low to medium molecular weight compounds (e.g. about 200 to about 2500 Da). Examples of suitable cytotoxin classes for ADCs include anthracyclines, camptothecins, taxanes, tubulysins, enediynes, inhibitory peptides, amanitins, duocarmycins, maytansinoids, auristatins, eribulins, hemiasterlins, BCL-XL inhibitors, KSP inhibitors, TLR agonists, indolinobenzodiazepine dimers or pyrrolobenzodiazepine dimers (PBDs) and analogues or prodrugs thereof. A representative set of cytotoxic molecules, and/or synthetic derivatives or prodrugs thereof, with suitable attachment point for conjugation to a monoclonal antibody, is depicted in FIG. 5.

Specific examples of anthracyclins suitable of application in ADCs include (but are not limited to) doxorubicin, daunorubicin, nemorubicin and PNU-159, 682.

Specific examples of camptothecins suitable for application in ADCs include (but are not limited to) SN-38, exatecan, exatecan-S, topotecan, silatecan, cositecan, lurtotecan, gimatecan, belotecan, rubitecan, AMDCPT, G-AMDCPT and other synthetic camptothecins the structures of which are depicted in FIG. 6. Various novel camptothecins have been disclosed in EP0296597, WO2019/

236954, WO2020/200880, WO2020/219287, CN113816969, CN113710277 and US20180200273.

Specific examples of enediynes suitable for application in ADCs include (but are not limited to) calicheamicin, esperamicins, shishijimicins and namenamicins and other enediynes as summarized by Galm et al., *Chem. Rev.* 2005, 105, 739-758.

Specific examples of auristatins suitable for application in ADCs include (but are not limited to) MMAD, MMAE, MMAF and PF-06380101 and other auristatins as summarized by Maderna et al., *Mol. Pharmaceutics* 2015, 12, 1798-1812.

The 7 genes that belong to the CEACAM subgroup show distinct expression patterns on different cell types but share structural homology, as they are composed, in their extracellular domains (ECDs), of Ig variable and constant-like domains, as reported by Kuespert et al. *Curr. Opin. Cell. Biol.* 2006, 18, 565-571, and Beauchemin et al., *Cancer Metastasis Rev.* 2013, DOI 10.1007/s10555-013-9444-6, see FIG. 8.

The gene carcinoembryonic antigen-related cell adhesion molecule 5 (CEACAM5), also known as CD66e, is the founding member of the CEACAM family, and was first identified by Gold and Freedman in 1965. CEACAM5 codes for the protein known as carcinoembryonic antigen (CEA), see Hefta et al. *Proc. Nat. Acad. Sci.* 1988, 85, 4648-4652. CEA is a glycoprotein involved in cell adhesion and is highly expressed in particular on the surface of colorectal, gastric, lung and uterine tumour cells. The CEACAM5 cDNA encodes a protein that exhibits one variable (V)-like domain, identified as the N domain, followed by three repeating units comprising, in total, six constant C2-like domains (termed A1, B1, A2, B2, A3, and B3, see FIG. 8. The Ig domains are preceded by a 34-amino acid signal peptide. In addition, the CEA cDNA structure predicted 12 cysteine residues forming the core of the Ig folds and 28 N-linked glycosylation sites in line with the high carbohydrate content of the purified protein.

A reference sequence of full length human CEACAM5, including signal peptide (positions 1-34) and pro-peptide (positions 686-702), is available from the GenBank database under accession number AAA51967.1. Domain organisation of human CEACAM5 is as follows:

| Human CEACAM5 domains | Positions |
|---|---|
| Domain N | 35-142 |
| Domain A1 | 143-237 |
| Domain B1 | 238-320 |
| Domain A2 | 321-415 |
| Domain B2 | 416-498 |
| Domain A3 | 499-593 |
| Domain B3 | 594-685 |

Accordingly, the A3-B3 domain of human CEACAM5 consists of amino acids at positions 499-685.

CEACAM5 has limited expression in normal adult tissues, but is overexpressed in carcinomas of the gastrointestinal tract, the genitourinary and respiratory systems, and breast cancer, as reported by Hammarstrom, *Semin. Cancer Biol.* 1999, 9, 67-81. Thus, CEACAM5 (CEA) may constitute a therapeutic target suitable for tumour specific targeting approaches, such as immunoconjugates or antibody-drug conjugates (ADCs).

Circulating CEA in serum is barely detectable in healthy adults (<5 ng/mL), but is shed from tumours, either directly or via the lymphatics, and is then detected in the serum. Because of this property, the level of serum CEA has been used as a clinical marker for diagnosis of cancers and screening for recurrence of cancers, particularly colorectal cancer (Goldenberg et al., *Int. J. Biol. Mark.* 1992, 7, 183-188; Chau et al. *J. Clin. Oncol.* 2004, 22, 1420-1429; Flamini et al. *Clin. Cancer Res.* 2006, 12, 6985-6988.

The high tumour expression levels of CEA relative to that in normal tissue makes this glycoprotein an attractive receptor for targeted treatment strategies with monoclonal antibodies. Therefore, multiple monoclonal antibodies have been raised, and humanized in various cases, against CEA for research purposes, as diagnostic tools and for therapeutic purposes, see for example various reviews summarizing anti-CEA antibodies, e.g. Nap et al., *Cancer Res.* 1992, 52, 2329-2339; Sheahan et al., *Am. J. Clin. Path.* 1990, 94, 157-164. Specific reports on anti-CEA antibodies: U.S. Pat. No. 9,695,250 (A5/A240VL and D8/A240VL); Richman et al., *Int. J. Cancer* 1987, 39, 317-32, Stewart et al., *Cancer Immunol. Immunother.* 1999, 47, 299-306, Ashraf et al., *Br. J. Canc.* 2009, 101, 1758-1768, WO199506067 and EP0721470 (PR1A3), Bacac et al. *Clin. Canc. Res.* 2016, 22, 3286-3297, U.S. Pat. Nos. 8,642,742 and 9,068,008 (antibodies based on VH CH1A1A/CH7A or CH1A1B/CH7A and VL pAC18/2F1); WO2021053587 (AB17, AB72 and AB73); U.S. Pat. No. 9,068,008; Sakurai et al., *J. Surg. Oncol.*, 1989, 42, 39-46 (antibodies NCC-CO-413, 308, 432, 411); Harwood et al., *Br. J. Cancer.* 1982, 54, 72; Ledermann, *Br. J. Cancer,* 1988, 58, 654; Pedley et al., *Br. J. Cancer,* 1993, 68, 69-73; Boxer et al., *Br. J. Cancer,* 1992, 65, 825-831 and U.S. Pat. No. 8,394,926 (antibody A5B7); Baek et al. *Canc. Lett.* 2022, 525, 97-107 (antibody 1G9); Hansen et al., *Cancer* 1993, 71, 347, U.S. Pat. No. 5,874,540 and humanized version thereof as described in U.S. Pat. Nos. 7,803,372, 8,778,342, WO2004032857A2, and WO2015069430A2 (hMN-14 or labetuzumab); U.S. Pat. No. 7,776,330 (antibodies M5A and M5B derived from murine T84.66). Chester et al. have isolated a single chain anti-CEA antibody (MFE-23) from a phage display library to be used in radioimmunodetection and radioimmunotherapy (U.S. Pat. No. 5,876,691), and the antibody was subsequently humanized (to SM3E) as described in U.S. Pat. No. 7,232,888 and US20050147614). Shinmi et al. *Canc. Med.* 2017, 6, 798-808 and Iwano et al. *Drug Metab. Dispos.* 2019, 47, 1240-1246 have isolated and used for targeted chemotherapy anti-CEA antibodies 12-140-1 and 15-1-32. Anti-CEA antibody CEA6 and other variants CEA1-CEA5 and CEA7, (derived from VH sequences T06D10, HBA11, HBB11, HBB6 and VL sequences T06D4, T06D8, T06D12) has been obtained from human phage display libraries (WO1997020932A1 and U.S. Pat. No. 5,872,215). Anti-CEA antibody 769-cea-4 was generated by immunization and humanized as described in U.S. Pat. Nos. 9,617,345 and 10,457,739 (tusamitamab or SAR408377). Micromet's MT111 antibody (also known as MEDI-565 antibody of MedImmune) is a bispecific antibody based on A5B7 for binding to human CEACAM5 and human CD3, as reported by Peng et al., *PLoS ONE* 2012, 7, e3641 and WO2007071426.

Another CEACAM family member CEACAM6 (also called CD66c) codes for the protein known as NCA-90. CEACAM6 is a non-specific cross-reacting glycoprotein antigen that shares some antigenic determinants with CEACAM5, as described by Kuroki et al., *Biochem. Biophys. Res. Comm.* 1992, 182, 501-506. CEACAM6 also is expressed on granulocytes and epithelia from various organs and has a broader expression zone in proliferating cells of hyperplastic colonic polyps and adenomas, compared with normal mucosa, as well as by many human cancers. Relatively high serum levels of NCA-90 are found in patients with lung, pancreatic, breast, colorectal, and hepatocellular carcinomas. The amount of CEACAM6 does not correlate with the amount of CEACAM5 expressed, as described by Kuroki et al., *Anticancer. Res.* 1999, 19, 5599-5606. In addition to structural homology, CEACAMs also share sequence similarity, with 85.7% sequence identity in the ECDs of CEACAM5 and CEACAM6, in particular.

Therapeutic antibodies against CEACAM6 are known in the art. Some are not selective for human CEACAM6 (e.g. Immunomedics MN-3, Neo201/h16C3 from Neogenix; both also bound to human CEACAM5). Single domain antibody 2A3 and its fusion mutants (WO2012040824 and Niu et al., *J. Contr. Rel.* 2012, 10, 18-24) have not been characterized with respect to selectivity and cross-reactivity for monkey CEACAM5. Mouse antibody 9A6 (Genovac/Aldevron) is the only antibody described to be capable of regulating the immunosuppressive activity of CEACAM6 (Witzens-Harig et al. *Blood* 2013, 121, 4493-4503). Potent anti-CECAM6 antibodies for cancer immunotherapy including TPP-3310 were disclosed in WO2016150899.

ADCs targeting CEACAM5 are known in the art. For example, Govindan et al. *Clin. Canc. Res.* 2009, 15, 6052-6061 have reported on the preclinical and clinical evaluation of an ADC known as labetuzumab-govetican obtained by modification of hMN-14 with CL2A linker-drug with SN-38 payload. Also, Shinmi et al. *Canc. Med.* 2017, 6, 798-808 and Iwano et al. *Drug Metab. Dispos.* 2019, 47, 1240-1246 have preclinically evaluated an anti-CEA ADC conjugated with MMAE payload based on antibodies 12-140-1 and 15-1-32. Thirdly, Decary et al. *Clin. Canc. Res.* 2020, 26, 6589-6599 have reported on derivatization and clinical evaluation of the anti-CEA antibody SAR408377 derivatized with DM4 payload, an ADC known as SAR408701 or tusamitamab-ravtansine.

ADCs against CEACAM6 are known in the art, such as the maytansinoid anti-CEACAM6 antibody reported by Genentech Strickland et al, *J. Pathol.* 2009, 218, 380, which in a non-human primate study was shown to induce CEACAM6-dependent haematopoietic toxicity. This toxicity, attributed to accumulation of the antibody drug conjugate in bone marrow and depletion of granulocytes and their cell precursors, was considered by the authors as a major safety concern.

SUMMARY OF THE INVENTION

The inventors have developed antibody-conjugates that are highly suitable for targeting CEA-expressing cells, in particular tumours. Thus, the antibody-conjugates according to the invention are highly suitable for treating CEA-positive cancer, especially colorectal cancer, gastric cancer, lung cancer, uterine cancer or pancreatic cancer.

In a first aspect, the present invention concerns an antibody-conjugate. Related thereto, in a second aspect, the invention concerns a process for preparing the antibody-conjugate according to the invention. In a third aspect, the invention concerns a method for targeting CEA-expressing cells. Related thereto are the first medical use of the antibody-conjugate according to the invention, as well as the second medical use for the treatment of cancer. In a last aspect, the invention concerns the use of a mode of conjugation for increasing the therapeutic index of an antibody-conjugate in the treatment of CEA-expressing tumours.

DETAILED DESCRIPTION

Definitions

The verb "to comprise", and its conjugations, as used in this description and in the claims is used in its non-limiting sense to mean that items following the word are included, but items not specifically mentioned are not excluded.

In addition, reference to an element by the indefinite article "a" or "an" does not exclude the possibility that more than one of the element is present, unless the context clearly requires that there is one and only one of the elements. The indefinite article "a" or "an" thus usually means "at least one".

A linker is herein defined as a moiety that connects (covalently links) two or more elements of a compound. A linker may comprise one or more spacer moieties. A spacer-moiety is herein defined as a moiety that spaces (i.e. provides distance between) and covalently links together two (or more) parts of a linker. The linker may be part of e.g. a linker-construct, a linker-conjugate, a linker-payload (e.g. linker-drug) or an antibody-conjugate, as defined below.

A "hydrophilic group" or "polar linker" is herein defined as any molecular structure containing one or more polar functional groups that imparts improved polarity, and therefore improved aqueous solubility, to the molecule it is attached to. Preferred hydrophilic groups are selected from a carboxylic acid group, an alcohol group, an ether group, a polyethylene glycol group, an amino group, an ammonium group, a sulfonate group, a phosphate group, an acyl sulfamide group or a carbamoyl sulfamide group. In addition to higher solubility other effects of the hydrophilic group include improved click conjugation efficiency, and, once incorporated into an antibody-drug conjugate: less aggregation, improved pharmacokinetics resulting in higher efficacy and in vivo tolerability.

The term "salt thereof" means a compound formed when an acidic proton, typically a proton of an acid, is replaced by a cation, such as a metal cation or an organic cation and the like. Where applicable, the salt is a pharmaceutically acceptable salt, although this is not required for salts that are not intended for administration to a patient. For example, in a salt of a compound the compound may be protonated by an inorganic or organic acid to form a cation, with the conjugate base of the inorganic or organic acid as the anionic component of the salt. The term "pharmaceutically accepted" salt means a salt that is acceptable for administration to a patient, such as a mammal (salts with counterions having acceptable mammalian safety for a given dosage regime). Such salts may be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions known in the art and include, for example, sodium, potassium, calcium, magnesium, ammonium, tetraalkylammonium, etc., and when the molecule contains a basic functionality, salts of organic or inorganic acids, such as hydrochloride, hydrobromide, formate, tartrate, besylate, mesylate, acetate, maleate, oxalate, etc.

The term "enediyne" or "enediyne antibiotic" or "enediyne-containing cytotoxin" refers to any cytotoxin characterized by the presence of a 3-ene-1,5-diyne structural feature as part of a cyclic molecule as known in the art and include neocarzinostatin (NCS), C-1027, kedarcidin (KED), maduropeptin (MDP), N1999A2, the sporolides (SPO), the cyanosporasides (CYA and CYN), and the fijiolides, calicheamicins (CAL), the esperamicins (ESP), dynemicin (DYN), namenamicin, shishijimicin, and uncialamycin (UCM).

The term "alkylaminosugar" as used herein means a tetrahydropyranyl moiety connected to an alcohol function via its 2-position, thereby forming an acetal function, and further substituted by (at least) one N-alkylamino group in position 3, 4 or 5. "N-alkylamino group" in this context refers to an amino group having one methyl, ethyl or 2-propyl group.

The term "click probe" refers to a functional moiety that is capable of undergoing a click reaction, i.e. two compatible click probes mutually undergo a click reaction such that they are covalently linked in the product. Compatible probes for click reactions are known in the art, and preferably include (cyclic) alkynes and azides. In the context of the present invention, click probe Q in the compound according to the invention is capable of reacting with click probe F on the (modified) protein, such that upon the occurrence of a click reaction, a conjugate is formed wherein the protein is conjugated to the compound according to the invention. Herein, F and Q are compatible click probes.

An "acylsulfamide moiety" is herein defined as a sulfamide moiety ($H_2NSO_2NH_2$) that is N-acylated or N-carbamoylated on one end of the molecule and N-alkylated (mono or bis) at the other end of the molecule. In the context of the present invention, especially in the examples, this group is also referred to as "HS".

A "domain" may be any region of a protein, generally defined on the basis of sequence homologies and often related to a specific structural or functional entity. CEACAM family members are known to be composed of Ig-like domains. The term domain is used in this document to designate either individual Ig-like domains, such as "N-domain" or for groups of consecutive domains, such as "A3-B3 domain".

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

The term "gene" means a DNA sequence that codes for, or corresponds to, a particular sequence of amino acids which comprises all or part of one or more proteins or enzymes, and may or may not include regulatory DNA sequences, such as promoter sequences, which determine for example the conditions under which the gene is expressed. Some genes, which are not structural genes, may be transcribed from DNA to RNA, but are not translated into an amino acid sequence. Other genes may function as regulators of structural genes or as regulators of DNA transcription. In particular, the term gene may be intended for the genomic sequence encoding a protein, i.e. a sequence comprising regulator, promoter, intron and exon sequences.

The term "glycoprotein" is herein used in its normal scientific meaning and refers to a protein comprising one or more monosaccharide or oligosaccharide chains ("glycans") covalently bonded to the protein. A glycan may be attached to a hydroxyl group on the protein (O-linked-glycan), e.g. to the hydroxyl group of serine, threonine, tyrosine, hydroxylysine or hydroxyproline, or to an amide function on the protein (N-glycoprotein), e.g. asparagine or arginine, or to a carbon on the protein (C-glycoprotein), e.g. tryptophan. A glycoprotein may comprise more than one glycan, may comprise a combination of one or more monosaccharide and one or more oligosaccharide glycans, and may comprise a combination of N-linked, O-linked and C-linked glycans. It is estimated that more than 50% of all proteins have some form of glycosylation and therefore qualify as glycoprotein. Examples of glycoproteins include PSMA (prostate-specific membrane antigen), CAL (*Candida antartica* lipase), gp41, gp120, EPO (erythropoietin), antifreeze protein and antibodies.

The term "glycan" is herein used in its normal scientific meaning and refers to a monosaccharide or oligosaccharide chain that is linked to a protein. The term glycan thus refers to the carbohydrate-part of a glycoprotein. The glycan is attached to a protein via the C-1 carbon of one sugar, which may be without further substitution (monosaccharide) or may be further substituted at one or more of its hydroxyl groups (oligosaccharide). A naturally occurring glycan typically comprises 1 to about 10 saccharide moieties. However, when a longer saccharide chain is linked to a protein, said saccharide chain is herein also considered a glycan. A glycan of a glycoprotein may be a monosaccharide. Typically, a monosaccharide glycan of a glycoprotein consists of a single N-acetylglucosamine (GlcNAc), glucose (Glc), mannose (Man) or fucose (Fuc) covalently attached to the protein. A glycan may also be an oligosaccharide. An oligosaccharide chain of a glycoprotein may be linear or branched. In an oligosaccharide, the sugar that is directly attached to the protein is called the core sugar. In an oligosaccharide, a sugar that is not directly attached to the protein and is attached to at least two other sugars is called an internal sugar. In an oligosaccharide, a sugar that is not directly attached to the protein but to a single other sugar, i.e. carrying no further sugar substituents at one or more of its other hydroxyl groups, is called the terminal sugar. For the avoidance of doubt, there may exist multiple terminal sugars in an oligosaccharide of a glycoprotein, but only one core sugar. A glycan may be an O-linked glycan, an N-linked glycan or a C-linked glycan. In an O-linked glycan a monosaccharide or oligosaccharide glycan is bonded to an O-atom in an amino acid of the protein, typically via a hydroxyl group of serine (Ser) orthreonine (Thr). In an N-linked glycan a monosaccharide or oligosaccharide glycan is bonded to the protein via an N-atom in an amino acid of the protein, typically via an amide nitrogen in the side chain of asparagine (Asn) or arginine (Arg). In a C-linked glycan a monosaccharide or oligosaccharide glycan is bonded to a C-atom in an amino acid of the protein, typically to a C-atom of tryptophan (Trp).

The term "antibody" (AB) is herein used in its normal scientific meaning. An antibody is a protein generated by the immune system that is capable of recognizing and binding to a specific antigen. An antibody is an example of a glycoprotein. The term antibody herein is used in its broadest sense and specifically includes monoclonal antibodies, polyclonal antibodies, dimers, multimers, multispecific antibodies (e.g. bispecific antibodies), antibody fragments, and double and single chain antibodies. The term "antibody" is herein also meant to include human antibodies, humanized antibodies, chimeric antibodies and antibodies specifically binding cancer antigen. The term "antibody" is meant to include whole antibodies, but also fragments of an antibody, for example an antibody Fab fragment, F(ab')2, Fv fragment or Fc fragment from a cleaved antibody, a scFv-Fc fragment, a minibody, a diabody or a scFv. Furthermore, the term includes genetically engineered antibodies and derivatives of an antibody. Antibodies, fragments of antibodies and genetically engineered antibodies may be obtained by methods that are known in the art.

An antibody may be a natural or conventional antibody in which two heavy chains are linked to each other by disulfide bonds and each heavy chain is linked to a light chain by a disulfide bond. There are two types of light chain, lambda (l) and kappa (k). The light chain includes two domains or regions, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties, such as antibody chain association, secretion, trans-placental mobility, complement binding, and binding to Fc receptors (FcR). The Fv fragment is the N-terminal part of the Fab fragment of an immunoglobulin and consists of the variable portions of one light chain and one heavy chain. The immunoglobulin can be of any type (e.g. IgG, IgE, IgM, IgD, and IgA), class (e.g. IgG1 IgG2, IgG3, IgG4, IgA1 and IgA2) or subclass, or allotype (e.g. human G1m1, G1m2, G m3, non-G1m1 [that, is any allotype other than G1m1], G1m17, G2m23, G3m21, G3m28, G3m1.1, G3m5, G3m13, G3m14, G3m10, G3m15, G3m16, G3m6, G3m24, G3m26, G3m27, A2m1, A2m2, Km1, Km2 and Km3) of immunoglobulin molecule. Preferred allotypes for administration include a non-G1m1 allotype (nG1m1), such as G1m17,1, G1m3, G1m3.1, G1m3.2 or G1m3.1.2. More preferably, the allotype is selected from the group consisting of the G1m17,1 or G1m3 allotype. The antibody may be engineered in the Fc-domain to enhance or nihilate binding to Fc-gamma receptors, as summarized by Saunders et al. *Front. Immunol.* 2019, 10, doi: 10.3389/fimmu.2019.01296 and Ward et al., *Mol. Immunol.* 2015, 67, 131-141. For example, the combination of Leu234Ala and Leu235Ala (commonly called LALA mutations) eliminate FcγRIIa binding. Elimination of binding to Fc-gamma receptors can also be achieved by mutation of the N297 amino acid to any other amino acid except asparagine, by mutation of the T299 amino acid to any other amino acid except threonine or serine, or by enzymatic deglycosylation or trimming of the fully glycosylated antibody with for example PNGase F or an endoglycosidase. The immunoglobulins can be derived from any species, including human, murine, or rabbit origin. Each chain contains distinct sequence domains.

A percentage of "sequence identity" may be determined by comparing the two sequences, optimally aligned over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. A sequence "at least 85% identical to a reference sequence" is a sequence having, on its entire length, 85%, or more, for instance 90%, 91%, 92%, 93%, 94%, 95%, 96%, 97%, 98% or 99% sequence identity with the entire length of the reference sequence.

The term "CDR" refers to complementarity-determining region: the specificity of the antibody resides in the structural complementarity between the antibody combining site and the antigenic determinant. Antibody combining sites are made up of residues that are primarily from the hypervariable or complementarity determining regions (CDRs). Occasionally, residues from non-hypervariable or framework regions (FR) influence the overall domain structure and hence the combining site. Complementarity Determining Regions or CDRs therefore refer to amino acid sequences which together define the binding affinity and specificity of the natural Fv region of a native immunoglobulin binding site. The light and heavy chains of an immunoglobulin each have three CDRs, designated CDR1-L, CDR2-L, CDR3-L and CDR1-H, CDR2-H, CDR3-H, respectively. A conventional antibody antigen-binding site, therefore, includes six CDRs, comprising the CDR set from each of a heavy and a light chain V region. "CDR"

The term "monoclonal antibody" or "mAb" as used herein refers to an antibody molecule of a single amino acid sequence, which is directed against a specific antigen, and is not to be construed as requiring production of the antibody by any particular method. A monoclonal antibody may be produced by a single clone of B cells or hybridoma, but may also be recombinant, i.e. produced by protein engineering.

The term "chimeric antibody" refers to an engineered antibody which, in its broadest sense, contains one or more regions from one antibody and one or more regions from one or more other antibodies. In an embodiment, a chimeric antibody comprises a VH domain and a VL domain of an antibody derived from a non-human animal, in association with a CH domain and a CL domain of another antibody, in an embodiment, a human antibody. As the non-human animal, any animal such as mouse, rat, hamster, rabbit or the like can be used. A chimeric antibody may also denote a multispecific antibody having specificity for at least two different antigens.

The term "humanised antibody" refers to an antibody which is wholly or partially of non-human origin and which has been modified to replace certain amino acids, for instance in the framework regions of the VH and VL domains, in order to avoid or minimize an immune response in humans. The constant domains of a humanized antibody are most of the time human CH and CL domains. "Fragments" of (conventional) antibodies comprise a portion of an intact antibody, in particular the antigen binding region or variable region of the intact antibody. Examples of antibody fragments include Fv, Fab, F(ab')2, Fab', dsFv, (dsFv)2, scFv, sc(Fv)2, diabodies, bispecific and multispecific antibodies formed from antibody fragments. A fragment of a conventional antibody may also be a single domain antibody, such as a heavy chain antibody or VHH.

As used herein "CEA" or "CEACAM5" designates the "carcino-embryonic antigen-related cell adhesion molecule 5", also known as "CD66e" (Cluster of Differentiation 66e). CEA and CEACAM5 are used exchangeably herein.

DESCRIPTION OF FIGURES

FIGS. 13(A)-(C) show the plots corresponding to colorectal IC-003P PDX model. Clear tumor regression is observed for this model. FIGS. 13(M)-(O) show the plots corresponding to pancreatic IM-PAN-07 PDX model with also high tumor growth inhibition.

THE INVENTION

Figure 1:
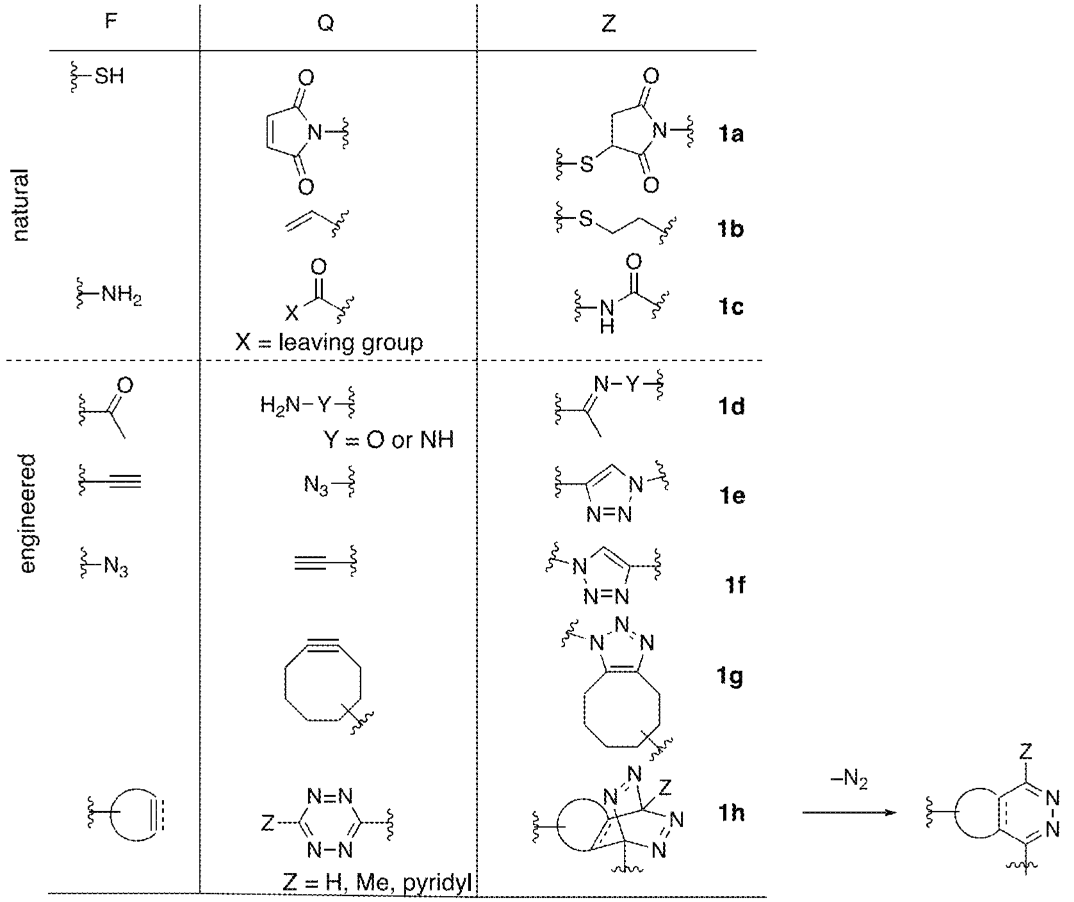
FIG. 1 shows a representative set of reactive groups (F) that when present in a biomolecule lead to connecting group Z (1a-1h) upon reaction with reactive group Q. Functional groups F can be naturally present of may be artificially introduced (engineered) into a biomolecule at any position of choice.
Figure 2:
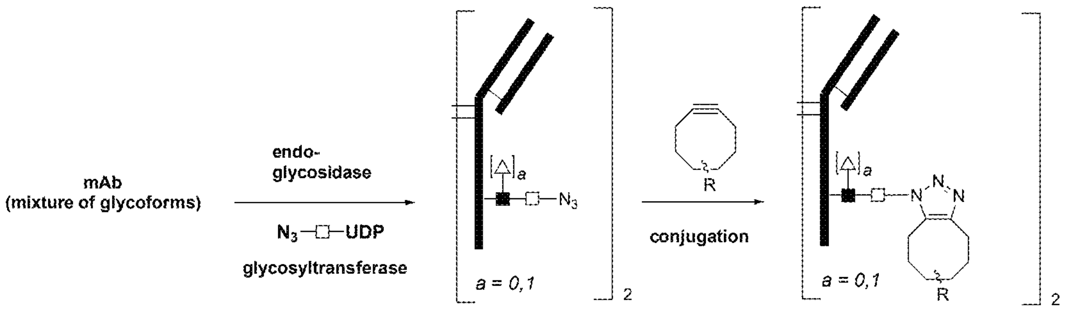
FIG. 2 schematically displays how an antibody conjugate can be obtained from any monoclonal antibody in a two-stage process. In the first stage, an azido-modified UPD-Gal or UDP-GalNAc may be attached to the monoclonal antibody in a one pot process involving (a) trimming of the glycan by an endoglycosidase (to the core GlcNAc) and (b) attachment of the azido-sugar under the action of a glycosyltransferase (a galactosyltransferase or a mutant thereof or a GalNAc-transferase), thereby generating a β-glycosidic 1-4 linkage between the azido-modified GalNAc and GlcNAc. In the second stage, the azido-modified antibody is reacted with an appropriately functionalized cyclooctyne, thereby generating the antibody conjugate.

In a first aspect, the invention concerns antibody-conjugates of general structure (1)

$$AB\text{-}[(L^6)_b\text{-}\{Z\text{-}L\text{-}D\}_x]_y \quad (1)$$

wherein:

AB is an antibody capable of targeting CEA-expressing tumours;

L is a linker that links Z to D;

Z is a connecting group;

$L^6$ is -GlcNAc(Fuc)$_w$-(G)$_j$-S-($L^7$)$_{w'}$-, wherein G is a monosaccharide, j is an integer in the range of 0-10, S is a sugar or a sugar derivative, GlcNAc is N-acetylglucosamine and Fuc is fucose, w is 0 or 1, w' is 0, 1 or 2 and $L^7$ is —N(H)C(O)$CH_2$—, —N(H)C(O)$CF_2$— or —$CH_2$—;

D is selected from the group consisting of anthracyclines, camptothecins, tubulysins, enediynes, amanitins, duocarmycins, maytansinoids, auristatins, eribulins, BCL-XL inhibitors, hemiasterlins, KSP inhibitors, TLR agonists, indolinobenzodiazepine dimers or pyrrolobenzodiazepine dimers (PBDs), and analogues or prodrugs thereof;

b is 0 or 1;

x is 1 or 2; and y is 1, 2, 3 or 4.

Also contemplated within the present invention are salts, preferably pharmaceutically acceptable salts, of the antibody-conjugate according to structure (1).

In a second aspect, the invention concerns a process for preparing the antibody-conjugate according to the invention, comprising reacting the compound according to general structure (2) with an antibody (3). The compound according to general structure (2) comprises a reactive moiety Q and the antibody a reactive moiety F which is capable of reacting with Q in a conjugation reaction, wherein Q and F react to form connecting group Z. In this reaction, a conjugate according to general structure (1) is formed. The process according to this aspect this concerns the following bioconjugation reaction:

$$AB—[(L^6)_b—\{F\}_x]_y \quad + \quad Z—L—D \longrightarrow$$

(3) (2)

$$AB—[(L^6)_b—\{Z—L—D\}_x]_y$$

(1)

Here below, the antibody-conjugate according to structure (1) is first defined. The structural features of the antibody-conjugate according to structure (1) also apply to the compound according to structure (2) and the antibody according to structure (3), as those are unchanged in the conjugation reaction except for reactive moieties F and Q, which are transformed into connecting group Z upon reaction of the compound according to structure (2) with an antibody according to structure (3).

In a third aspect, the invention concerns the application antibody-conjugate according to structure (1), for targeting CEA-expressing cells. Related thereto, the invention concerns the first medical use and second medical use of the antibody-conjugate according to structure (1).

As will be understood by the skilled person, the definition of the chemical moieties, as well as their preferred embodiments, apply to all aspects of the invention.

Antibody-Conjugate of General Structure (1)

In a first aspect, the invention concerns antibody-conjugates of general structure (1):

$$AB\text{-}[(L^6)_b\text{-}\{Z\text{-}L\text{-}D\}_x]_y \qquad (1)$$

wherein:

AB is an antibody capable of targeting CEA-expressing tumours;

b is 0 or 1;

$L^6$ is -GlcNAc(Fuc)$_w$-(G)$_j$-S-($L^7$)$_{w'}$-, wherein G is a monosaccharide, j is an integer in the range of 0-10, S is a sugar or a sugar derivative, GlcNAc is N-acetylglucosamine and Fuc is fucose, w is 0 or 1, w' is 0, 1 or 2 and $L^7$ is —N(H)C(O)$CH_2$—, —N(H)C(O)$CF_2$— or —$CH_2$—;

Z is a connecting group;

L is a linker that links Z to D;

D is selected from the group consisting of anthracyclines, camptothecins, tubulysins, enediynes, amanitins, duocarmycins, maytansinoids, auristatins, eribulins, BCL-XL inhibitors, hemiasterlins, KSP inhibitors, TLR agonists, indolinobenzodiazepine dimers or pyrrolobenzodiazepine dimers (PBDs), and analogues or prodrugs thereof;

x is 1 or 2; and y is 1, 2, 3 or 4.

Antibody AB

The antibody-conjugate according to the invention contains an antibody that is capable of targeting CEA-expressing cells, in particular tumour cells. Carcinoembryonic antigen (CEA) is a known target for cancer treatment, and is encoded by the CEACAM5 gene. The term "expressing" is used as common in the art, and refers to overexpression of the target with respect to the expression in healthy tissue. Antibodies capable of targeting CEA-expressing tumours may also be referred to as anti-CEA antibodies, CEA-targeting antibodies or CEA-binding antibodies. Anti-CEA antibodies selectively bind to CEA-expressing cells.

Anti-CEA antibodies are known in the art, and any suitable one can be used in the context of the present invention. Preferred antibodies are selected from the list consisting of labetuzumab, A5/A240VL, D8/A240VL, PR1A3, CH1A1A/pAC18, CH1A1B/pAC18, AB173, AB14AB72, AB15AB73, NCC-CO-413, NCC-CO-308, NCC-CO-432, NCC-CO-411, A5B7, 1G9, CEA6, T84.66M5A, M5B, MFE-23, SM3E, 12-140-1, 15-1-32, tusamitamab, MT111, and humanized or functional analogues thereof. More preferably, the antibody is PR1A3, SM3E, huMAb2-4, tusamitamab or labetuzumab, even more preferably the antibody is tusamitamab or labetuzumab, most preferably the antibody is labetuzumab.

Herein, the Fc regions of these antibodies may have one or more mutations, such as 0-10 mutations or 0-5 mutations. Especially preferred are mutations that change binding to the FcRn receptor to modulate half-life of the antibody. For example, inclusion of mutations Met-to-Tyr, Ser-to-Thr and Thr-to-Glu in the region of amino acids 254-260 of the heavy chain, often called YTE, in the IgG1 Fc results in a ~11-fold higher binding of the antibody to human FcRn, thereby increasing the circulation half-life with a factor ~3.5. For example, the YTE mutations for tusamitamab are Met255Tyr, Ser257Thr and Thr259Glu, and for labetuzumab, the YTE mutations are Met254Tyr, Ser256Thr and Thr258Glu. Therefore, in one embodiment, the antibody has an apparent human FcRn binding affinity $K_{D,app}$ of below $2.5\times10^{-6}$ M, preferably in the range of 0.05-$0.99\times10^{-6}$ M, more preferably in the range of 0.1-$0.49\times10^{-6}$ M, most preferably in the range of 0.2-$0.4\times10^{-6}$ M. The apparent binding affinity $K_{D,app}$ may be determined according to Mackness et al. *MABS,* 2019, 11(7), 1276-1288. In a preferred embodiment, the antibody AB is the YTE mutant of the preferred antibodies defined here above or below.

Labetuzumab is also known as hMN-14 and may also be defined as containing a light chain sequence according to SEQ ID No. 38 and a heavy chain sequence according to SEQ ID No. 36 or 37, preferably SEQ ID No. 36, wherein the sequence identity is at least 90%, preferably at least 95%, more preferably at least 99%, most preferably 100%. In a particularly preferred embodiment, the antibody according to this embodiment is combined with a payload D selected from the group consisting of calicheamicin, MMAE, PF-06380101, exatecan and DXd, more preferably with a payload D selected from the group consisting of calicheamicin, MMAE, and exatecan, most preferably with exatecan as payload D.

Tusamitamab is also known as huMAb2-3 or as SAR408377 and may also be defined as containing a light chain sequence according to SEQ ID No. 43 and a heavy chain sequence according to SEQ ID No. 41 or 42, preferably SEQ ID No. 41, wherein the sequence identity is at least 90%, preferably at least 95%, more preferably at least 99%, most preferably 100%. In a particularly preferred embodiment, the antibody according to this embodiment is combined with a payload D selected from the group consisting of calicheamicin, MMAE, PF-06380101, exatecan and DXd, more preferably with a payload D selected from the group consisting of calicheamicin, MMAE, and exatecan, most preferably with exatecan as payload D.

M5B may also be defined as containing a light chain sequence according to SEQ ID No. 8 and a heavy chain sequence according to SEQ ID No. 7, wherein the sequence identity is at least 90%, preferably at least 95%, more preferably at least 99%, most preferably 100%. In a particularly preferred embodiment, the antibody according to this embodiment is combined with a payload D selected from the group consisting of calicheamicin, MMAE, PF-06380101, exatecan and DXd, more preferably with a payload D selected from the group consisting of calicheamicin, MMAE, and exatecan, most preferably with exatecan as payload D.

D8 may also be defined as containing a light chain sequence according to SEQ ID No. 15 and a heavy chain sequence according to SEQ ID No. 14, wherein the sequence identity is at least 90%, preferably at least 95%, more preferably at least 99%, most preferably 100%. In a particularly preferred embodiment, the antibody according to this embodiment is combined with a payload D selected from the group consisting of calicheamicin, MMAE, PF-06380101, exatecan and DXd, more preferably with a payload D selected from the group consisting of calicheamicin, MMAE, and exatecan, most preferably with exatecan as payload D.

SM3E may also be defined as containing a light chain sequence according to SEQ ID No. 19 and a heavy chain sequence according to SEQ ID No. 18, wherein the sequence identity is at least 90%, preferably at least 95%, more preferably at least 99%, most preferably 100%. In a particularly preferred embodiment, the antibody according to this embodiment is combined with a payload D selected from the group consisting of calicheamicin, MMAE, PF-06380101, exatecan and DXd, more preferably with a payload D selected from the group consisting of calicheamicin, MMAE, and exatecan, most preferably with exatecan as payload D.

PR1A3 may also be defined as containing a light chain sequence according to SEQ ID No. 23 and a heavy chain sequence according to SEQ ID No. 22, wherein the sequence identity is at least 90%, preferably at least 95%, more preferably at least 99%, most preferably 100%. In a particularly preferred embodiment, the antibody according to this embodiment is combined with a payload D selected from the group consisting of calicheamicin, MMAE, PF-06380101, exatecan and DXd, more preferably with a payload D selected from the group consisting of calicheamicin, MMAE, and exatecan, most preferably with exatecan as payload D.

huMAb2-4 may also be defined as containing a light chain sequence according to SEQ ID No. 47 and a heavy chain sequence according to SEQ ID No. 46, wherein the sequence identity is at least 90%, preferably at least 95%, more preferably at least 99%, most preferably 100%. In a particularly preferred embodiment, the antibody according to this embodiment is combined with a payload D selected from the group consisting of calicheamicin, MMAE, PF-06380101, exatecan and DXd, more preferably with a payload D selected from the group consisting of calicheamicin, MMAE, and exatecan, most preferably with exatecan as payload D.

Alternatively, the antibody is defined by its $V_L$ and $V_H$ domains, which together form the variable domain that binds to the antigen. Thus, in a preferred embodiment, the antibody contains a $V_L$ domain selected from the group consisting of SEQ ID No. 2, 6, 10, 17, 21, 28, 31, 35, 40, 45, 49, 50 and 51, and a $V_H$ domain selected from the group consisting of SEQ ID No. 1, 3, 5, 9, 11, 13, 16, 20, 24, 26, 30, 34, 39, 44 and 48, wherein the sequence identity is at least 70%, preferably at least 75% or at least 80%, more preferably at least 85% or at least 90% or at least 95%, most preferably at least 99% or even 100%. In a further preferred embodiment, the antibody contains a $V_L$ domain selected from the group consisting of SEQ ID No. 17, 21, 35 and 40, and a $V_H$ domain selected from the group consisting of SEQ ID No. 16, 20, 34 and 39, wherein the sequence identity is at least 70%, preferably at least 75% or at least 80%, more preferably at least 85% or at least 90% or at least 95%, most preferably at least 99% or even 100%. In a more preferred embodiment, the antibody contains a $V_L$ domain selected from the group consisting of SEQ ID No. 35 and 40, and a $V_H$ domain selected from the group consisting of SEQ ID No. 34 and 39, wherein the sequence identity is at least 70%, preferably at least 75% or at least 80%, more preferably at least 85% or at least 90% or at least 95%, most preferably at least 99% or even 100%. In a most preferred embodiment, the antibody contains a $V_L$ domain of SEQ ID No. 35, and a $V_H$ domain of SEQ ID No. 34, wherein the sequence identity is at least 70%, preferably at least 75% or at least 80%, more preferably at least 85% or at least 90% or at least 95%, most preferably at least 99% or even 100%.

The aforementioned sequence identities refer to the complete sequence of the $V_L$ and $V_H$ domains. While the entire sequences of these domains allow for some variation in the sequence without jeopardizing the binding to CEA, it is preferred that the complementarity-determining regions (CDRs) have a higher sequence identity, to ensure that the binding to CEA is not significantly jeopardized. The location of the CDRs is given in the tables below. Thus, it is preferred that the antibody contains a $V_L$ domain selected from the group consisting of SEQ ID No. 2, 6, 10, 17, 21, 28, 31, 35, 40, 45, 49, 50 and 51, and a $V_H$ domain selected from the group consisting of SEQ ID No. 1, 3, 5, 9, 11, 13, 16, 20, 24, 26, 30, 34, 39, 44 and 48, preferably a $V_L$ domain selected from the group consisting of SEQ ID No. 17, 21, 35 and 40, and a $V_H$ domain selected from the group consisting of SEQ ID No. 16, 20, 34 and 39, more preferably a $V_L$ domain selected from the group consisting of SEQ ID No. 35 and 40, and a $V_H$ domain selected from the group consisting of SEQ ID No. 34 and 39, most preferably a $V_L$ domain of SEQ ID No. 35, and a $V_H$ domain of SEQ ID No. 34, wherein the sequence identity of the CDR is at least 90%, preferably at least 95%, more preferably at least 99%, most preferably 100%. The skilled person understands that the $V_L$ and $V_H$ domains identified above can be combined with a suitable constant domain to form a complete antibody.

Preferred $V_L$ Domains

| SEQ ID No. | CDR (amino acid numbers within the sequence) |
|---|---|
| 2 | 24-34 \| 50-56 \| 89-97 |
| 6 | 24-38 \| 54-60 \| 93-101 |
| 10 | 23-36 \| 52-62 \| 97-106 |
| 17 | 26-30 \| 49-51 \| 90-95 |
| 21 | 25-34 \| 50-52 \| 89-98 |
| 28 | 24-34 \| 49-56 \| 89-98 |
| 31 | 24-34 \| 49-56 \| 89-98 |
| 35 | 24-34 \| 50-56 \| 89-96 |
| 40 | 26-31 \| 49-51 \| 88-96 |
| 45 | 26-31 \| 49-51 \| 88-96 |
| 49 | 24-34 \| 50-56 \| 89-99 |
| 50 | 24-34 \| 50-56 \| 89-99 |
| 51 | 24-34 \| 50-56 \| 89-99 |

Preferred $V_H$ Domains

| SEQ ID No. | CDR (amino acid numbers within the sequence) |
|---|---|
| 1 | 31-35 \| 50-66 \| 99-112 |
| 3 | 31-35 \| 50-66 \| 99-110 |
| 5 | 31-36 \| 50-65 \| 99-110 |
| 9 | 31-35 \| 50-68 \| 101-110 |
| 11 | 31-35 \| 50-62 \| 99-108 |
| 13 | 31-35 \| 50-66 \| 99-108 |
| 16 | 26-32 \| 52-57 \| 100-108 |

-continued

| SEQ ID No. | CDR (amino acid numbers within the sequence) |
|---|---|
| 20 | 20-35 ǀ 50-66 ǀ 97-110 |
| 24 | 31-35 ǀ 50-66 ǀ 99-110 |
| 26 | 31-35 ǀ 50-66 ǀ 99-110 |
| 30 | 31-35 ǀ 50-65 ǀ 99-110 |
| 34 | 31-35 ǀ 50-66 ǀ 99-108 |
| 39 | 26-33 ǀ 51-58 ǀ 97-109 |
| 44 | 26-33 ǀ 51-58 ǀ 97-109 |
| 48 | 26-35 ǀ 50-68 ǀ 99-114 |

In an especially preferred embodiment, the antibody contains a $V_L$ domain of SEQ ID No. 2 and a $V_H$ domain of SEQ ID No. 1, or a $V_L$ domain of SEQ ID No. 6 and a $V_H$ domain of SEQ ID No. 3 or 5, or a $V_L$ domain of SEQ ID No. 10 and a $V_H$ domain of SEQ ID No. 9, or a $V_L$ domain of SEQ ID No. 17 and a $V_H$ domain of SEQ ID No. 16, or a $V_L$ domain of SEQ ID No. 21 and a $V_H$ domain of SEQ ID No. 20, or a $V_L$ domain of SEQ ID No. 31 and a $V_H$ domain of SEQ ID No. 30, or a $V_L$ domain of SEQ ID No. 35 and a $V_H$ domain of SEQ ID No. 34, or a $V_L$ domain of SEQ ID No. 40 and a $V_H$ domain of SEQ ID No. 39, or a $V_L$ domain of SEQ ID No. 45 and a $V_H$ domain of SEQ ID No. 44, or a $V_L$ domain of SEQ ID No. 49, 50 or 51 and a $V_H$ domain of SEQ ID No. 48. Herein, the sequence identities as defined above for the complete sequence as well as for the CDR apply.

Alternatively, the antibody is defined by its light and heavy chains, which together form the antibody. Thus, in a preferred embodiment, the antibody contains a light chain selected from the group consisting of SEQ ID No. 8, 15, 19, 23, 29, 33, 38, 43 and 47, and a heavy chain selected from the group consisting of SEQ ID No. 4, 7, 12, 14, 18, 22, 25, 27, 32, 36, 37, 41, 42 and 46, wherein the sequence identity is at least 70%, preferably at least 75% or at least 80%, more preferably at least 85% or at least 90% or at least 95%, most preferably at least 99% or even 100%. In a further preferred embodiment, the antibody contains a light chain selected from the group consisting of SEQ ID No. 19, 23, 38 and 43, and a heavy chain selected from the group consisting of SEQ ID No. 18, 22, 36, 37, 41 and 42, wherein the sequence identity is at least 70%, preferably at least 75% or at least 80%, more preferably at least 85% or at least 90% or at least 95%, most preferably at least 99% or even 100%. In a more preferred embodiment, the antibody contains a light chain selected from the group consisting of SEQ ID No. 38 and 43, and a heavy chain selected from the group consisting of SEQ ID No. 36 and 41, wherein the sequence identity is at least 70%, preferably at least 75% or at least 80%, more preferably at least 85% or at least 90% or at least 95%, most preferably at least 99% or even 100%. In a most preferred embodiment, the antibody contains a light chain selected from the group consisting of SEQ ID No. 38, and a heavy chain selected from the group consisting of SEQ ID No. 36, wherein the sequence identity is at least 70%, preferably at least 75% or at least 80%, more preferably at least 85% or at least 90% or at least 95%, most preferably at least 99% or even 100%.

The aforementioned sequence identities refer to the complete sequence of the light and heavy chains. While the entire sequences of these chains allow for some variation in the sequence without jeopardizing the binding to CEA, it is preferred that the CDRs have a higher sequence identity, to ensure that the binding to CEA is not significantly jeopardized. The location of the CDRs is given in the tables below. Thus, it is preferred that the antibody contains a light chain selected from the group consisting of SEQ ID No. 8, 15, 19, 23, 29, 33, 38, 43 and 47, and a heavy chain selected from the group consisting of SEQ ID No. 4, 7, 12, 14, 18, 22, 25, 27, 32, 36, 37, 41, 42 and 46, wherein the sequence identity of the CDR is at least 90%, preferably at least 95%, more preferably at least 99%, most preferably 100%.

Preferred Light Chains

| SEQ ID No. | CDR (amino acid numbers within the sequence) |
|---|---|
| 8 | 24-38 ǀ 54-60 ǀ 93-101 |
| 15 | 23-36 ǀ 52-62 ǀ 97-106 |
| 19 | 26-30 ǀ 49-51 ǀ 90-95 |
| 23 | 25-34 ǀ 50-52 ǀ 89-98 |
| 29 | 24-34 ǀ 49-56 ǀ 89-98 |
| 33 | 24-34 ǀ 49-56 ǀ 89-98 |
| 38 | 24-34 ǀ 50-56 ǀ 89-96 |
| 43 | 26-31 ǀ 49-51 ǀ 88-96 |
| 47 | 26-31 ǀ 49-51 ǀ 88-96 |

Preferred Heavy Chains

| SEQ ID No. | CDR (amino acid numbers within the sequence) |
|---|---|
| 4 | 31-35 ǀ 50-66 ǀ 99-110 |
| 7 | 31-36 ǀ 50-65 ǀ 99-110 |
| 12 | 31-35 ǀ 50-62 ǀ 99-108 |
| 14 | 31-35 ǀ 50-66 ǀ 99-108 |
| 18 | 26-32 ǀ 52-57 ǀ 100-108 |
| 22 | 20-35 ǀ 50-66 ǀ 97-110 |
| 25 | 31-35 ǀ 50-66 ǀ 99-110 |
| 27 | 31-35 ǀ 50-66 ǀ 99-110 |
| 32 | 31-35 ǀ 50-65 ǀ 99-110 |
| 36 | 31-35 ǀ 50-66 ǀ 99-108 |
| 37 | 31-35 ǀ 50-66 ǀ 99-108 |
| 41 | 26-33 ǀ 51-58 ǀ 97-109 |
| 42 | 26-33 ǀ 51-58 ǀ 97-109 |
| 46 | 26-33 ǀ 51-58 ǀ 97-109 |

In an especially preferred embodiment, the antibody contains a light chain of SEQ ID No. 8 and a heavy chain of SEQ ID No. 7, or a light chain of SEQ ID No. 15 and a heavy chain of SEQ ID No. 14, or a light chain of SEQ ID No. 19 and a heavy chain of SEQ ID No. 18, or a light chain of SEQ ID No. 23 and a heavy chain of SEQ ID No. 22, or a light chain of SEQ ID No. 33 and a heavy chain of SEQ ID No. 32, or a light chain of SEQ ID No. 38 and a heavy chain of SEQ ID No. 36 or 37, preferably 36, or a light chain of SEQ ID No. 43 and a heavy chain of SEQ ID No. 41 or 42, preferably 41, or a light chain of SEQ ID No. 47 and a heavy chain of SEQ ID No. 46. Herein, the sequence identities as defined above for the complete sequence as well as for the CDR apply.

Linker $L^6$

In case reactive group F is directly connected to the antibody, or even part of the antibody structure, linker $L^6$ that connects AB to F (for antibodies of structure (3)) or AB to Z (for conjugates of structure (1) is absent and b=0. This is for example the case for cysteine conjugation and lysine conjugation. Alternatively, reactive group F may also be introduced onto the antibody using a linker $L^6$ that connects AB to F (for antibodies of structure (3)) or AB to Z (for conjugates of structure (1), in which case $L^6$ is present and b=1. In case $L^6$ is present, reactive group F is typically introduced at the glycan of the antibody. This is for example the case for conjugation via an artificially introduced reactive group F, such as for example using transglutaminase or by enzymatic glycan modification (e.g. glycosyltransferase or a-1,3-mannosyl-glycoprotein-2-b-N-acetylglucosaminyltransferase). For example, a modified sugar residue $S(F)_x$ may be introduced at the glycan, extending the glycan with one monosaccharide residue S, which introduces x reactive groups F on the glycan of an antibody. In a most preferred embodiment, conjugation occurs via the glycan of the antibody and b=1. The site of conjugation is preferably at the heavy chain of the antibody.

If present, $L^6$ is a linker that links AB to F or Z, and is represented by -GlcNAc(Fuc)$_w$-(G)$_j$-S-($L^7$)$_{w'}$-, wherein G is a monosaccharide, j is an integer in the range of 0-10, S is a sugar or a sugar derivative, GlcNAc is N-acetylglucosamine and Fuc is fucose, w is 0 or 1, w' is 0, 1 or 2 and $L^7$ is —N(H)C(O)$CH_2$—, —N(H)C(O)$CF_2$— or —$CH_2$—. Typically, $L^6$ is at least partly formed by the glycan of the antibody. All recombinant antibodies, generated in mammalian host systems, contain the conserved N-glycosylation site at the asparagine residue at or close to position 297 of the heavy chain, which is modified by a glycan of the complex type. This naturally occurring glycosylation site of antibodies is preferably used, but other glycosylation sites, including artificially introduced ones, may also be used for the connection of linker $L^6$. Thus, in a preferred embodiment, $L^6$ is connected to an amino acid of the antibody which is located at a position in the range of 250-350 of the heavy chain, preferably in the range of 280-310 of the heavy chain, more preferably in the range of 295-300 of the heavy chain, most preferably at position 297 of the heavy chain.

The -GlcNAc(Fuc)$_w$-(G)$_j$- of $L^6$ is the glycan of the antibody, or part thereof. The -GlcNAc(Fuc)$_b$-(G)$_j$- of the glycan thus typically originates from the original antibody, wherein GlcNAc is an N-acetylglucosamine moiety and Fuc is a fucose moiety. Fuc is typically bound to GlcNAc via an α-1,6-glycosidic bond. Normally, antibodies may (w=1) or may not be fucosylated (w=0). In the context of the present invention, the presence of a fucosyl moiety is irrelevant, and similar effects are obtained with fucosylated (w=1) and non-fucosylated (w=0) antibody conjugates. The GlcNAc residue may also be referred to as the core-GlcNAc residue and is the monosaccharide that is directly attached to the peptide part of the antibody.

S may be directly connected to the core-GlcNAc(Fuc)$_w$ moiety, i.e. j=0, meaning that the remainder of the glycan is removed from the core-GlcNAc(Fuc)$_w$ moiety before S is attached. Such trimming of glycans is well-known in the art and can be achieved by the action of an endoglycosidase. Alternatively, there are one or more monosaccharide residues present in between the core-GlcNAc(Fuc)$_w$ moiety and S, i.e. j is an integer in the range of 1-10, preferably j=2-5. In a preferred embodiment, (G)$_j$ is an oligosaccharide fraction comprising j monosaccharide residues G, wherein j is an integer in the range of 2-5. (G)$_j$ is connected to the GlcNAc moiety of GlcNAc(Fuc)$_w$, typically via a β-1,4 bond. In a preferred embodiment, j is 3, 4 or 5. Although any monosaccharide that may be present in a glycan may be employed as G, each G is preferably individually selected from the group consisting of galactose, glucose, N-acetylgalactosamine, N-acetylglucosamine, mannose and N-acetylneuraminic acid. More preferred options for G are galactose, N-acetylglucosamine, mannose. The inventors found that antibody-conjugates having j below 4 show no or hardly any binding to the Fc-gamma receptor, while antibody conjugates having j in the range of 4-10 do bind to the Fc-gamma receptor. Thus, by selecting a certain value for j, the desired extent of binding to the Fc-gamma receptor can be obtained. It is thus preferred that j=0, 3, 4, 5, 6, 7, 8, 9 or 10, more preferably j=0, 3, 4 or 5, most preferably the antibody is trimmed and j=0.

S is a sugar or sugar derivative. The term "sugar derivative" is herein used to indicate a derivative of a monosaccharide sugar, i.e. a monosaccharide sugar comprising substituents and/or functional groups. Suitable examples for S include glucose (Glc), galactose (Gal), mannose (Man), fucose (Fuc), amino sugars and sugar acids, e.g. glucosamine ($GlcNH_2$), galactosamine ($GalNH_2$)N-acetylglucosamine (GlcNAc), N-acetylgalactosamine (GalNAc), sialic acid (Sia) which is also referred to as N-acetylneuraminic acid (NeuNAc), and N-acetylmuramic acid (MurNAc), glucuronic acid (GlcA) and iduronic acid (IdoA). Preferably, S is selected from Glc, Gal, GlcNAc and GalNAc. In an especially preferred embodiment, S is GalNAc.

x is an integer that denotes the number of connecting groups Z (for conjugate (1)) or reactive groups F (for antibody (3)) that are attached to sugar (derivative) S. Thus, the antibody according to the invention contains a moiety S comprising x reactive moieties F. Each of these reactive moieties F are reacted with a reactive moiety Q of the compound according to general structure (2), such that x connecting groups Z are formed and x compounds according to general structure (2) are attached to a single occurrence of S. x is 1 or 2, preferably x=1.

Connecting group Z (for conjugate (1)) or reactive group F (for antibody (3)) may be attached directly to S, or there may be a linker $L^7$ present in between S and Z or F. $L^7$ is a linker that links S with Z. $L^7$ may be present (w'=1 or 2) or absent (w'=0). Typically, each moiety Z may be connected to S via a linker $L^7$, thus in one embodiment w'=0 of x. Preferably, $L^7$ is absent and each connecting moiety Z is directly attached to S. If present, $L^7$ may be selected from —N(H)C(O)$CH_2$—, —N(H)C(O)$CF_2$— or —$CH_2$—. In a preferred embodiment, x=1 and w'=0 or 1, most preferably x=1 and w'=0.

y is an integer that denotes the number of sugar(s) (derivative(s)) S, each having x reactive groups F or connected to x connecting groups Z, that are connected to the antibody. y is 1, 2, 3 or 4, preferably y=2 or 4, most preferably y=2. Thus, the antibody contains y moieties S, each of which comprises x reactive moieties F. Each of these reactive moieties F are reacted with reactive moiety Q of the compound according to general structure (2), such that x+y connecting groups Z are formed and x+y compounds according to general structure (2) are attached to a single antibody. Each compound according to general structure (2) may contain multiple payloads, e.g. by virtue of branching nitrogen atom N* in L. It is preferred that each compound according to general structure (2) contains 1 or 2 occurrences of D, most preferably 2 occurrences of D. In an especially preferred embodiment, linker $L^1$ contains a branching nitrogen atom N* to which a second occurrence of D is connected.

The amount of payload (D) molecules attached to a single antibody is known in the art as the DAR (drug-antibody ratio). In the context of the present invention, it is preferred that DAR is an integer in the range 1-8, more preferably 2 or 4, most preferably DAR=4. Alternatively worded, the DAR is preferably an integer in the range (x+y) to [(x+y)×2], most preferably DAR=[(x+y)×2]. With preferred values for x of 1 and y of 2, the DAR is preferably 4. It will be appreciated that these are theoretical DAR values, and in practice the DAR may slightly deviate from this value, by virtue of incomplete conjugation. Typically, the conjugates are obtained as a stochastic mixture of antibody-drug conjugates, with DAR values varying between individual conjugates, and depending on the conjugation technique used the DAR may have a broad distribution (e.g. DAR=0-10) or a narrow distribution (e.g. DAR=3-4). In case of such mixture, DAR often refers to the average DAR of the mixture. This is well-known in the art of bioconjugation. However, in case the conjugation occurs via the glycan (i.e. b=1 and $L^6$ is present), the antibody-conjugates according to the invention have a close-to-theoretical DAR. For example, when the theoretical DAR is 4, DAR values above 3.6 or even above 3.8 are readily obtained, indicating that most antibodies in the reaction mixture have reacted completely and have a DAR of 4.

Connecting Group Z

Z is a connecting group, which covalently connects both parts of the conjugate according to the invention. The term "connecting group" herein refers to the structural element, resulting from the reaction between Q and F, connecting one part of the conjugate with another part of the same conjugate. As will be understood by the person skilled in the art, the nature of a connecting group depends on the type of reaction with which the connection between the parts of said compound is obtained. As an example, when the carboxyl group of R—C(O)—OH is reacted with the amino group of $H_2N$—R' to form R—C(O)—N(H)—R', R is connected to R' via connecting group Z, and Z may be represented by the group —C(O)—N(H)—. Since connecting group Z originates from the reaction between Q and F, it can take any form.

Since more than one reactive moiety F can be present or introduced in an antibody, the antibody-conjugate according to the present invention may contain per biomolecule more than one payload D, such as 1-8 payloads D, preferably 1, 2, 3 or 4 payloads D, more preferably 2 or 4 payloads D. The number of payloads is typically an even integer, in view of the symmetric nature of antibodies. In other words, when one side of the antibody is functionalized with F, the symmetrical counterpart will also be functionalized. Alternatively, in case naturally occurring thiol groups of the cysteine residues of a protein are used as F, the value of m can be anything and may vary between individual conjugates.

In a compound according to structure (1), connecting group Z connects D via linker L to AB, optionally via $L^6$. Numerous reactions are known in the art for the attachment of a reactive group Q to a reactive group F. Consequently, a wide variety of connecting groups Z may be present in the conjugate according to the invention. In one embodiment, the reactive group Q is selected from the options described above, preferably as depicted in FIG. 1, and complementary reactive groups F and the thus obtained connecting groups Z are known to a person skilled in the art. Several examples of suitable combinations of F and Q, and of connecting group $Z^3$ that will be present in a bioconjugate when a linker-conjugate comprising Q is conjugated to a biomolecule comprising a complementary reactive group F, are shown in FIG. 1.

For example, when F comprises or is a thiol group, complementary groups Q include N-maleimidyl groups and alkenyl groups, and the corresponding connecting groups Z are as shown in FIG. 1. When F comprises or is a thiol group, complementary groups Q also include allenamide groups.

For example, when F comprises or is an amino group, complementary groups Q include ketone groups and activated ester groups, and the corresponding connecting groups Z are as shown in FIG. 1.

For example, when F comprises or is a ketone group, complementary groups Q include (O-alkyl)hydroxylamino groups and hydrazine groups, and the corresponding connecting groups Z are as shown in FIG. 1.

For example, when F comprises or is an alkynyl group, complementary groups Q include azido groups, and the corresponding connecting group Z is as shown in FIG. 1.

For example, when F comprises or is an azido group, complementary groups Q include alkynyl groups, and the corresponding connecting group Z is as shown in FIG. 1.

For example, when F comprises or is a cyclopropenyl group, a trans-cyclooctene group or a cyclooctyne group, complementary groups Q include tetrazinyl groups, and the corresponding connecting group Z is as shown in FIG. 1. In these particular cases, Z is only an intermediate structure and will expel N2, thereby generating a dihydropyridazine (from the reaction with alkene) or pyridazine (from the reaction with alkyne).

Additional suitable combinations of F and Q, and the nature of resulting connecting group Z3 are known to a person skilled in the art, and are e.g. described in G. T. Hermanson, "Bioconjugate Techniques", Elsevier, 3rd Ed. 2013 (ISBN:978-0-12-382239-0), in particular in Chapter 3, pages 229-258, incorporated by reference. A list of complementary reactive groups suitable for bioconjugation processes is disclosed in Table 3.1, pages 230-232 of Chapter 3 of G. T. Hermanson, "Bioconjugate Techniques", Elsevier, 3rd Ed. 2013 (ISBN:978-0-12-382239-0), and the content of this Table is expressly incorporated by reference herein.

In a preferred embodiment, connecting group Z is obtained by a cycloaddition or a nucleophilic reaction, preferably wherein the cycloaddition is a [4+2]cycloaddition or a 1,3-dipolar cycloaddition or the nucleophilic reaction is a Michael addition or a nucleophilic substitution. Such a cycloaddition or nucleophilic reaction occurs via a reactive group F, connected to S, and reactive group Q, connected to D via L. Conjugation reactions via cycloadditions or nucleophilic reactions are known to the skilled person, and the skilled person is capable of selecting appropriate reaction partners F and Q, and will understand the nature of the resulting connecting group Z.

In a first preferred embodiment, Z is formed by a cycloaddition. Preferred cycloadditions are a (4+2)-cycloaddition (e.g. a Diels-Alder reaction) or a (3+2)-cycloaddition (e.g. a 1,3-dipolar cycloaddition). Preferably, the conjugation is the Diels-Alder reaction or the 1,3-dipolar cycloaddition. The preferred Diels-Alder reaction is the inverse-electron demand Diels-Alder cycloaddition. In another preferred embodiment, the 1,3-dipolar cycloaddition is used, more preferably the alkyne-azide cycloaddition, and most preferably wherein Q is or comprises an alkyne group and F is an azido group. Cycloadditions, such as Diels-Alder reactions and 1,3-dipolar cycloadditions are known in the art, and the skilled person knowns how to perform them.

Preferably, Z contains a moiety selected from the group consisting of a triazole, a cyclohexene, a cyclohexadiene, a [2.2.2]-bicyclooctadiene, a [2.2.2]-bicyclooctene, an isoxazoline, an isoxazolidine, a pyrazoline, a piperazine, a thioether, an amide or an imide group. Triazole moieties are especially preferred to be present in Z. In one embodiment, Z comprises a (hetero)cycloalkene moiety, i.e. formed from Q comprising a (hetero)cycloalkyne moiety. In an alternative embodiment, Z comprises a (hetero)cycloalkane moiety, i.e. formed from Q comprising a (hetero)cycloalkene moiety. In a preferred embodiment, Z has the structure (Z1):

(Z1)

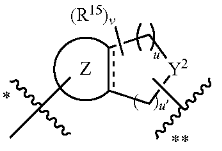

Herein, the bond depicted as --- is a single bond or a double bond. Furthermore:

ring Z is obtained by a cycloaddition, preferably ring Z is selected from (Za)-(Zj) defined below, wherein the carbon atoms labelled with ** correspond to the two carbon atoms of the bond depicted as --- of (Z1) to which ring Z is fused;

$R^{15}$ is independently selected from the group consisting of hydrogen, halogen, —$OR^{16}$, —$NO_2$, —CN, —$S(O)_2R^{16}$, —$S(O)_3^{(-)}$, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups and wherein the alkyl groups, (hetero)aryl groups, alkyl(hetero)aryl groups and (hetero)arylalkyl groups are optionally substituted, wherein two substituents $R^{15}$ may be linked together to form an optionally substituted annulated cycloalkyl or an optionally substituted annulated (hetero)arene substituent, and wherein $R^{16}$ is independently selected from the group consisting of hydrogen, halogen, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero) arylalkyl groups;

$Y^2$ is $C(R^{31})_2$, O, S, $S^{(+)}R^{31}$, $S(O)R^{31}$, $S(O){=}NR^{31}$ or $NR^{31}$, wherein SN is a cationic sulphur atom counterbalanced by $B^{(-)}$, wherein $B^{(-)}$ is an anion, and wherein each $R^{31}$ individually is $R^{15}$ or a connection with D, connected via L;

u is 0, 1, 2, 3, 4 or 5;

u' is 0, 1, 2, 3, 4 or 5, wherein u+u'=0, 1, 2, 3, 4, 5, 6, 7 or 8;

v=an integer in the range 8-16;

Ring A is formed by the cycloaddition, and is preferably selected from (Za)-(Zj).

In case the bond depicted as --- is a double bond, it is preferred that u+u'=4, 5, 6, 7 or 8. Preferably, the wavy bond labelled with * is connected to S and the wavy bond labelled with ** is connected to L.

It is especially preferred that Z comprises a (hetero) cycloalkene moiety, i.e. the bond depicted as --- is a double bond. In a preferred embodiment, Z is selected from the structures (Z2)-(Z20), depicted here below:

(Z2)

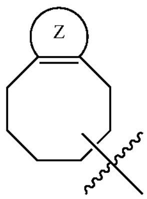

-continued (Z3)

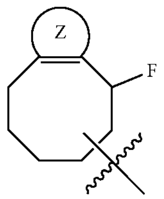

(Z4)

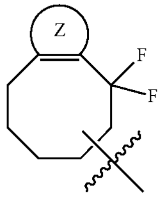

(Z5)

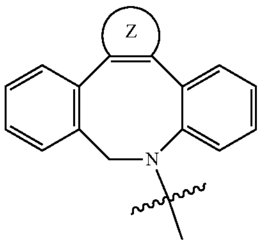

(Z6)

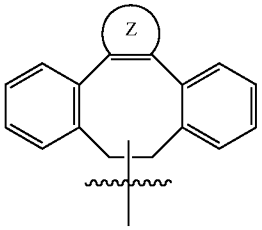

(Z7)

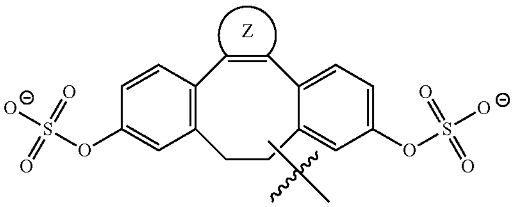

(Z8)

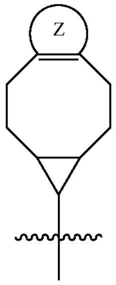

-continued
(Z9)
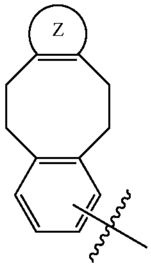
(Z10)
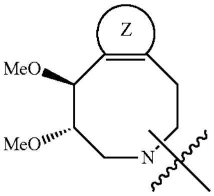
(Z11)
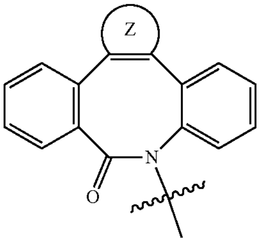
(Z12)
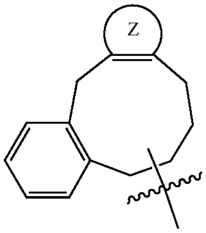
(Z13)
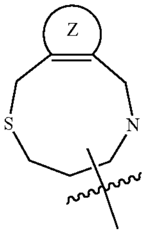
(Z14)
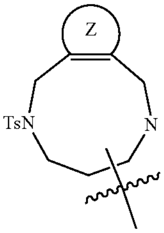
-continued
(Z15)
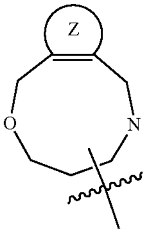
(Z16)
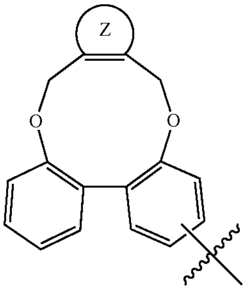
(Z17)
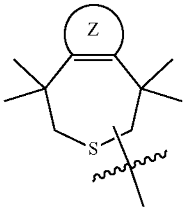
(Z18)
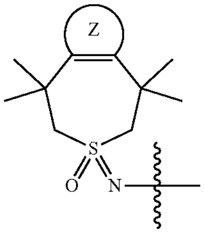
(Z19)
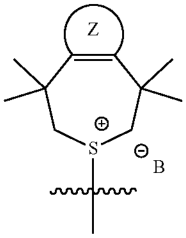
(Z20)
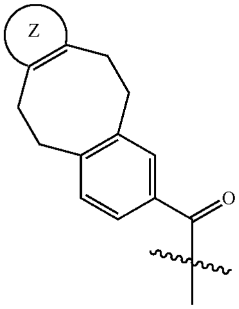
Herein, the connection to L is depicted with the wavy bond. $B^{(-)}$ is an anion, preferably a pharmaceutically acceptable anion. Ring Z is formed by the cycloaddition reaction, and preferably is a triazole, a cyclohexene, a cyclohexadiene, a [2.2.2]-bicyclooctadiene, a [2.2.2]-bicyclooctene, an isoxazoline, an isoxazolidine, a pyrazoline or a piperazine. Most preferably, ring Z is a triazole ring. Ring Z may have the structure selected from (Za)-(Zm) depicted below, wherein the carbon atoms labelled with ** correspond to the two carbon atoms of the (hetero)cycloalkane ring of (Z2)-(Z20) to which ring Z is fused. Preferred rings Z are selected from (Za)-(Zj), more preferably from (Za), (Zd) and (Zh), most preferably ring Z has structure (Za). Since the connecting group Z is formed by reaction with a (hetero) cycloalkyne in the context of the present embodiment, the bound depicted above as == = is a double bond.

(Za)

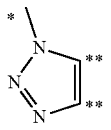

(Zb)

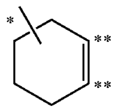

(Zc)

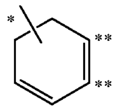

(Zd)

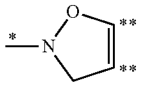

(Ze)

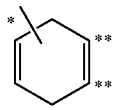

(Zf)

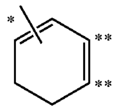

(Zg)

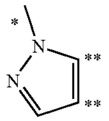

(Zh)

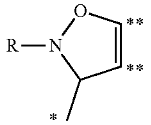

(Zi)

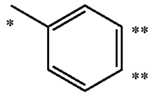

-continued (Zj)

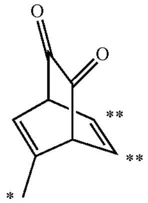

(Zk)

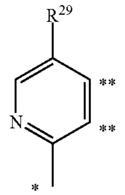

(Zl)

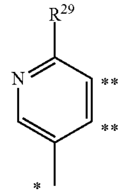

(Zm)

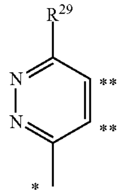

In a further preferred embodiment, Z is selected from the structures (Z21)-(Z38) and (Z38a), depicted here below:

(Z21)

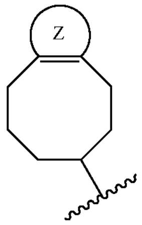

(Z22)

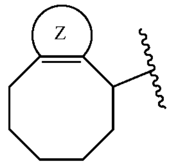

-continued
(Z23)
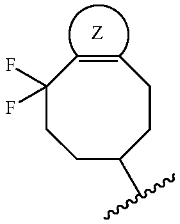
(Z24)
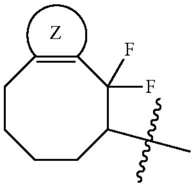
(Z25)
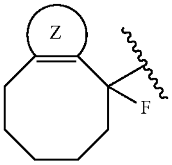
(Z26)
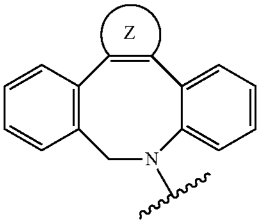
(Z27)
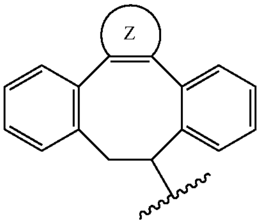
(Z28)
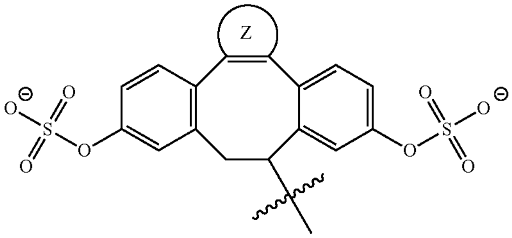
(Z29)
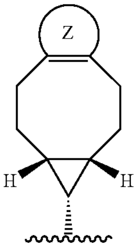
-continued
(Z30)
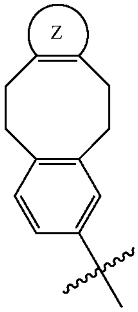
(Z31)
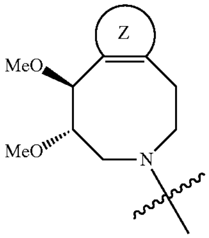
(Z32)
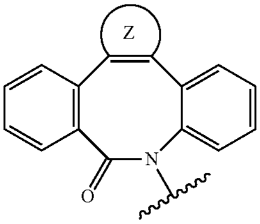
(Z33)
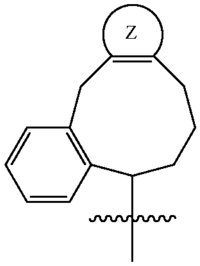
(Z34)
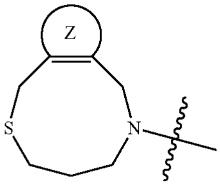
(Z35)
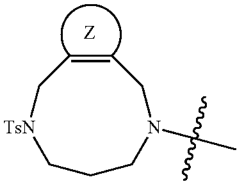

-continued (Z36)

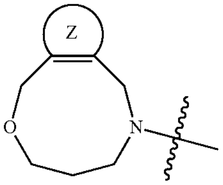

(Z37)

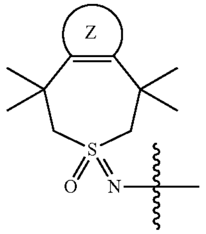

(Z38)

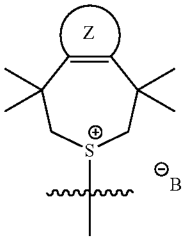

(Z38a)

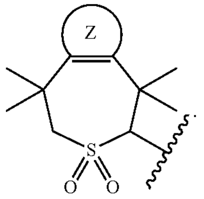

Herein, the connection to L is depicted with the wavy bond. In structure (Z38), $B^{(-)}$ is an anion, preferably a pharmaceutically acceptable anion. Ring Z is selected from structures (Za)-(Zm), preferably from structures (Za)-(Zj), as defined above.

In a preferred embodiment, Z comprises a (hetero)cyclooctene moiety or a (hetero)cycloheptene moiety, preferably according to structure (Z8), (Z26), (Z27), (Z28) or (Z37) or (Z38a), more preferably according to structure (Z8), (Z26), (Z27), (Z28) or (Z37), which are optionally substituted. Each of these preferred options for Z are further defined here below.

Thus, in a preferred embodiment, Z comprises a heterocycloheptene moiety according to structure (Z37), which is optionally substituted. Preferably, the heterocycloheptyne moiety according to structure (Z37) is not substituted.

In a preferred embodiment, Z comprises a (hetero)cyclooctene moiety according to structure (Z8), more preferably according to (Z29), which is optionally substituted. Preferably, the cyclooctene moiety according to structure (Z8) or (Z29) is not substituted. In the context of the present embodiment, Z preferably comprises a (hetero)cyclooctene moiety according to structure (Z39) as shown below, wherein V is $(CH_2)_l$ and l is an integer in the range of 0 to 10, preferably in the range of 0 to 6. More preferably, l is 0, 1, 2, 3 or 4, more preferably l is 0, 1 or 2 and most preferably l is 0 or 1. In the context of group (Z39), l is most preferably 1. Most preferably, Z is according to structure (Z42), defined further below.

In an alternative preferred embodiment, Z comprises a (hetero)cyclooctene moiety according to structure (Z26), (Z27) or (Z28), which are optionally substituted. In the context of the present embodiment, Z preferably comprises a (hetero)cyclooctene moiety according to structure (Z40) or (Z41) as shown below, wherein $Y^1$ is O or $NR^{11}$, wherein $R^{11}$ is independently selected from the group consisting of hydrogen, a linear or branched $C_1$-$C_{12}$ alkyl group or a $C_4$-$C_{12}$ (hetero)aryl group. The aromatic rings in (Z40) are optionally O-sulfonylated at one or more positions, whereas the rings of (Z41) may be halogenated at one or more positions. Preferably, the (hetero)cyclooctene moiety according to structure (Z40) or (Z41) is not further substituted. Most preferably, Z is according to structure (Z43), defined further below.

In an alternative preferred embodiment, Z comprises a heterocycloheptenyl group and is according to structure (Z37).

(Z37)

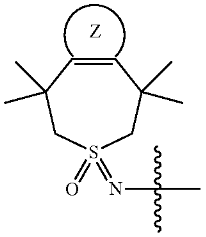

(Z39)

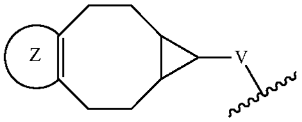

(Z40)

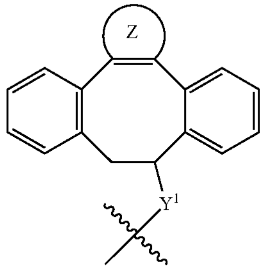

(Z41)

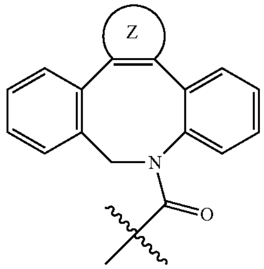

In an especially preferred embodiment, Z comprises a cyclooctenyl group and is according to structure (Z42):

(Z42)

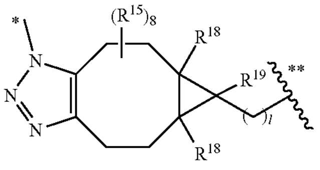

Herein:

the bond labelled with * is connected to S and the wavy bond labelled with ** is connected to L;

$R^{15}$ is independently selected from the group consisting of hydrogen, halogen, —$OR^{16}$, —$NO_2$, —CN, —$S(O)_2R^{16}$, —$S(O)_3^{(-)}$, $C_1$-$C_{24}$ alkyl groups, $C_5$-$C_{24}$ (hetero)aryl groups, $C_7$-$C_{24}$ alkyl(hetero)aryl groups and $C_7$-$C_{24}$ (hetero)arylalkyl groups and wherein the alkyl groups, (hetero)aryl groups, alkyl(hetero)aryl groups and (hetero)arylalkyl groups are optionally substituted, wherein two substituents $R^{15}$ may be linked together to form an optionally substituted annulated cycloalkyl or an optionally substituted annulated (hetero)arene substituent, and wherein $R^{16}$ is independently selected from the group consisting of hydrogen, halogen, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero) arylalkyl groups;

$R^{18}$ is independently selected from the group consisting of hydrogen, halogen, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups;

$R^{19}$ is selected from the group consisting of hydrogen, halogen, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups, the alkyl groups optionally being interrupted by one of more hetero-atoms selected from the group consisting of O, N and S, wherein the alkyl groups, (hetero)aryl groups, alkyl(hetero)aryl groups and (hetero)arylalkyl groups are independently optionally substituted, or $R^{19}$ is a second occurrence of Z (or Q) or D connected via a spacer moiety; and l is an integer in the range 0 to 10.

In a preferred embodiment of the group according to structure (Z42), $R^{15}$ is independently selected from the group consisting of hydrogen, halogen, —$OR^{16}$, $C_1$-$C_6$ alkyl groups, $C_5$-$C_6$ (hetero)aryl groups, wherein $R^{16}$ is hydrogen or $C_1$-$C_6$ alkyl, more preferably $R^{15}$ is independently selected from the group consisting of hydrogen and $C_1$-$C_6$ alkyl, most preferably all $R^{15}$ are H. In a preferred embodiment of the group according to structure (Z42), $R^{18}$ is independently selected from the group consisting of hydrogen, $C_1$-$C_6$ alkyl groups, most preferably both $R^{18}$ are H. In a preferred embodiment of the group according to structure (Z42), $R^{19}$ is H. In a preferred embodiment of the group according to structure (Z42), l is 0 or 1, more preferably l is 1.

In an especially preferred embodiment, Z comprises a (hetero)cyclooctynyl group and is according to structure (Z43):

(Z43)

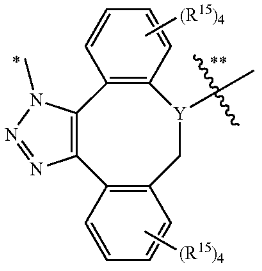

Herein:

the bond labelled with * is connected to S and the wavy bond labelled with ** is connected to L;

$R^{15}$ is independently selected from the group consisting of hydrogen, halogen, —$OR^{16}$, —$NO_2$, —CN, —$S(O)_2R^{16}$, —$S(O)_3^{(-)}$, $C_1$-$C_{24}$ alkyl groups, $C_5$-$C_{24}$ (hetero)aryl groups, $C_7$-$C_{24}$ alkyl(hetero)aryl groups and $C_7$-$C_{24}$ (hetero)arylalkyl groups and wherein the alkyl groups, (hetero)aryl groups, alkyl(hetero)aryl groups and (hetero)arylalkyl groups are optionally substituted, wherein two substituents $R^{15}$ may be linked together to form an optionally substituted annulated cycloalkyl or an optionally substituted annulated (hetero)arene substituent, and wherein $R^{16}$ is independently selected from the group consisting of hydrogen, halogen, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero) arylalkyl groups;

Y is N or $CR^{15}$.

In a preferred embodiment of the group according to structure (Z43), $R^{15}$ is independently selected from the group consisting of hydrogen, halogen, —$OR^{16}$, —$S(O)_3^{(-)}$, $C_1$-$C_6$ alkyl groups, $C_5$-$C_6$ (hetero)aryl groups, wherein $R^{16}$ is hydrogen or $C_1$-$C_6$ alkyl, more preferably $R^{15}$ is independently selected from the group consisting of hydrogen and —$S(O)_3^{(-)}$. In a preferred embodiment of the group according to structure (Z43), Y is N or CH, more preferably Y═N.

In an especially preferred embodiment, Z comprises a heterocycloheptynyl group and is according to structure (Z37) or (Z38a), preferably according to structure (Z37), wherein ring Z is a triazole.

(Z37)

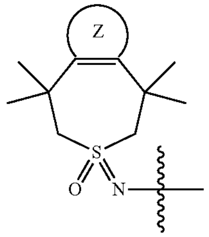

(Z38a)

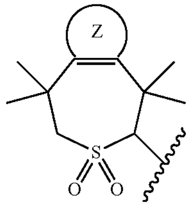

In an alternative preferred embodiment, Z comprises a (hetero)cycloalkane moiety, i.e. the bond depicted as - - - is a single bond. The (hetero)cycloalkane group may also be referred to as a heterocycloalkanyl group or a cycloalkanyl group, preferably a cycloalkanyl group, wherein the (hetero)cycloalkanyl group is optionally substituted. Preferably, the (hetero)cycloalkanyl group is a (hetero)cyclopropanyl group, a (hetero)cyclobutanyl group, a norbornane group, a norbornene group, a (hetero)cycloheptanyl group, a (hetero)cyclooctanyl group, a (hetero)cyclononyl group or a (hetero)cyclodecanyl group, which may all optionally be substituted. Especially preferred are (hetero)cyclopropanyl groups, (hetero)cycloheptanyl group or (hetero)cyclooctanyl groups, wherein the (hetero)cyclopropanyl group, the trans-(hetero)cycloheptanyl group or the (hetero)cyclooctanyl group is optionally substituted. Preferably, Z comprises a cyclopropanyl moiety according to structure (Z44), a hetereocyclobutane moiety according to structure (Z45), a norbornane or norbornene group according to structure (Z46), a (hetero)cycloheptanyl moiety according to structure (Z47) or a (hetero)cyclooctanyl moiety according to structure (Z48). Herein, $Y^3$ is selected from $C(R^{23})_2$, $NR^{23}$ or O, wherein each $R^{23}$ is individually hydrogen, $C_1$-$C_6$ alkyl or is connected to L, optionally via a spacer, and the bond labelled - - - is a single or double bond. In a further preferred embodiment, the cyclopropanyl group is according to structure (Z49). In another preferred embodiment, the (hetero)cycloheptane group is according to structure (Z50) or (Z51). In another preferred embodiment, the (hetero)cyclooctane group is according to structure (Z52), (Z53), (Z54), (Z55) or (Z56).

(Z44)

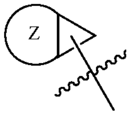

(Z45)

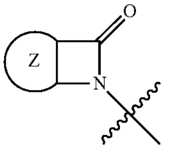

(Z46)

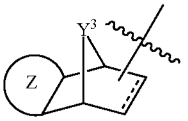

(Z47)

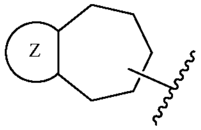

(Z48)

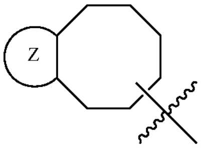

(Z49)

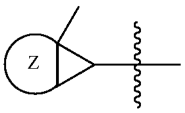

-continued (Z50)

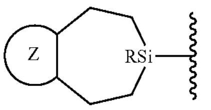

(Z51)

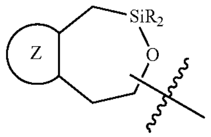

(Z52)

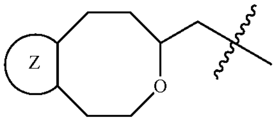

(Z53)

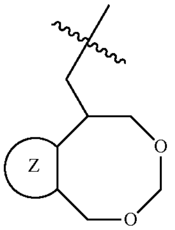

(Z54)

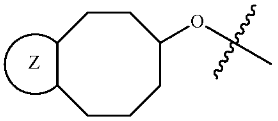

(Z55)

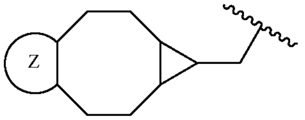

(Z56)

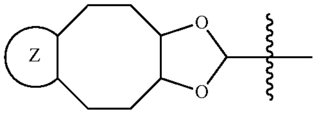

Herein, the R group(s) on Si in (Z50) and (Z51) are typically alkyl or aryl, preferably $C_1$-$C_6$ alkyl. Ring Z is typically selected from structures (Zn)-(Zu), wherein the carbon atoms labelled with ** correspond to the two carbon atoms of the (hetero)cycloalkane ring of (Z44)-(Z56) to which ring Z is fused, and the carbon a carbon labelled with * is directly connected to the peptide chain of the antibody. Preferred rings Z are selected from (Zo)-(Zr). Since the connecting group Z is formed by reaction with a (hetero) cycloalkene in the context of the present embodiment, the bound depicted above as - - - is a single bond.

(Zn)

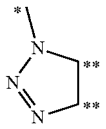

-continued (Zo)

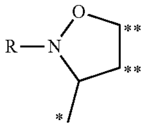

(Zp)

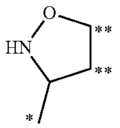

(Zq)

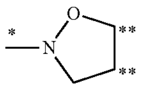

(Zr)

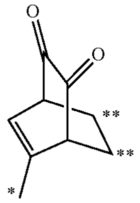

(Zs)

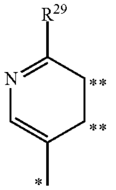

(Zt)

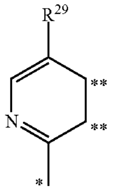

(Zu)

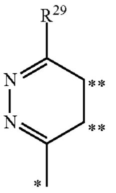

In a second preferred embodiment, Z is formed by a nucleophilic reaction, preferably by a nucleophilic substitution or a Michael addition, preferably by a Michael addition. A preferred Michael reaction is the thiol-maleimide ligation, most preferably wherein Q is maleimide and F is a thiol group. Preferably, the thiol is present in the sidechain of a cysteine residue. In a preferred embodiment, connection group Z comprises a succinimidyl ring or its ring-opened succinic acid amide derivative. Preferred options for connection group Z comprise a moiety selected from (Z57)-(Z71) depicted here below.

(Z57)

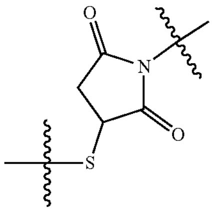

(Z58)

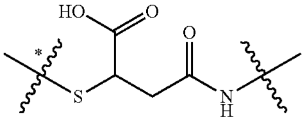

(Z59)

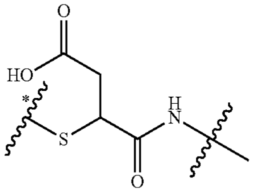

(Z60)

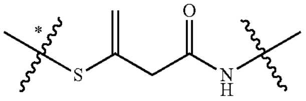

(Z61)

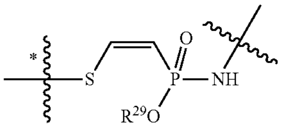

(Z61)

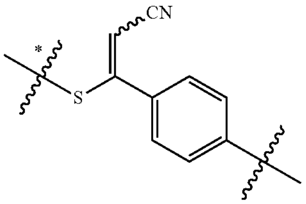

(Z63)

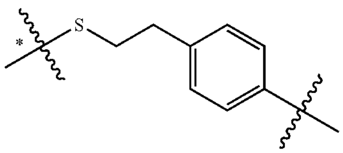

(Z64)

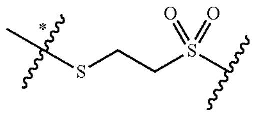

(Z65)

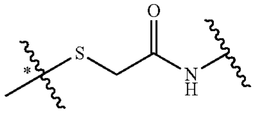

(Z66)

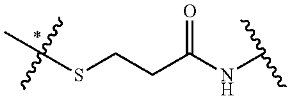

-continued (Z67)

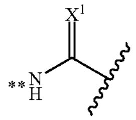

(Z68)

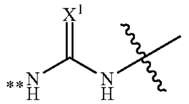

(Z69)

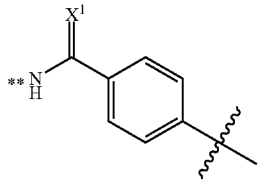

(Z70)

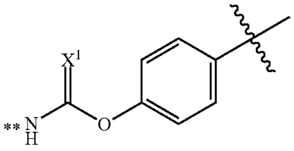

(Z71)

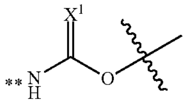

Herein, the wavy bond(s) labelled with an * is connected to the antibody Ab, optionally via a linker, and the wavy bond without label to the payload, optionally via a linker. In addition, $R^{29}$ is $C_{1-12}$ alkyl, preferably $C_{1-4}$ alkyl, most preferably ethyl, and $X^1$ is O or S, preferably $X^1$═O. The nitrogen atom labelled with ** in (Z67)-(Z71) corresponds to the nitrogen atom of the side chain of a lysine residue of the antibody. The carbon atoms of the phenyl group of (Z69) and (Z70) are optionally substituted, preferably optionally fluorinated.

In a preferred embodiment, connection group Z comprise a moiety selected from (Z1)-(Z71).

Linker L

Linker L connects payload D with connecting group Z (in the conjugate according to structure (1)) or connects payload D with reactive group Q (in the compound according to structure (2)). Linkers are known in the art and may be cleavable or non-cleabvale. Linker L preferably contains a self-immolative group or cleavable linker, comprising a peptide spacer and a para-aminobenzyloxycarbonyl (PABC) moiety or derivative thereof.

In a preferred embodiment, linker L as the structure $-(L^1)_n-(L^2)_o-(L^3)_p-(L^4)_q-$, wherein $(L^4)_q$ is connect to payload D and $(L^1)_n$ is connected to Z or Q. Herein $L^1$, $L^2$, $L^3$ and $L^4$ are linkers or linking units and each of n, o, p and q are individually 0 or 1, wherein n+o+p+q is at least 1. In a preferred embodiment, at least linkers $L^1$ and $L^2$ are present (i.e. n=1; o=1; p=0 or 1; q=0 or 1), more preferably linkers $L^1$, $L^2$ and $L^3$ are present and $L^4$ is either present or not (i.e. n=1; o=1; p=1; q=0 or 1). In one embodiment, linkers $L^1$, $L^2$, $L^3$ and $L^4$ are present (i.e. n=1; o=1; p=1; q=1). In one embodiment, linkers $L^1$, $L^2$ and $L^3$ are present and $L^4$ is not (i.e. n=1; o=1; p=1; q=0).

A linker, especially linker $L^1$, may contain one or more branch-points for attachment of multiple payloads to a single connecting group. In a preferred embodiment, the linker of the conjugate according to the invention contains a branching moiety. A "branching moiety" in the context of the present invention refers to a moiety that is embedded in a linker connecting three moieties. In other words, the branching moiety comprises at least three bonds to other moieties, typically one bond connecting to Z or Q, one bond to the payload D and one bond to a second payload D. The branching moiety, if present, is preferably embedded in linker $L^1$, more preferably part of $Sp^2$ or as the nitrogen atom of $NR^{13}$. Any moiety that contains at least three bonds to other moieties is suitable as branching moiety in the context of the present invention. In a preferred embodiment, the branching moiety is selected from a carbon atom, a nitrogen atom, a phosphorus atom, a (hetero)aromatic ring, a (hetero) cycle or a polycyclic moiety. Most preferably, the branching moiety is a nitrogen atom.

Linker $L^1$

Linker $L^1$ is either absent (n=0) or present (n=1). Preferably, linker $L^1$ is present and n=1. $L^1$ may for example be selected from the group consisting of linear or branched $C_1$-$C_{200}$ alkylene groups, $C_2$-$C_{200}$ alkenylene groups, $C_2$-$C_{200}$ alkynylene groups, $C_3$-$C_{200}$ cycloalkylene groups, $C_5$-$C_{200}$ cycloalkenylene groups, $C_8$-$C_{200}$ cycloalkynylene groups, $C_7$-$C_{200}$ alkylarylene groups, $C_7$-$C_{200}$ arylalkylene groups, $C_8$-$C_{200}$ arylalkenylene groups, $C_9$-$C_{200}$ arylalkynylene groups. Optionally the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups may be substituted, and optionally said groups may be interrupted by one or more heteroatoms, preferably 1 to 100 heteroatoms, said heteroatoms preferably being selected from the group consisting of O, $S(O)_{y'}$ and $NR^{21}$, wherein y' is 0, 1 or 2, preferably y'=2, and $R^{21}$ is independently selected from the group consisting of hydrogen, halogen, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero) arylalkyl groups.

In a preferred embodiment, linker $L^1$ contains a polar group. Such a polar group may be selected from (poly) ethylene glycoldiamines (e.g. 1,8-diamino-3,6-dioxaoctane or equivalents comprising longer ethylene glycol chains), (poly)ethylene glycol or (poly)ethylene oxide chains, (poly) propylene glycol or (poly)propylene oxide chains and 1,z'-diaminoalkanes (wherein z' is the number of carbon atoms in the alkane, preferably z'=1-10), $—(O)_a—C(O)—NH—S(O)_2—NR^{13}—$ (as further defined below, see structure (23)), $—C(S(O)_3^{(-)})—$, $—C(C(O)_2^{(-)})—$, $—S(O)_2—$, $—P(O)_2)—$, $—O(CH_2CH_2O)_t—$, $—NR^{30}(CH_2CH_2NR^{30})_t—$, and the following two structures:

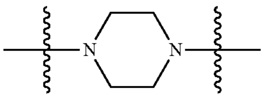

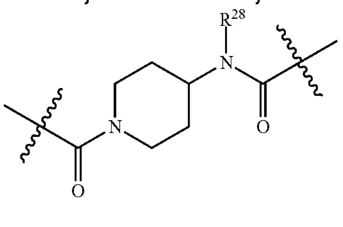

The polar group may also contain an amino acid, preferably selected from Arg, Glu, Asp, Ser and Thr. Herein, a and $R^{13}$ are further defined below for structure (23). t is an integer in the range of integer in the range of 0-15, preferably 1-10, more preferably 2-5, most preferably t=2 or 4. Each $R^{30}$ is individually H, $C_{1-12}$ alkyl, $C_{1-12}$ aryl, $C_{1-12}$ alkaryl or $C_{1-12}$ aralkyl. Linker $L^1$ may contain more than one such polar group, such as at least two polar groups. The polar group may also be present in a branch of linker $L^1$, which branches off a branching moiety as defined elsewhere. Preferable, a nitrogen or carbon atom is used as branching moiety. It is especially preferred to have a $-O(CH_2CH_2O)_t-$ polar group present in a branch.

In a preferred embodiment, Linker $L^1$ is or comprises a sulfamide group, preferably a sulfamide group according to structure (23):

(23)

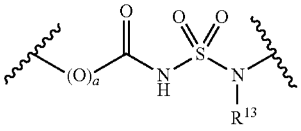

The wavy lines represent the connection to the remainder of the compound, typically to Q and $L^2$, $L^3$, $L^4$ or D, preferably to Q and $L^2$. Preferably, the $(O)_aC(O)$ moiety is connected to Q and the $NR^{13}$ moiety to $L^2$, $L^3$, $L^4$ or D, preferably to $L^2$.

In structure (23), a=0 or 1, preferably a=1, and $R^{13}$ is selected from the group consisting of hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups optionally substituted and optionally interrupted by one or more heteroatoms selected from O, S and $NR^{14}$ wherein $R^{14}$ is independently selected from the group consisting of hydrogen and $C_1$-$C_4$ alkyl groups, or $R^{13}$ is D connected to N via a spacer moiety, preferably $Sp^2$ as defined below, in one embodiment D is connected to N via $-(B)_e-(A)_f-(B)_g-C(O)-$.

In a preferred embodiment, $R^{13}$ is hydrogen or a $C_1$-$C_{20}$ alkyl group, more preferably $R^{13}$ is hydrogen or a $C_1$-$C_{16}$ alkyl group, even more preferably $R^{13}$ is hydrogen or a $C_1$-$C_{10}$ alkyl group, wherein the alkyl group is optionally substituted and optionally interrupted by one or more heteroatoms selected from O, S and $NR^{14}$, preferably O, wherein $R^{14}$ is independently selected from the group consisting of hydrogen and $C_1$-$C_4$ alkyl groups. In a preferred embodiment, $R^{13}$ is hydrogen. In another preferred embodiment, $R^{13}$ is a $C_1$-$C_{20}$ alkyl group, more preferably a $C_1$-$C_{16}$ alkyl group, even more preferably a $C_1$-$C_{10}$ alkyl group, wherein the alkyl group is optionally interrupted by one or more O-atoms, and wherein the alkyl group is optionally substituted with an —OH group, preferably a terminal —OH group. In this embodiment it is further preferred that $R^{13}$ is a (poly)ethylene glycol chain comprising a terminal —OH group. In another preferred embodiment, $R^{13}$ is selected from the group consisting of hydrogen, methyl, ethyl, n-propyl, i-propyl, n-butyl, s-butyl and t-butyl, more preferably from the group consisting of hydrogen, methyl, ethyl, n-propyl and i-propyl, and even more preferably from the group consisting of hydrogen, methyl and ethyl. Yet even more preferably, $R^{13}$ is hydrogen or methyl, and most preferably $R^{13}$ is hydrogen.

In a preferred embodiment, $L^1$ is according to structure (24):

(24)

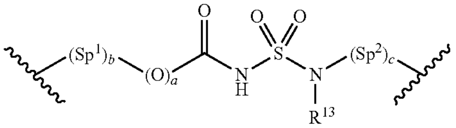

Herein, a and $R^{13}$ are as defined above, $Sp^1$ and $Sp^2$ are independently spacer moieties and b and c are independently 0 or 1. Preferably, b=0 or 1 and c=1, more preferably b=0 and c=1. In one embodiment, spacers $Sp^1$ and $Sp^2$ are independently selected from the group consisting of linear or branched $C_1$-$C_{200}$ alkylene groups, $C_2$-$C_{200}$ alkenylene groups, $C_2$-$C_{200}$ alkynylene groups, $C_3$-$C_{200}$ cycloalkylene groups, $C_5$-$C_{200}$ cycloalkenylene groups, $C_8$-$C_{200}$ cycloalkynylene groups, $C_7$-$C_{200}$ alkylarylene groups, $C_7$-$C_{200}$ arylalkylene groups, $C_8$-$C_{200}$ arylalkenylene groups and $C_9$-$C_{200}$ arylalkynylene groups, the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups being optionally substituted and optionally interrupted by one or more heteroatoms selected from the group of O, S and $NR^{16}$, wherein $R^{16}$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted. When the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups are interrupted by one or more heteroatoms as defined above, it is preferred that said groups are interrupted by one or more O-atoms, and/or by one or more S—S groups.

More preferably, spacer moieties $Sp^1$ and $Sp^2$, if present, are independently selected from the group consisting of linear or branched $C_1$-$C_{100}$ alkylene groups, $C_2$-$C_{100}$ alkenylene groups, $C_2$-$C_{100}$ alkynylene groups, $C_3$-$C_{100}$ cycloalkylene groups, $C_5$-$C_{100}$ cycloalkenylene groups, $C_8$-$C_{100}$ cycloalkynylene groups, $C_7$-$C_{100}$ alkylarylene groups, $C_7$-$C_{100}$ arylalkylene groups, $C_8$-$C_{100}$ arylalkenylene groups and $C_9$-$C_{100}$ arylalkynylene groups, the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups being optionally substituted and optionally interrupted by one or more heteroatoms selected from the group of O, S and $NR^{16}$, wherein $R^{16}$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted.

Even more preferably, spacer moieties $Sp^1$ and $Sp^2$, if present, are independently selected from the group consisting of linear or branched $C_1$-$C_{50}$ alkylene groups, $C_2$-$C_{50}$ alkenylene groups, $C_2$-$C_{50}$ alkynylene groups, $C_3$-$C_{50}$ cycloalkylene groups, $C_5$-$C_{50}$ cycloalkenylene groups, $C_8$-$C_{50}$ cycloalkynylene groups, $C_7$-$C_{50}$ alkylarylene groups, $C_7$-$C_{50}$ arylalkylene groups, $C_8$-$C_{50}$ arylalkenylene groups and $C_9$-$C_{50}$ arylalkynylene groups, the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups being optionally substituted and optionally interrupted by one or more heteroatoms selected from the group of O, S and $NR^{16}$, wherein $R^{16}$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted.

Yet even more preferably, spacer moieties $Sp^1$ and $Sp^2$, if present, are independently selected from the group consisting of linear or branched $C_1$-$C_{20}$ alkylene groups, $C_2$-$C_{20}$ alkenylene groups, $C_2$-$C_{20}$ alkynylene groups, $C_3$-$C_{20}$ cycloalkylene groups, $C_5$-$C_{20}$ cycloalkenylene groups, $C_8$-$C_{20}$ cycloalkynylene groups, $C_7$-$C_{20}$ alkylarylene groups, $C_7$-$C_{20}$ arylalkylene groups, $C_8$-$C_{20}$ arylalkenylene groups and $C_9$-$C_{20}$ arylalkynylene groups, the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups being optionally substituted and optionally interrupted by one or more heteroatoms selected from the group of O, S and $NR^{16}$, wherein $R^{16}$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted.

In these preferred embodiments it is further preferred that the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups are unsubstituted and optionally interrupted by one or more heteroatoms selected from the group of O, S and $NR^{16}$, preferably O, wherein $R^{16}$ is independently selected from the group consisting of hydrogen and $C_1$-$C_4$ alkyl groups, preferably hydrogen or methyl.

Most preferably, spacer moieties $Sp^1$ and $Sp^2$, if present, are independently selected from the group consisting of linear or branched $C_1$-$C_{20}$ alkylene groups, the alkylene groups being optionally substituted and optionally interrupted by one or more heteroatoms selected from the group of O, S and $NR^{16}$, wherein $R^{16}$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted. In this embodiment, it is further preferred that the alkylene groups are unsubstituted and optionally interrupted by one or more heteroatoms selected from the group of O, S and $NR^{16}$, preferably O and/or S—S, wherein $R^{16}$ is independently selected from the group consisting of hydrogen and $C_1$-$C_4$ alkyl groups, preferably hydrogen or methyl.

Preferred spacer moieties $Sp^1$ and $Sp^2$ thus include $-(CH_2)_r-$, $-(CH_2CH_2)_r-$, $-(CH_2CH_2O)_r-$, $-(OCH_2CH_2)_r-$, $-(CH_2CH_2O)_rCH_2CH_2-$, $-CH_2CH_2(OCH_2CH_2)_r-$, $-(CH_2CH_2CH_2O)_r-$, $-(OCH_2CH_2CH_2)_r-$, $-(CH_2CH_2CH_2O)_rCH_2CH_2CH_2-$ and $-CH_2CH_2CH_2(OCH_2CH_2CH_2)_r-$, wherein r is an integer in the range of 1 to 50, preferably in the range of 1 to 40, more preferably in the range of 1 to 30, even more preferably in the range of 1 to 20 and yet even more preferably in the range of 1 to 15. More preferably n is 1, 2, 3, 4, 5, 6, 7, 8, 9 or 10, more preferably 1, 2, 3, 4, 5, 6, 7 or 8, even more preferably 1, 2, 3, 4, 5 or 6, yet even more preferably 1, 2, 3 or 4.

Alternatively, preferred linkers $L^1$ may be represented by $-(W)_k-(A)_d-(B)_e-(A)_f-(C(O))_g-$, wherein:

- d=0 or 1, preferably d=1;
- e=an integer in the range 0-10, preferably e=0, 1, 2, 3, 4, 5 or 6, preferably an integer in the range 1-10, most preferably e=1, 2, 3 or 4;
- f=0 or 1, preferably f=0;
- wherein d+e+f is at least 1, preferably in the range 1-5; and preferably wherein d+f is at least 1, preferably d+f=1.
- g=0 or 1, preferably g=1;
- k=0 or 1, preferably k=1;
- A is a sulfamide group according to structure (23);
- B is a $-CH_2-CH_2-O-$ or a $-O-CH_2-CH_2-$ moiety, or $(B)_e$ is a $-(CH_2-CH_2-O)_{e1}-CH_2-CH_2-$ or a $-(CH_2-CH_2-O)_{e1}-CH_2-$ moiety, wherein e1 is defined the same way as e;
- W is $-OC(O)-$, $-C(O)O-$, $-C(O)NH-$, $-NHC(O)-$, $-OC(O)NH-$, $-NHC(O)O-$, $-C(O)(CH_2)_mC(O)-$, $-C(O)(CH_2)_mC(O)NH-$ or -(4-Ph)$CH_2NHC(O)(CH_2)_mC(O)NH-$, preferably wherein W is $-OC(O)NH-$, $-C(O)(CH_2)_mC(O)NH-$ or $-C(O)NH-$, and wherein m is an integer in the range 0-10, preferably m=0, 1, 2, 3, 4, 5 or 6, most preferably m=2 or 3;
- preferably wherein $L^1$ is connected to Q via $(W)_k$ and to $L^2$, $L^3$, $L^4$ or D, preferably to $L^2$, via $(C(O))_g$, preferably via C(O).

In the context of the present embodiment, the wavy lines in structure (23) represent the connection to the adjacent groups such as $(W)_k$, $(B)_e$ and $(C(O))_g$. It is preferred that A is according to structure (23), wherein a=1 and $R^{13}$=H or a $C_1$-$C_{20}$ alkyl group, more preferably $R^{13}$=H or methyl, most preferably $R^{13}$=H.

Preferred linkers $L^1$ have structure $-(W)_k-(A)_d-(B)_e-(A)_r-(C(O))_g-$, wherein:

(a) k=0; d=1; g=1; f=0; B=$-CH_2-CH_2-O-$; e=1, 2, 3 or 4, preferably e=2.
(b) k=1; W=$-C(O)(CH_2)_mC(O)NH-$; m=2; d=0; $(B)_e$=$-(CH_2-CH_2-O)_{e1}-CH_2-CH_2-$; f=0; g=1; e1=1, 2, 3 or 4, preferably e=1.
(c) k=1; W=$-OC(O)NH-$; d=0; B=$-CH_2-CH_2-O-$; g=1; f=0; e=1, 2, 3 or 4, preferably e=2.
(d) k=1; W=$-C(O)(CH_2)_mC(O)NH-$; m=2; d=0; $(B)_e$=$-(CH_2-CH_2-O)_{e1}-CH_2-CH_2-$; f=0; g=1; e1=1, 2, 3 or 4, preferably e1=4.
(e) k=1; W=$-OC(O)NH-$; d=0; $(B)_e$=$-(CH_2-CH_2-O)_{e1}-CH_2-CH_2-$; g=1; f=0; e1=1, 2, 3 or 4, preferably e1=4.
(f) k=1; W=-(4-Ph)$CH_2NHC(O)(CH_2)_mC(O)NH-$, m=3; d=0; $(B)_e$=$-(CH_2-CH_2-O)_{e1}-CH_2-CH_2-$; g=1; f=0; e1=1, 2, 3 or 4, preferably e1=4.
(g) k=0; d=0; g=1; f=0; B=$-CH_2-CH_2-O-$; e=1, 2, 3 or 4, preferably e=2.
(h) k=1; W=$-C(O)NH-$; d=0; g=1; f=0; B=$-CH_2-CH_2-O-$; e=1, 2, 3 or 4, preferably e=2.

In a preferred embodiment, linker $L^1$ comprises a branching nitrogen atom, which is located in the backbone between Q or Z and $(L^2)_o$ and which contains a further moiety D as substituent, which is preferably linked to the branching nitrogen atom via a linker. An example of a branching nitrogen atom is the nitrogen atom $NR^{13}$ in structure (23), wherein $R^{13}$ is connected to a second occurrence of D via a spacer moiety. Alternatively, a branching nitrogen atoms may be located within $L^1$ according to structure $—(W)_k-(A)_d-(B)_e-(A)_f-(C(O))_g—$. In one embodiment, $L^1$ is represented by $—(W)_k-(A)_d-(B)_e-(A)-(C(O))_g—N^*[-(A)_{d'}-(B)_{e'}-(A)_{f'}-(C(O))_{g'}-]2$, wherein A, B, W, d, e, f, g and k are as defined above and individually selected for each occurrence, and N* is the branching nitrogen atoms, to which two instances of $-(A)_{d'}-(B)_{e'}-(A)_{f'}-(C(O))_{g'}—$ are connected. Herein, both $(C(O))_{g'}$ moieties are connected to $-(L^2)_o-(L^3)_p-(L^4)_q$-D, wherein $L^2$, $L^3$, $L^4$, o, p, q and D are as defined above and are each selected individually. In a preferred embodiment, each of $L^2$, $L^3$, $L^4$, o, p, q and D are the same for both moieties connected to $(C(O))_{g'}$.

Preferred linkers $L^1$ comprising a branching nitrogen atom have structure $—(W)_k-(A)_d-(B)_e-(A)_f-(C(O))_g—N^*[-(A')_{d'}-(B')_{e'}-(A')_{f'}-(C(O))_{g'}-]2$ wherein:

(i) k=d=g=e'=1; f=d'=g'=0; W=—C(O)—; B=B'=—$CH_2$—$CH_2$—O—; A is according to structure (23) with a=0 and $R^{13}$=H; e=1, 2, 3 or 4, preferably e=2.

(j) k=d=g=e'=g'=1; f=d'=0; W=—C(O)—; B=B'=—$CH_2$—$CH_2$—O—; A is according to structure (23) with a=0 and $R^{13}$=H; e=1, 2, 3 or 4, preferably e=2.

Linker $L^2$

Linker $L^2$ is either absent (o=0) or present (o=1). Preferably, linker $L^2$ is present and o=1. Linker $L^2$ is a peptide spacer The peptide spacer is preferably defined by $(NH—CR^{17}—CO)_n$, wherein $R^{17}$ represents an amino acid side chain as known in the art. Herein, the amino acid may be a natural or a synthetic amino acid. Preferably, the amino acid(s) are all in their L-configuration. n is an integer in the range of 1-5, preferably in the range of 2-5. Thus, the peptide spacer preferably contains 1-5 amino acids. Preferably, the peptide is a dipeptide (n=2), tripeptide (n=3) or tetrapeptide (n=4), most preferably the peptide spacer is a dipeptide. Although any peptide spacer may be used, preferably the peptide spacer is selected from Val-Cit, Val-Ala, Val-Lys, Val-Arg, AcLys-Val-Cit, AcLys-Val-Ala, Glu-Val-Ala, Asp-Val-Ala, iGlu-Val-Ala, Glu-Val-Cit, Asp-Val-Cit, iGlu-Val-Cit, Phe-Cit, Phe-Ala, Phe-Lys, Phe-Arg, Ala-Lys, Leu-Cit, Ile-Cit, Trp-Cit, Ala-Ala-Asn, Ala-Asn, Gly-Gly-Phe-Gly and Lys, more preferably Val-Cit, Val-Ala, Glu-Val-Ala, Val-Lys, Phe-Cit, Phe-Ala, Phe-Lys, Ala-Ala-Asn, more preferably Val-Cit, Val-Ala, Ala-Ala-Asn, most preferably Val-Cit or Val-Ala. Herein, AcLys is acetyllysine and iGlu is isoglutamate. In one embodiment, $L^2$=Val-Cit. In one embodiment, $L^2$=Val-Ala.

$R^{17}$ represents the amino acid side chain, preferably selected from the side chains of alanine, cysteine, aspartic acid, glutamic acid, phenylalanine, glycine, histidine, isoleucine, lysine, acetyllysine, leucine, methionine, asparagine, pyrrolysine, proline, glutamine, arginine, serine, threonine, selenocysteine, valine, tryptophan, tyrosine and citrulline. Preferred amino acid side chains are those of Val, Cit, Ala, Lys, Arg, AcLys, Phe, Leu, lie, Trp, Glu, Asp and Asn, more preferably from the side chains of Val, Cit, Ala, Glu and Lys. Alternatively worded, $R^{17}$ is preferably selected from $CH_3$ (Ala), $CH_2CH(CH_3)_2$ (Leu), $CH_2CH_2CH_2NHC(O)NH_2$ (Cit), $CH_2CH_2CH_2CH_2NH_2$ (Lys), $CH_2CH_2CH_2NHC(O)CH_3$ (AcLys), $CH_2CH_2CH_2NHC(=NH)NH_2$ (Arg), $CH_2Ph$ (Phe), $CH(CH_3)_2$ (Val), $CH(CH_3)CH_2CH_3$ (Ile), $CH_2C(O)NH_2$ (Asn), $CH_2CH_2C(O)OH$ (Glu), $CH_2C(O)OH$ (Asp) and $CH_2$ (1H-indol-3-yl) (Trp). Especially preferred embodiments of $R^{17}$ are $CH_3$ (Ala), $CH_2CH_2CH_2NHC(O)NH_2$ (Cit), $CH_2CH_2CH_2CH_2NH_2$ (Lys), $CH_2CH_2C(O)OH$ (Glu) and $CH(CH_3)_2$ (Val). Most preferably, $R^{17}$ is $CH_3$ (Ala), $CH_2CH_2CH_2NHC(O)NH_2$ (Cit), $CH_2CH_2CH_2CH_2NH_2$ (Lys), or $CH(CH_3)_2$ (Val).

In an especially preferred embodiment, the peptide spacer may be represented by general structure (L3):

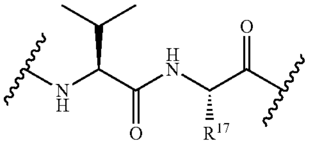

(L3)

Herein, $R^{17}$ is as defined above, preferably $R^{17}$ is $CH_3$ (Val) or $CH_2CH_2CH_2NHC(O)NH_2$ (Cit). The wavy lines indicate the connection to $(L^1)_n$ and $(L^3)_p$, preferably $L^2$ according to structure (L3) is connected to $(L^1)_n$ via NH and to $(L^3)_p$ via C(O).

Linker $L^3$

Linker $L^3$ is either absent (p=0) or present (p=1). Preferably, linker $L^3$ is present and p=1. Linker $L^3$ is a self-cleavable spacer, also referred to as self-immolative spacer. Preferably, $L^3$ is para-aminobenzyloxycarbonyl (PABC) derivative, more preferably a PABC derivative according to structure (L4):

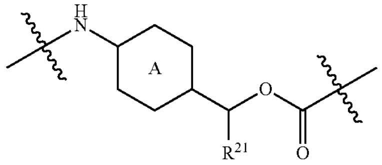

(L4)

Herein, the wavy lines indicate the connection to Q or Z, $L^1$ or $L^2$, and to $L^4$ or D. Typically, the PABC derivative is connected via NH to Q, Z, $L^1$ or $L^2$, preferably to $L^2$, and via O to $L^4$ or D.

A is a 5- or 6-membered aromatic or heteroaromatic ring, preferably a 6-membered aromatic or heteroaromatic ring. Suitable 5-membered rings are oxazole, thiazole and furan. Suitable 6-membered rings are phenyl and pyridyl. In a preferred embodiment, A is 1,4-phenyl, 2,5-pyridyl or 3,6-pyridyl. Most preferably, A is 1,4-phenyl.

$R^{21}$ is selected from H, $R^{26}$, C(O)OH and C(O)$R^{26}$, wherein $R^{26}$ is $C_1$-$C_{24}$ (hetero)alkyl groups, $C_3$-$C_{10}$ (hetero)cycloalkyl groups, $C_2$-$C_{10}$ (hetero)aryl groups, $C_3$-$C_{10}$ alkyl(hetero)aryl groups and $C_3$-$C_{10}$ (hetero)arylalkyl groups, which are optionally substituted and optionally interrupted by one or more heteroatoms selected from O, S and $NR^{28}$ wherein $R^{28}$ is independently selected from the group consisting of hydrogen and $C_1$-$C_4$ alkyl groups. Preferably, $R^{26}$ is $C_3$-$C_{10}$ (hetero)cycloalkyl or polyalkylene glycol. The polyalkylene glycol is preferably a polyethylene glycol or a polypropylene glycol, more preferably $—(CH_2CH_2O)_sH$ or $—(CH_2CH_2CH_2O)_sH$. The polyalkylene glycol is most preferably a polyethylene glycol, preferably $—(CH_2CH_2O)_sH$, wherein s is an integer in the range 1-10, preferably 1-5, most preferably s=1, 2, 3 or 4. More preferably, $R^{21}$ is H or C(O)$R^{26}$, wherein $R^{26}$=4-methyl-piperazine or morpholine. Most preferably, $R^{21}$ is H.

Linker $L^4$

Linker $L^4$ is either absent (q=0) or present (q=1). Preferably, linker $L^4$ is present and q=1. Linker $L^4$ is selected from:

an aminoalkanoic acid spacer according to the structure $—NR^{22}—(C_z\text{-alkylene})-C(O)—$, wherein z is an integer in the range 1-20 and $R^{22}$ is H or $C_1$-$C_4$ alkyl;

an ethyleneglycol spacer according to the structure $-NR^{22}-(CH_2-CH_2-O)_{e6}-(CH_2)_{e7}-C(O)-$, wherein e6 is an integer in the range 1-10, e7 is an integer in the range 1-3 and $R^{22}$ is H or $C_1$-$C_4$ alky; and an diamine spacer according to the structure $-NR^{22}-(C_z\text{-alkylene})-NR^{22}-(C(O))_h-$, wherein h is 0 or 1, z is an integer in the range 1-20 and $R^{22}$ is H or $C_1$-$C_4$ alkyl.

Linker $L^4$ may be an aminoalkanoic acid spacer, i.e. $-NR^{22}-(C_z\text{-alkylene})-C(O)-$, wherein z is an integer in the range 1 to 20, preferably 1-10, most preferably 1-6. Herein, the aminoalkanoic acid spacer is typically connected to $L^3$ via the nitrogen atom and to D via the carbonyl moiety. Preferred linkers $L^4$ are selected from 6-aminohexanoic acid (Ahx, z=5), β-alanine (z=2) and glycine (Gly, z=1), even more preferably 6-aminohexanoic acid or glycine. In one embodiment, $L^4$=6-aminohexanoic acid. In one embodiment, $L^4$=glycine. Herein, $R^{22}$ is H or $C_1$-$C_4$alkyl, preferably $R^{22}$ is H or methyl, most preferably $R^{22}$ is H.

Alternatively, linker $L^4$ may be an ethyleneglycol spacer according to the structure $-NR^{22}-(CH_2-CH_2-O)_{e6}-(CH_2)_{e7}-(C(O)-$, wherein e6 is an integer in the range 1-10, preferably e6 is in the range 2-6, and e7 is an integer in the range 1-3, preferably e7 is 2. Herein, $R^{22}$ is H or $C_1$-$C_4$ alkyl, preferably $R^{22}$ is H or methyl, most preferably $R^{22}$ is H.

Alternatively, linker $L^4$ may be a diamine spacer according to the structure $-NR^{22}-(C_z\text{-alkylene})-NR^{22}-(C(O))_h-$, wherein h is 0 or 1, z is an integer in the range 1-20, preferably an integer in the range 2-6, even more preferably z=2 or 5, most preferably z=2. $R^{22}$ is H or $C_1$-$C_4$ alkyl. Herein, $R^{22}$ is H or $C_1$-$C_4$ alkyl, preferably $R^{22}$ is H or methyl, most preferably $R^{22}$ is methyl. Herein, h is preferably 1, in which case linker $L^4$ is especially suited for conjugation via a phenolic hydroxyl group present on payload D.

Payload D

D represents the target molecule D that is or is to be connected to the antibody, which is also referred to in the art as the payload. D is selected from the group consisting of anthracyclines, camptothecins, tubulysins, enediynes, amanitins, duocarmycins, maytansinoids, auristatins, eribulins, BCL-XL inhibitors, hemiasterlins, KSP inhibitors, TLR agonists, indolinobenzodiazepine dimers or pyrrolobenzodiazepine dimers (PBDs), and analogues or prodrugs thereof. Alternatively, D is defined as a pharmaceutically active substance, such as an anti-cancer agent, preferably a cytotoxin. Preferably, D is selected from the group consisting of anthracyclines, camptothecins, maytansinoids, enediynes, amanitins, auristatins and pyrrolobenzodiazepine dimers, more preferably D is selected from the group consisting of enediynes, auristatins and camptothecins. In one embodiment, D is an enediyne. In one embodiment, D is an auristatin. In one embodiment, D is a camptothecin. Most preferably, D is a camptothecin.

Figure 6:
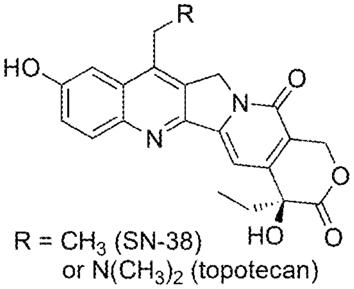
FIG. 6 shows the structures of various camptothecins, which are preferred payloads in the context of the present invention.
Figure 6:
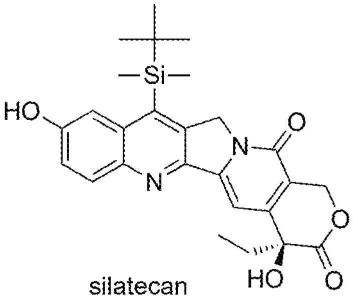
Figure 6:
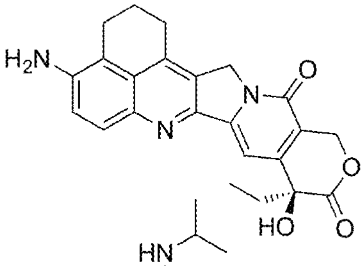
Figure 6:
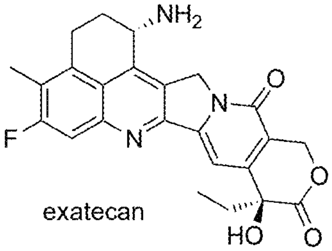
Figure 6:
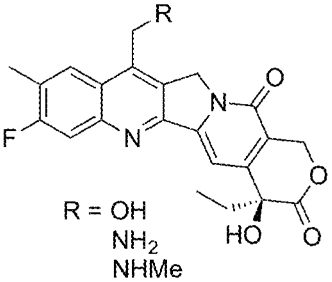
Figure 6:
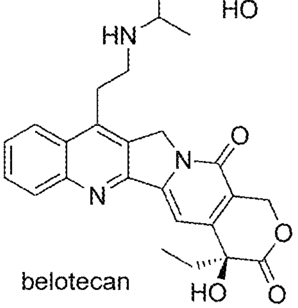
Figure 6:
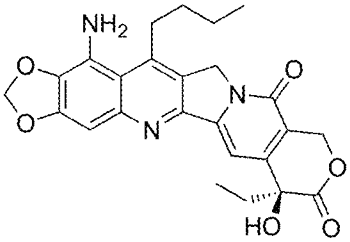
Figure 6:
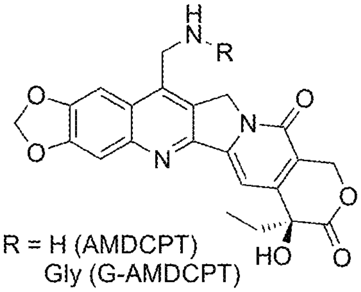
Figure 6:
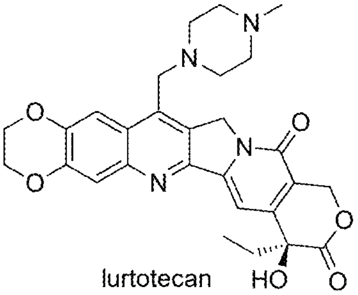
Figure 6:
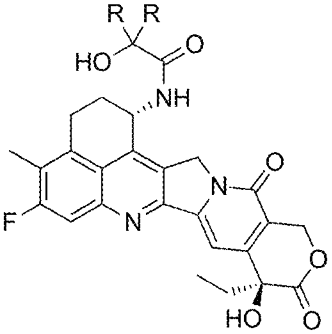
Figure 6:
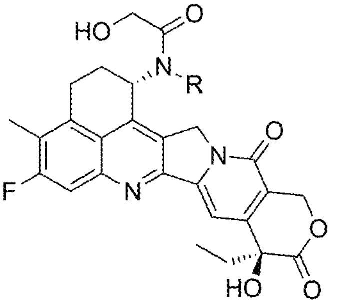
Figure 6:
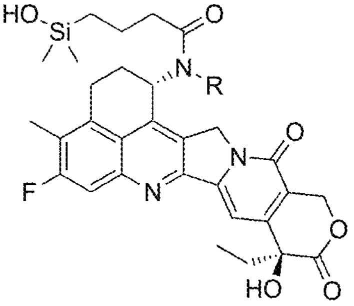
Figure 7:
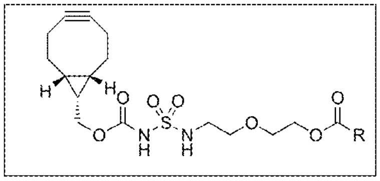
FIG. 7 depicts the structures of the BCN-linker drugs containing a Val-Cit-PABC or Val-Ala-PABC cleavable linker used to prepare ADCs via click chemistry to the azidosugar-remodeled antibodies, with the following payloads (3=exatecan, 4=MMAE, 5a=calicheamicin $g_1^I$, 5b=glycine-calicheamicin $g_1^I$, 6=6-aminohexanoyl-maytansinoid).
Figure 7:
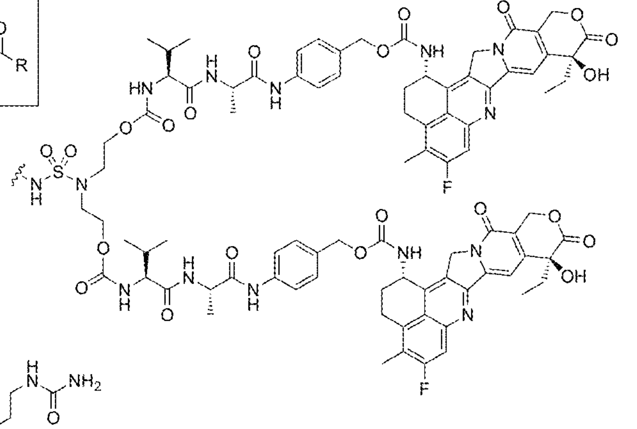
Figure 7:
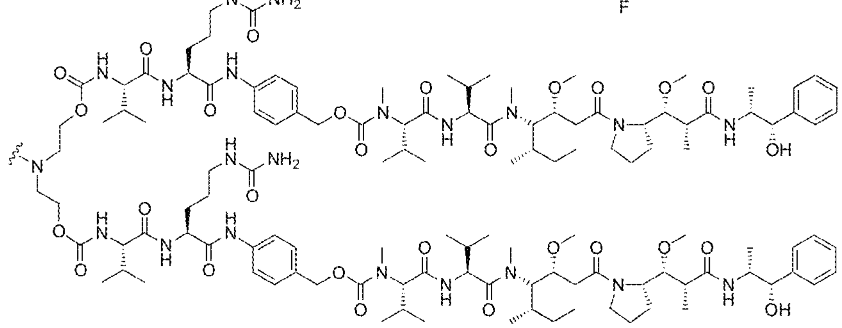
Figure 7:
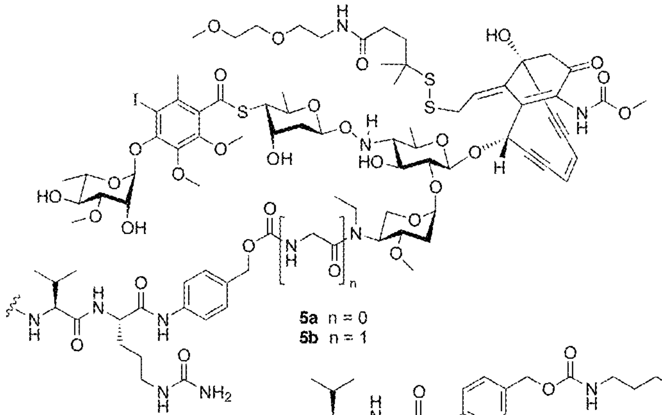
Figure 7:
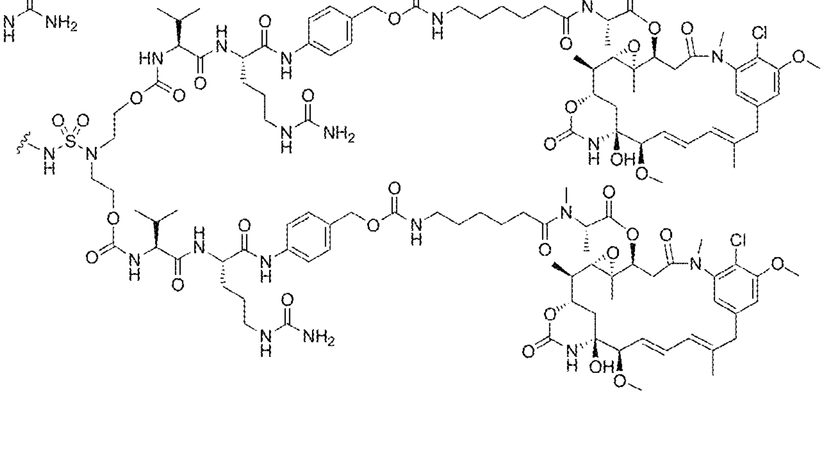
Figure 8:
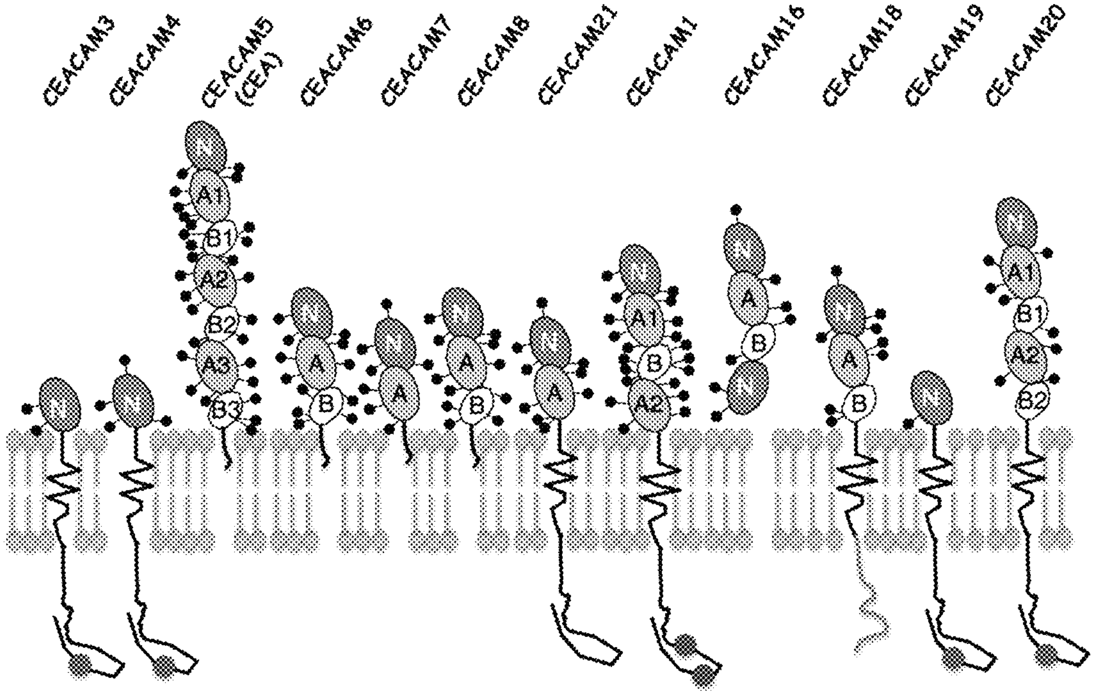
FIG. 8 shows the structures of twelve members of the human CEA family, which belong to the CEACAM subgroup. CEACAM-encoded proteins generally have one variable (V)-like Ig domain, identified as the N domain (except CEACAM16 with two N domains), but they differ in the number of constant C2-like Ig domains, identified as A or B, as well as the membrane anchorage.

In a preferred embodiment, the enediyne is selected from the group consisting of calicheamicins, esperamicins, shishijimicins and namenamicins, more preferably calicheamicin. In another preferred embodiment, the auristatin is selected from the group consisting of MMAD, MMAE, MMAF or PF-06380101, more preferably MMAE or PF-06380101. In another preferred embodiment, the camptothecin is selected from the compounds depicted in FIG. 6, preferably from the group consisting of topotecan, silatecan, cositecan, exatecan, exatecan-S, DXd, SN-38, lurtotecan, gimatecan, belotecan, rubitecan, AMDCPT and G-AMDCPT, more preferably exatecan or DXd, most preferably exatecan.

In an especially preferred embodiment, D is selected from the group consisting of calicheamicin, MMAE, PF-06380101, exatecan and DXd, more preferably from the group consisting of calicheamicin, MMAE, and exatecan, most preferably D is exatecan.

The compound according to general structure (2) may comprise more than one moiety D. When more than one cytotoxin D is present the cytotoxins D may be the same or different, typically they are the same. In a preferred embodiment, the compound according to general structure (2) contains 1 or 2 occurrences of D, most preferably 2 occurrence of D. Typically, the second occurrence of D is present within linker L, which may contain a branching moiety, typically a branching nitrogen atom, that is connected to the second occurrence of D. Preferably, both occurrences of D are connected to the branching moiety via the same linker. Likewise, the antibody-conjugate according to structure (1) may contain more than one moiety D per connecting group Z.

Preferred Antibody-Conjugates

Preferred antibody-conjugates according to the first aspect are selected from the group consisting of compounds (I)-(III), more preferably (II) or (III), most preferably (II). More preferred antibody-conjugates are selected from (X)-(XIII). In one especially preferred embodiment, the antibody-conjugates is selected from (Xa), (XIb), (XIIg), (XIIh) and (XIIIe). In an even more preferred embodiment, the antibody-conjugates is selected from (XI) and (XIII), more preferably (XIb) or (XIIIe), more preferably the antibody-conjugates is according to (XIII), most preferably according to (XIIIe). The structures of these antibody-conjugates are defined here below.

Antibody-conjugate (I) has the following structure:

$$AB\text{-}[(L^6)\text{-}\{Z\text{-}(L^1)\text{-}(L^2)\text{-}(L^3)\text{-}(L^4)_q\text{-}D\}_x]_y \quad (I)$$

wherein:

AB, $L^6$, Z, D, x and y are as defined above;

$L^1$ is a linker represented by $-(A)_d-(B)_e-(A)_f-(C(O))_g-$, as defined above;

$L^2$ is Val-Cit or Val-Ala;

$L^3$ is the PABC derivative according to structure (L4);

$L^4$ is $-N-(C_z\text{-alkylene})-C(O)-$ or $-NR^{22}-(C_z\text{-alkylene})-NR^{22}-$, wherein z and $R^{22}$ are as defined above;

q=0 or 1.

In the context of antibody-conjugate (I), it is preferred that for $L^1$, d=1 (A according to structure (23), it is preferred that a=1 and $R^{13}$=H), e=2, f=0 and g=1. In the context of antibody-conjugate (1), it is preferred that $L^2$=Val-Cit. In the context of antibody-conjugate (I), it is preferred that for $L^3$, $R^{21}$=H. In the context of antibody-conjugate (I), it is preferred that in case q=1, then z=1 or 5.

In a particularly preferred embodiment, the antibody-conjugate according to structure (1) contains a payload D selected from the group consisting of calicheamicin, MMAE, PF-06380101, exatecan and DXd, more preferably a payload D selected from the group consisting of calicheamicin, MMAE, and exatecan, most preferably with exatecan as payload D.

Antibody-conjugate (II) has the following structure:

$$AB\text{-}[(L^6)\text{-}\{Z\text{-}(L^1)\text{-}(L^2)\text{-}(L^3)\text{-}D\}_x]_y \quad (II)$$

wherein:

AB, $L^6$, Z, D, x and y are as defined above;

$L^1$ is a linker represented by $-(A)-(B)_e-(C(O))-$, as defined above;

$L^2$ is Val-Cit or Val-Ala;

$L^3$ is the PABC derivative according to structure (L4), wherein $R^{21}$═H.

In the context of antibody-conjugate (II), it is preferred that for $L^1$, e=2, A according to structure (23), it is preferred that a=1 and $R^{13}$═H. In the context of antibody-conjugate (II), it is preferred that $L^2$=Val-Cit.

In a particularly preferred embodiment, the antibody-conjugate according to structure (II) contains a payload D selected from the group consisting of calicheamicin, MMAE, PF-06380101, exatecan and DXd, more preferably a payload D selected from the group consisting of calicheamicin, MMAE, and exatecan, most preferably with exatecan as payload D.

Antibody-conjugate (III) has the following structure:

$$AB\text{-}[(L^6)\text{-}\{Z\text{-}(L^1)\text{-}(L^2)\text{-}(L^3)\text{-}(L^4)\text{-}D\}_x]_y \quad \text{(III)}$$

wherein:

AB, $L^6$, Z, D, x and y are as defined above;

$L^1$ is a linker represented by -(A)-$(B)_e$—(C(O))—, as defined above;

$L^2$ is Val-Cit or Val-Ala;

$L^3$ is the PABC derivative according to structure (L4), wherein $R^{21}$═H;

$L^4$ is —$NR^{22}$—($C_z$-alkylene)-$NR^{22}$—, wherein $R^{22}$ is as defined above and z is an integer in the range 1 to 6.

In the context of antibody-conjugate (III), it is preferred that for $L^1$, e=2, and with a=1 and $R^{13}$═H. In the context of antibody-conjugate (III), it is preferred that $L^2$=Val-Cit. In the context of antibody-conjugate (III), it is preferred that z=2.

In a particularly preferred embodiment, the antibody-conjugate according to structure (III) contains a payload D selected from the group consisting of calicheamicin, MMAE, PF-06380101, exatecan and DXd, more preferably a payload D selected from the group consisting of calicheamicin, MMAE, and exatecan, most preferably with exatecan as payload D.

Antibody-conjugate (X) has a linker-payload moiety according to the following structure:

(X)

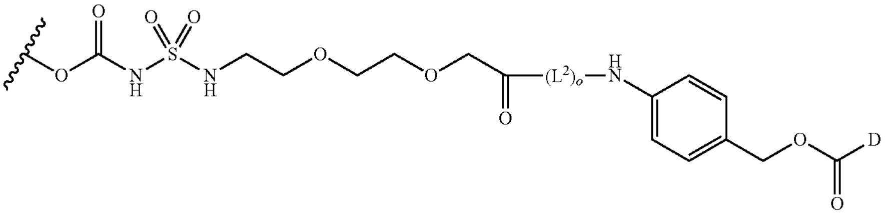

wherein:

the wavy line indicates the connection to Z;

$L^2$, o and D are as defined above.

$L^2$ may be present of absent, preferably $L^2$ is present and o=1. For preferred antibody-conjugate (Xa), $L^2$ is according to structure (L3) and $R^{17}$ is $CH_3$. For preferred antibody-conjugate (Xb), $L^2$ is according to structure (L3) and $R^{17}$ is $CH_2CH_2CH_2NHC(O)NH_2$. The antibody-conjugate (X) preferably has structure (Xa).

In a particularly preferred embodiment, the antibody-conjugate according to structure (X) contains a payload D selected from the group consisting of calicheamicin, MMAE, PF-06380101, exatecan and DXd, more preferably a payload D selected from the group consisting of calicheamicin, MMAE, and exatecan, most preferably with exatecan as payload D.

Antibody-conjugate (XI) has a linker-payload moiety according to the following structure:

(XI)

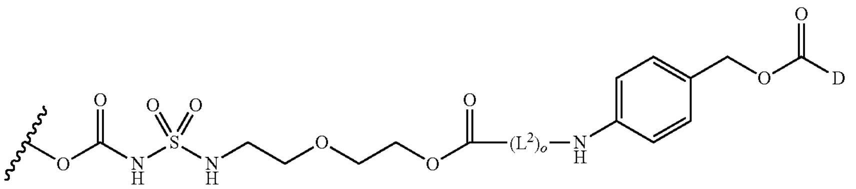

wherein:

the wavy line indicates the connection to Z;

$L^2$, o and D are as defined above.

$L^2$ may be present of absent, preferably $L^2$ is present and o=1. For preferred antibody-conjugate (XIa), $L^2$ is according to structure (L3) and $R^{17}$ is $CH_3$. For preferred antibody-conjugate (XIb), $L^2$ is according to structure (L3) and $R^{17}$ is $CH_2CH_2CH_2NHC(O)NH_2$. The antibody-conjugate (XI) preferably has structure (XIb).

In a particularly preferred embodiment, the antibody-conjugate according to structure (XI) contains a payload D selected from the group consisting of calicheamicin, MMAE, PF-06380101, exatecan and DXd, more preferably a payload D selected from the group consisting of calicheamicin, MMAE, and exatecan, most preferably with calicheamicin as payload D.

Antibody-conjugate (XII) has a linker-payload moiety according to the following structure:

(XII)

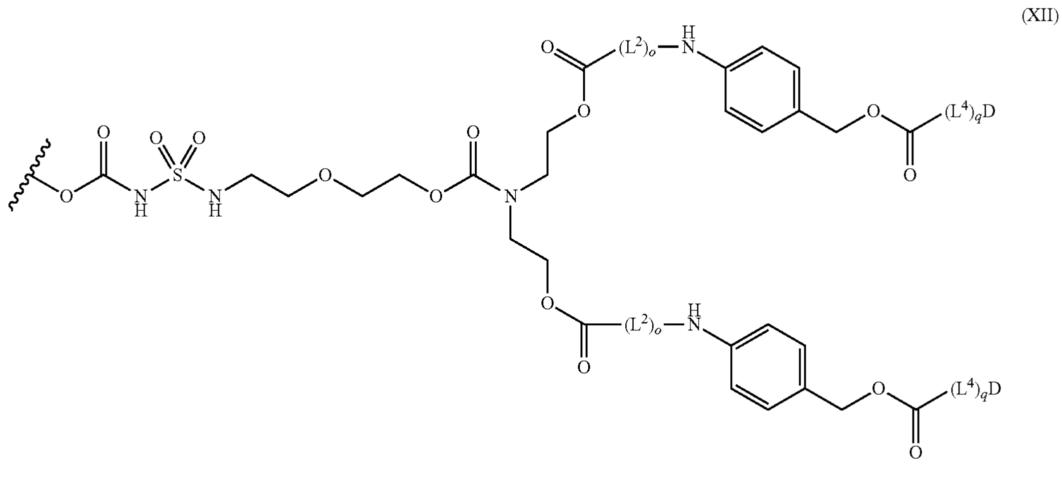

wherein:

the wavy line indicates the connection to Z;

$L^2$, $L^4$, o, q and D are as defined above.

$L^2$ may be present of absent, preferably $L^2$ is present and o=1. For preferred antibody-conjugate (XIIa), $L^2$ is according to structure (L3) and $R^{17}$ is $CH_3$. For preferred antibody-conjugate (XIIb), $L^2$ is according to structure (L3) and $R^{17}$ is $CH_2CH_2CH_2NHC(O)NH_2$. Preferably, $R^{17}$=$CH_2CH_2CH_2NHC(O)NH_2$.

$L^4$ may be present of absent. For preferred antibody-conjugate (XIIc), q=0 and $L^4$ is absent. For preferred antibody-conjugate (XIId), q=1 and $L^4$ is a diamine spacer according to the structure —$NR^{22}$—($C_z$-alkylene)-$NR^{22}$—, wherein z is an integer in the range 1-20, and $R^{22}$ is H or $C_1$-$C_4$ alkyl.

For preferred antibody-conjugate (XIIe), $L^2$ is according to structure (L3), $R^{17}$ is $CH_3$, q=0 and $L^4$ is absent. For preferred antibody-conjugate (XIIf), $L^2$ is according to structure (L3), $R^{17}$ is $CH_3$, q=1 and $L^4$ is a diamine spacer according to the structure —$NR^{22}$—($C_z$-alkylene)-$NR^{22}$—, wherein z is an integer in the range 1-10, preferably wherein z=2, and $R^{22}$ is H or $C_1$-$C_4$ alkyl.

For preferred antibody-conjugate (XIIg), $L^2$ is according to structure (L3), $R^{17}$ is $CH_2CH_2CH_2NHC(O)NH_2$, q=0 and $L^4$ is absent. For preferred antibody-conjugate (XIIh), $L^2$ is according to structure (L3), $R^{17}$ is $CH_2CH_2CH_2NHC(O)NH_2$, q=1 and $L^4$ is a diamine spacer according to the structure —$NR^{22}$—($C_z$-alkylene)-$NR^{22}$—, wherein z is an integer in the range 1-20, and $R^{22}$ is H or $C_1$-$C_4$ alkyl.

In the context of antibody-conjugate (XII), it is preferred that z is an integer in the range of 1-10, more preferably z=2-6, most preferably z=2. In the context of antibody-conjugate (XII), it is further preferred that $R^{22}$ is H or $CH_3$.

In the context of antibody-conjugate (XII), structures (XIIg) and (XIIh) are most preferred.

In a particularly preferred embodiment, the antibody-conjugate according to structure (XII) contains a payload D selected from the group consisting of calicheamicin, MMAE, PF-06380101, exatecan and DXd, more preferably a payload D selected from the group consisting of calicheamicin, MMAE, and exatecan, most preferably with exatecan as payload D.

Antibody-conjugate (XIII) has a linker-payload moiety according to the following structure:

(XIII)

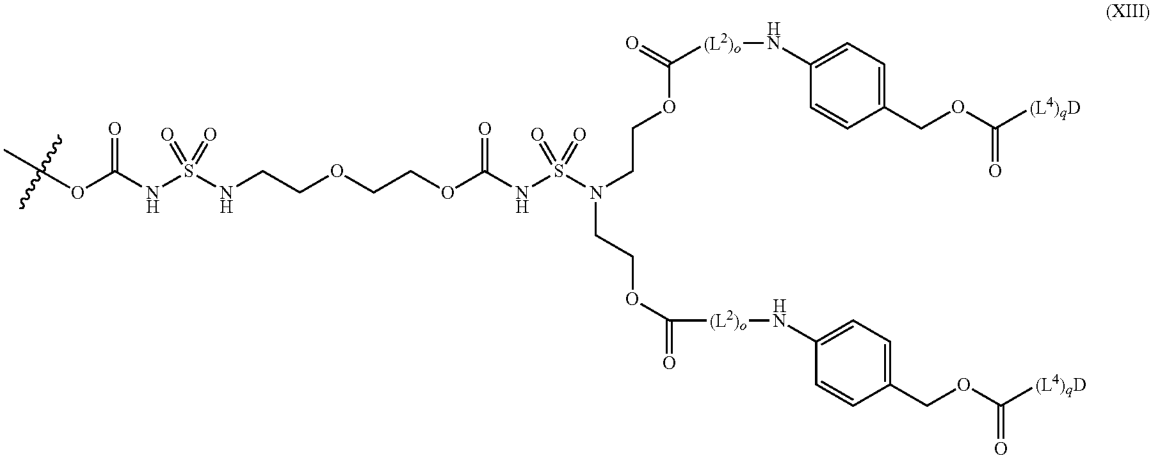

wherein:

the wavy line indicates the connection to Z;

$L^2$, $L^4$, o, q and D are as defined above.

$L^2$ may be present of absent, preferably $L^2$ is present and o=1. For preferred antibody-conjugate (XIIIa), $L^2$ is according to structure (L3) and $R^{17}$ is $CH_3$. For preferred antibody-conjugate (XIIIb), $L^2$ is according to structure (L3) and $R^{17}$ is $CH_2CH_2CH_2NHC(O)NH_2$. Preferably, $R^{17}$=$CH_3$.

$L^4$ may be present of absent. For preferred antibody-conjugate (XIIIc), q=0 and $L^4$ is absent. For preferred antibody-conjugate (XIIId), q=1 and $L^4$ is a diamine spacer according to the structure —$NR^{22}$—($C_z$-alkylene)-$NR^{22}$—, wherein z is an integer in the range 1-20, and $R^{22}$ is H or $C_1$-$C_4$ alkyl.

For preferred antibody-conjugate (XIIIe), $L^2$ is according to structure (L3), $R^{17}$ is $CH_3$, q=0 and $L^4$ is absent. For preferred antibody-conjugate (XIIIf), $L^2$ is according to structure (L3), $R^{17}$ is $CH_3$, q=1 and $L^4$ is a diamine spacer according to the structure —$NR^{22}$—($C_z$-alkylene)-$NR^{22}$—, wherein z is an integer in the range 1-10, preferably wherein z=2, and $R^{22}$ is H or $C_1$-$C_4$ alkyl.

For preferred antibody-conjugate (XIIIg), $L^2$ is according to structure (L3), $R^{17}$ is $CH_2CH_2CH_2NHC(O)NH_2$, q=0 and $L^4$ is absent. For preferred antibody-conjugate (XIIIh), $L^2$ is according to structure (L3), $R^{17}$ is $CH_2CH_2CH_2NHC(O)NH_2$, q=1 and $L^4$ is a diamine spacer according to the structure —$NR^{22}$—($C_z$-alkylene)-$NR^{22}$—, wherein z is an integer in the range 1-20, and $R^{22}$ is H or $C_1$-$C_4$ alkyl.

In the context of antibody-conjugate (XIII), it is preferred that z is an integer in the range of 1-10, more preferably z=2-6, most preferably z=2. In the context of antibody-conjugate (XIII), it is further preferred that $R^{22}$ is H or $CH_3$.

In the context of antibody-conjugate (XIII), structure (XIIIe) is most preferred.

In a particularly preferred embodiment, the antibody-conjugate according to structure (XIII) contains a payload D selected from the group consisting of calicheamicin, MMAE, PF-06380101, exatecan and DXd, more preferably a payload D selected from the group consisting of calicheamicin, MMAE, and exatecan, most preferably with exatecan as payload D.

In one particularly preferred embodiment, the antibody-conjugate according to the invention is according to structure (XIb) as defined above, and the antibody is labetuzumab as defined above or tusamitamab as defined above and the payload is calicheamicin.

In one particularly preferred embodiment, the antibody-conjugate according to the invention is according to structure (XIIIe) as defined above, and the antibody is labetuzumab as defined above or tusamitamab as defined above and the payload is exatecan.

In one particularly preferred embodiment, the antibody-conjugate according to the invention is according to structure (XIIIe) as defined above, and the antibody is labetuzumab as defined above and the payload is exatecan.

It is further preferred that these preferred antibody-conjugates are conjugated through the glycan, i.e. b=1, more preferably a trimmed glycan, i.e. j=0. Herein, it is further preferred that S=GalNAc and w'=0. Herein, it is further preferred that connecting group Z is formed by an azide-alkyne cycloaddition, preferably connecting group Z=(Z39), wherein ring Z=(Za) and V=$CH_2$. Herein, it is further preferred that x=1. Herein, it is further preferred that y=2, more preferably that x=1 and y=2.

In a most preferred embodiment, the antibody-conjugate according to the invention is according to structure (XIIIe) as defined above, and the antibody is labetuzumab as defined above and the payload is exatecan, wherein b=1, e=0, S=GalNAc, w'=0, connecting group Z=(Z39), wherein ring Z=(Za) and V=$CH_2$, x=1 and y=2.

Compound According to General Structure (2)

The compound has general structure (2):

Q-L-D (2)

wherein:

- Q is a reactive moiety;
- L is a linker that links Z to D;
- D is selected from the group consisting of anthracyclines, camptothecins, tubulysins, enediynes, amanitins, duocarmycins, maytansinoids, auristatins, eribulins, BCL-XL inhibitors, hemiasterlins, KSP inhibitors, TLR agonists, indolinobenzodiazepine dimers or pyrrolobenzodiazepine dimers (PBDs), and analogues or prodrugs thereof;

The compound of general structure (2) may also be referred to as a “linker-drug construct”, for containing linker L and payload D of the final conjugate. Compounds according to general formula (2) can be prepared by the skilled person using standard organic synthesis techniques, and as exemplified in the examples. Linker L and payload D are defined above in the context of the conjugate according to structure (1).

Reactive Moiety Q

The compound according to general structure (2) comprises a reactive moiety Q. In the context of the present invention, the term “reactive moiety” may refer to a chemical moiety that comprises a reactive group, but also to a reactive group itself. For example, a cyclooctynyl group is a reactive group comprising a reactive group, namely a C—C triple bond. Similarly, an N-maleimidyl group is a reactive group, comprising a C—C double bond as a reactive group. However, a reactive group, for example an azido reactive group, a thiol reactive group or an alkynyl reactive group, may herein also be referred to as a reactive moiety.

Q serves as chemical handle for the connection to $S(F)_x$. In other words, Q is reactive towards and complementary to F. Herein, a reactive group is denoted as “complementary” to a reactive group when said reactive group reacts with said reactive group selectively, optionally in the presence of other functional groups. Complementary reactive and functional groups are known to a person skilled in the art, and are described in more detail below. As such, the compound according to general structure (2) is conveniently used in a conjugation reaction, wherein a chemical reaction between Q and F takes place, thereby forming an antibody-conjugate comprising a covalent connection between payload D and the antibody.

The exact nature of Q, and F, depends on the type of conjugation reaction that is employed. The skilled person will be able to select the appropriate combination of Q and F. Preferably, Q, and thus also F, is reactive in a cycloaddition or a nucleophilic reaction. Thus, Q preferably comprises a click probe, a thiol, a thiol-reactive moiety, an amine or an amine-reactive moiety, more preferably Q is a click probe, a thiol-reactive moiety or an amine-reactive moiety, most preferably Q is a click probe. The click probe is reactive in a cycloaddition (click reaction) and is preferably selected from an azide, a tetrazine, a triazine, a nitrone, a nitrile oxide, a nitrile imine, a diazo compound, an ortho-quinone, a dioxothiophene, a sydnone, an alkene moiety and an alkyne moiety. Preferably, the click probe comprises or is an alkene moiety or an alkyne moiety, more preferably wherein the alkene is a (hetero)cycloalkene and/or the alkyne is a terminal alkyne or a (hetero)cycloalkyne. Typical thiol-reactive moieties are selected from maleimide moiety, a haloacetamide moiety, an allenamide moiety, a phosphonamidite moiety, a cyanoethynyl moiety, a vinylsulfone, a vinylpyridine moiety or a methylsulfonylphenyloxadiazole moiety. Most preferably, the thiol-reactive moiety comprises or is a maleimide moiety. Typical amine-reactive moieties are selected from N-hydroxysuccinimidyl esters and other activated esters, p-nitrophenyl carbonates and other activated carbonates, isocyanates, isothiocyanates, haloacetamides and benzyl halides. In a preferred embodiment, Q is selected from an alkene moiety, an alkyne moiety, a thiol-reactive moiety or an amine-reactive moiety, more preferably an alkene moiety or an alkyne moiety, even more preferably an alkyne moiety. Herein, the alkene is preferably a (hetero)cycloalkene and the alkyne is preferably a terminal alkyne or a (hetero)cycloalkyne. Most preferably, Q is a cyclic (hetero)alkyne moiety. Each of these moieties are further defined here below.

Thus, in an especially preferred embodiment, Q comprises a cyclic (hetero)alkyne moiety. The alkynyl group may also be referred to as a (hetero)cycloalkynyl group, i.e. a heterocycloalkynyl group or a cycloalkynyl group, wherein the (hetero)cycloalkynyl group is optionally substituted. Preferably, the (hetero)cycloalkynyl group is a (hetero)cycloheptynyl group, a (hetero)cyclooctynyl group, a (hetero)cyclononynyl group or a (hetero)cyclodecynyl group. Herein, the (hetero)cycloalkynes may optionally be substituted. Preferably, the (hetero)cycloalkynyl group is an optionally substituted (hetero)cycloheptynyl group or an optionally substituted (hetero)cyclooctynyl group. Most preferably, the (hetero)cycloalkynyl group is a (hetero)cyclooctynyl group, wherein the (hetero)cyclooctynyl group is optionally substituted.

In an especially preferred embodiment, Q comprises a (hetero)cycloalkynyl or (hetero)cycloalkenyl group and is according to structure (Q1):

(Q1)

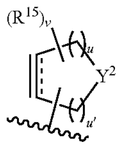

Herein:

- the bond depicted as ═══ is a double bond or a triple bond;
- $R^{15}$ is independently selected from the group consisting of hydrogen, halogen, $-OR^{16}$, $-NO_2$, $-CN$, $-S(O)_2R^{16}$, $-S(O)_3^{(-)}$, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups and wherein the alkyl groups, (hetero)aryl groups, alkyl(hetero)aryl groups and (hetero)arylalkyl groups are optionally substituted, wherein two substituents $R^{15}$ may be linked together to form an optionally substituted annulated cycloalkyl or an optionally substituted annulated (hetero)arene substituent, and wherein $R^{16}$ is independently selected from the group consisting of hydrogen, halogen, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero) arylalkyl groups;
- $Y^2$ is $C(R^{31})_2$, O, S, $S^{(+)}R^{31}$, $S(O)R^{31}$, $S(O){=}NR^{31}$ or $NR^{31}$, wherein $S^{(+)}$ is a cationic sulphur atom counterbalanced by $B^{(-)}$, wherein $B^{(-)}$ is an anion, and wherein each $R^{31}$ individually is $R^{15}$ or a connection with D, connected via L;
- u is 0, 1, 2, 3, 4 or 5;
- u' is 0, 1, 2, 3, 4 or 5, wherein u+u'=0, 1, 2, 3, 4, 5, 6, 7 or 8;
- v=an integer in the range 0-16;

Typically, v=(u+u')×2 (when the connection to L, depicted by the wavy bond, is via $Y^2$) or [(u+u')×2]−1 (when the connection to L, depicted by the wavy bond, is via one of the carbon atoms).

In a preferred embodiment of structure (Q1), reactive group Q comprises a (hetero)cycloalkynyl group and is according to structure (Q1a):

(Q1a)

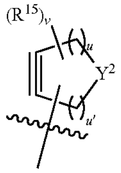

Herein,

- $R^{15}$ and $Y^2$ are as defined above
- u is 0, 1, 2, 3, 4 or 5;
- u' is 0, 1, 2, 3, 4 or 5, wherein u+u'=4, 5, 6, 7 or 8;
- v=an integer in the range 8-16.

In a preferred embodiment, u+u'=4, 5 or 6, more preferably u+u'=5. In a preferred embodiment, v=8, 9 or 10, more preferably v=9 or 10, most preferably v=10.

In a preferred embodiment, Q is a (hetero)cycloalkynyl group selected from the group consisting of (Q2)-(Q20) and (Q20a) depicted here below.

(Q2)

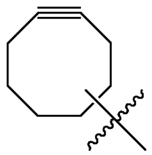

(Q3)

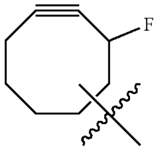

(Q4)

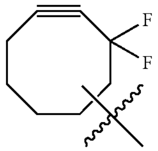

(Q5)

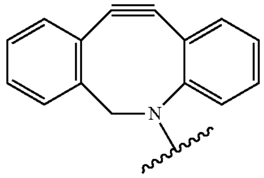

(Q6)

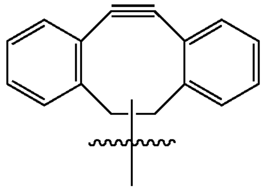

-continued (Q7)

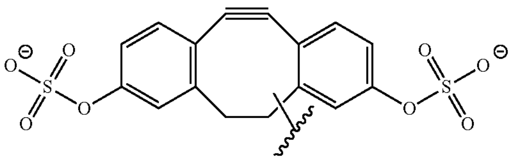

(Q8)

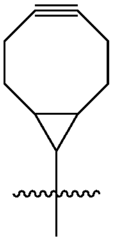

(Q9)

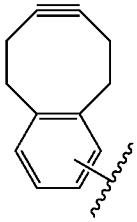

(Q10)

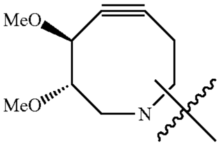

(Q11)

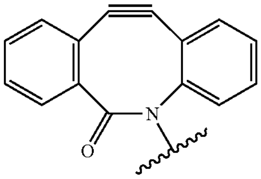

(Q12)

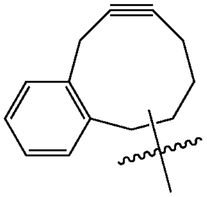

(Q13)

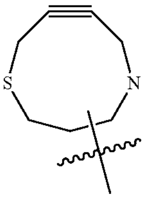

(Q14)

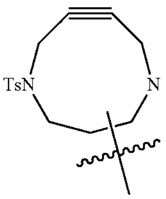

-continued (Q15)

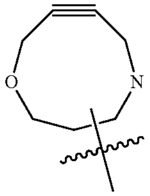

(Q16)

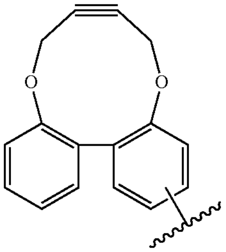

(Q17)

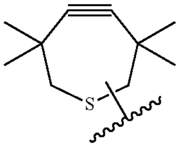

(Q18)

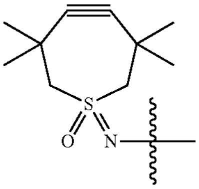

(Q19)

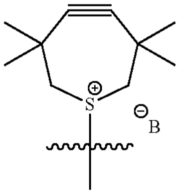

(Q20)

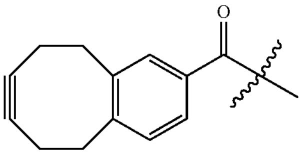

(Q20a)

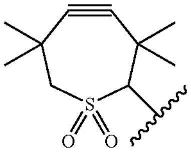

Herein, the connection to L, depicted with the wavy bond, may be to any available carbon or nitrogen atom of Q. The nitrogen atom of (Q10), (Q13), (Q14) and (Q15) may bear the connection to L, or may contain a hydrogen atom or be optionally functionalized. $B^{(-)}$ is an anion, which is preferably selected from $^{(-)}$OTf, $Cl^{(-)}$, $Br^{(-)}$ or $I^{(-)}$, most preferably $B^{(-)}$ is $^{(-)}$OTf. In the conjugation reaction, $B^{(-)}$ does not need to be a pharmaceutically acceptable anion, since $B^{(-)}$ will exchange with the anions present in the reaction mixture anyway. In case (Q19) is used for Q, the negatively charged counter-ion is preferably pharmaceutically acceptable upon isolation of the conjugate according to the invention, such that the conjugate is readily useable as medicament.
In a further preferred embodiment, Q is a (hetero)cycloalkynyl group selected from the group consisting of (Q21)-(Q38) and (Q38a) depicted here below.
(Q21)
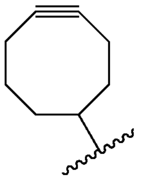
(Q22)
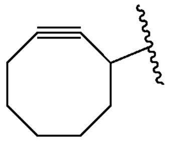
(Q23)
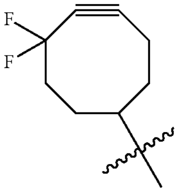
(Q24)
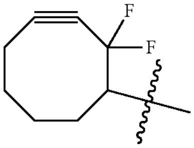
(Q25)
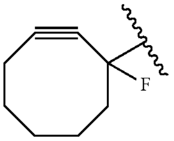
(Q26)
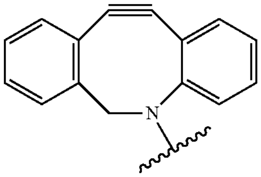
(Q27)
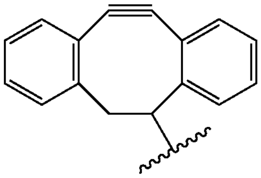
(Q28)
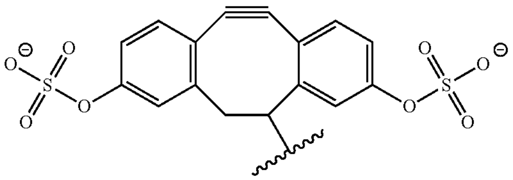
-continued
(Q29)
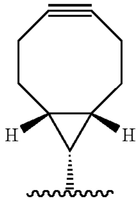
(Q30)
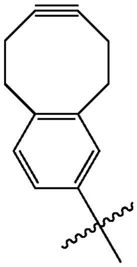
(Q31)
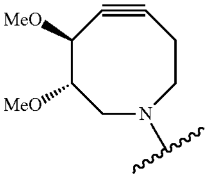
(Q32)
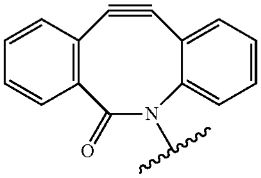
(Q33)
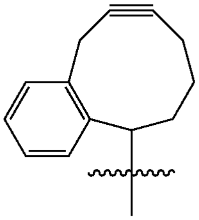
(Q34)
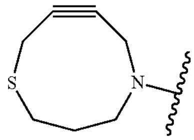
(Q35)
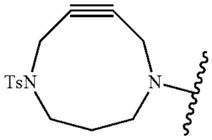
(Q36)
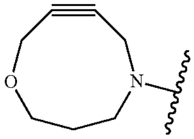

-continued (Q37)

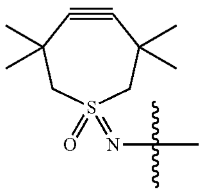

(Q38)

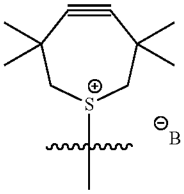

(Q38a)

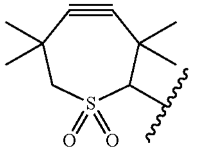

In structure (Q38), $B^{(-)}$ is an anion, which is preferably selected from $^{(-)}OTf$, $Cl^{(-)}$, $Br^{(-)}$ or $I^{(-)}$, most preferably $B^{(-)}$ is $^{(-)}OTf$.

In a preferred embodiment, Q comprises a (hetero)cyclooctyne moiety or a (hetero)cycloheptyne moiety, preferably according to structure (Q8), (Q26), (Q27), (Q28), (Q37) or (Q38a), more preferably according to structure (Q8), (Q26), (Q27), (Q28) or (Q37), which are optionally substituted. Each of these preferred options for Q are further defined here below.

Thus, in a preferred embodiment, Q comprises a heterocycloheptyne moiety according to structure (Q37), also referred to as a TMTHSI, which is optionally substituted. Preferably, the heterocycloheptyne moiety according to structure (Q37) is not substituted.

In an alternative preferred embodiment, Q comprises a cyclooctyne moiety according to structure (Q8), more preferably according to (Q29), also referred to as a bicyclo[6.1.0]non-4-yn-9-yl]group (BCN group), which is optionally substituted. Preferably, the cyclooctyne moiety according to structure (Q8) or (Q29) is not substituted. In the context of the present embodiment, Q preferably is a (hetero)cyclooctyne moiety according to structure (Q39) as shown below, wherein V is $(CH_2)_l$ and l is an integer in the range of 0 to 10, preferably in the range of 0 to 6. More preferably, l is 0, 1, 2, 3 or 4, more preferably l is 0, 1 or 2 and most preferably l is 0 or 1. In the context of group (Q39), l is most preferably 1. Most preferably, Q is according to structure (Q42), defined further below.

In an alternative preferred embodiment, Q comprises a (hetero)cyclooctyne moiety according to structure (Q26), (Q27) or (Q28), also referred to as a DIBO, DIBAC, DBCO or ADIBO group, which are optionally substituted. In the context of the present embodiment, Q preferably is a (hetero)cyclooctyne moiety according to structure (Q40) or (Q41) as shown below, wherein $Y^1$ is O or $NR^{11}$, wherein $R^{11}$ is independently selected from the group consisting of hydrogen, a linear or branched $C_1$-$C_{12}$ alkyl group or a $C_4$-$C_{12}$ (hetero)aryl group. The aromatic rings in (Q40) are optionally O-sulfonylated at one or more positions, whereas the rings of (Q41) may be halogenated at one or more positions. Preferably, the (hetero)cyclooctyne moiety according to structure (Q40) or (Q41) is not further substituted. Most preferably, Q is according to structure (Q43), defined further below.

In an alternative preferred embodiment, Q comprises a heterocycloheptynyl group and is according to structure (Q37).

(Q37)

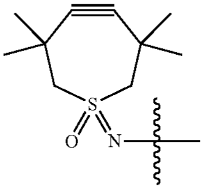

(Q39)

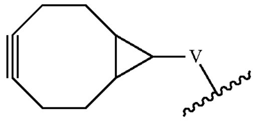

(Q40)

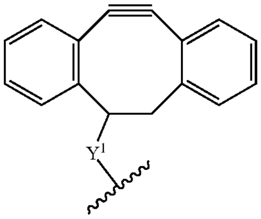

(Q41)

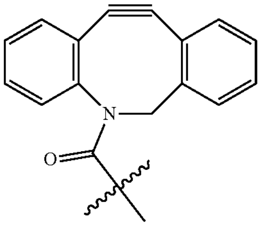

In an especially preferred embodiment, Q comprises a cyclooctynyl group and is according to structure (Q42):

(Q42)

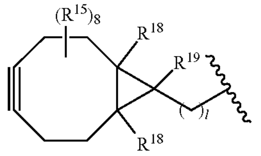

Herein:

$R^{15}$ is independently selected from the group consisting of hydrogen, halogen, —$OR^{16}$, —$NO_2$, —CN, —$S(O)_2R^{16}$, —$S(O)_3^{(-)}$, $C_1$-$C_{24}$ alkyl groups, $C_5$-$C_{24}$ (hetero)aryl groups, $C_7$-$C_{24}$ alkyl(hetero)aryl groups and $C_7$-$C_{24}$ (hetero)arylalkyl groups and wherein the alkyl groups, (hetero)aryl groups, alkyl(hetero)aryl groups and (hetero)arylalkyl groups are optionally substituted, wherein two substituents $R^{15}$ may be linked together to form an optionally substituted annulated cycloalkyl or an optionally substituted annulated (hetero)arene substituent, and wherein $R^{16}$ is independently selected from the group consisting of hydrogen, halogen, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups;

$R^{18}$ is independently selected from the group consisting of hydrogen, halogen, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups;

$R^{19}$ is selected from the group consisting of hydrogen, halogen, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups, the alkyl groups optionally being interrupted by one of more hetero-atoms selected from the group consisting of O, N and S, wherein the alkyl groups, (hetero)aryl groups, alkyl(hetero)aryl groups and (hetero)arylalkyl groups are independently optionally substituted, or $R^{19}$ is a second occurrence of Q or D connected via a spacer moiety; and l is an integer in the range 0 to 10.

In a preferred embodiment of the reactive group according to structure (Q42), $R^{15}$ is independently selected from the group consisting of hydrogen, halogen, —$OR^{16}$, $C_1$-$C_6$ alkyl groups, $C_5$-$C_6$ (hetero)aryl groups, wherein $R^{16}$ is hydrogen or $C_1$-$C_6$ alkyl, more preferably $R^{15}$ is independently selected from the group consisting of hydrogen and $C_1$-$C_6$ alkyl, most preferably all $R^{15}$ are H. In a preferred embodiment of the reactive group according to structure (Q42), $R^{18}$ is independently selected from the group consisting of hydrogen, $C_1$-$C_6$ alkyl groups, most preferably both $R^{18}$ are H. In a preferred embodiment of the reactive group according to structure (Q42), $R^{19}$ is H. In a preferred embodiment of the reactive group according to structure (Q42), l is 0 or 1, more preferably l is 1.

In an especially preferred embodiment, Q comprises a (hetero)cyclooctynyl group and is according to structure (Q43):

(Q43)

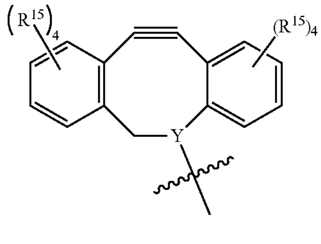

Herein:

$R^{15}$ is independently selected from the group consisting of hydrogen, halogen, —$OR^{16}$, —$NO_2$, —CN, —$S(O)_2R^{16}$, —$S(O)_3^{(-)}$, $C_1$-$C_{24}$ alkyl groups, $C_5$-$C_{24}$ (hetero)aryl groups, $C_7$-$C_{24}$ alkyl(hetero)aryl groups and $C_7$-$C_{24}$ (hetero)arylalkyl groups and wherein the alkyl groups, (hetero)aryl groups, alkyl(hetero)aryl groups and (hetero)arylalkyl groups are optionally substituted, wherein two substituents $R^{15}$ may be linked together to form an optionally substituted annulated cycloalkyl or an optionally substituted annulated (hetero)arene substituent, and wherein $R^{16}$ is independently selected from the group consisting of hydrogen, halogen, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups;

Y is N or $CR^{15}$.

In a preferred embodiment of the reactive group according to structure (Q43), $R^{15}$ is independently selected from the group consisting of hydrogen, halogen, —$OR^{16}$, —$S(O)_3^{(-)}$, $C_1$-$C_6$ alkyl groups, $C_5$-$C_6$ (hetero)aryl groups, wherein $R^{16}$ is hydrogen or $C_1$-$C_6$ alkyl, more preferably $R^{15}$ is independently selected from the group consisting of hydrogen and —$S(O)_3^{(-)}$. In a preferred embodiment of the reactive group according to structure (Q43), Y is N or CH, more preferably Y═N.

In an especially preferred embodiment, Q comprises a heterocycloheptynyl group and is according to structure (Q37) or (Q38a), preferably according to structure (Q37)

(Q37)

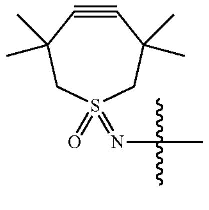

(Q38a)

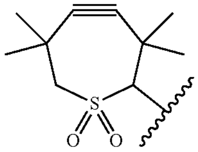

In an alternative preferred embodiment, Q comprises a cyclic alkene moiety. The alkenyl group Q may also be referred to as a (hetero)cycloalkenyl group, i.e. a heterocycloalkenyl group or a cycloalkenyl group, preferably a cycloalkenyl group, wherein the (hetero)cycloalkenyl group is optionally substituted. Preferably, the (hetero)cycloalkenyl group is a (hetero)cyclopropenyl group, a (hetero)cyclobutenyl group, a norbornene group, a norbornadiene group, a trans-(hetero)cycloheptenyl group, a trans-(hetero)cyclooctenyl group, a trans-(hetero)cyclononenyl group or a trans-(hetero)cyclodecenyl group, which may all optionally be substituted. Especially preferred are (hetero)cyclopropenyl groups, trans-(hetero)cycloheptenyl group or trans-(hetero)cyclooctenyl groups, wherein the (hetero)cyclopropenyl group, the trans-(hetero)cycloheptenyl group or the trans-(hetero)cyclooctenyl group is optionally substituted. Preferably, Q comprises a cyclopropenyl moiety according to structure (Q44), a hetereocyclobutene moiety according to structure (Q45), a norbornene or norbornadiene group according to structure (Q46), a trans-(hetero)cycloheptenyl moiety according to structure (Q47) or a trans-(hetero)cyclooctenyl moiety according to structure (Q48). Herein, $Y^3$ is selected from $C(R^{23})_2$, $NR^{23}$ or O, wherein each $R^{23}$ is individually hydrogen, $C_1$-$C_6$ alkyl or is connected to L, optionally via a spacer, and the bond labelled - - - is a single or double bond. In a further preferred embodiment, the cyclopropenyl group is according to structure (Q49). In another preferred embodiment, the trans-(hetero)cycloheptene group is according to structure (Q50) or (Q51). In another preferred embodiment, the trans-(hetero)cyclooctene group is according to structure (Q52), (Q53), (Q54), (Q55) or (Q56).

(Q44)

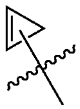

-continued (Q45)

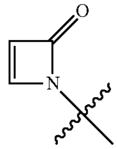

(Q46)

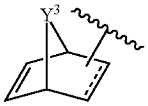

(Q47)

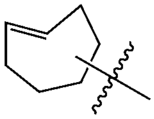

(Q48)

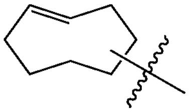

(Q49)

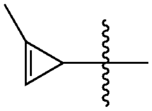

(Q50)

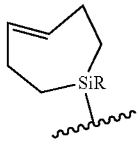

(Q51)

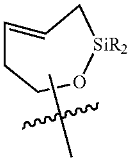

(Q52)

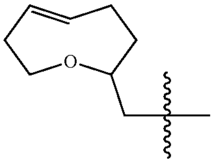

(Q53)

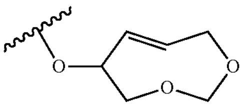

(Q54)

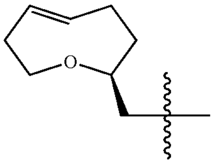

-continued (Q55)

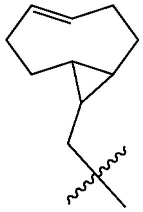

(Q56)

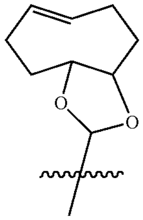

Herein, the R group(s) on Si in (Q50) and (Q51) are typically alkyl or aryl, preferably $C_1$-$C_6$ alkyl.

In an alternative preferred embodiment, Q is a thiol-reactive probe. In this embodiment, Q is a reactive group compatible with cysteine conjugation. Such probes are known in the art and may be selected from the group consisting of a maleimide moiety, a haloacetamide moiety, an allenamide moiety, a phosphonamidite moiety, a cyano-ethynyl moiety, a vinylsulfone, a vinylpyridine moiety or a methylsulfonylphenyloxadiazole moiety. Most preferably, Q comprises or is a maleimide moiety. Reagents may be monoalkylation type or may be a cross-linker for reaction with two cysteine side-chains.

In a further preferred embodiment, probe Q is selected from the group consisting of (Q57)-(Q71) depicted here below.

(Q57)

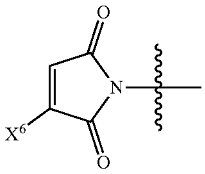

(Q58)

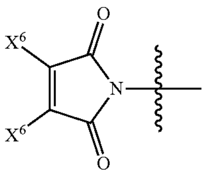

(Q59)

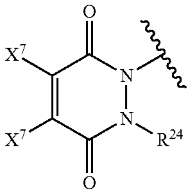

-continued (Q60)

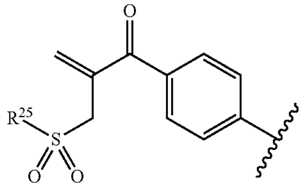

(Q61)

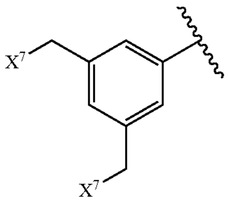

(Q62)

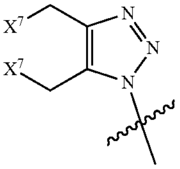

(Q63)

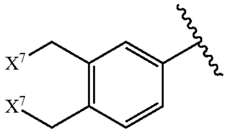

(Q64)

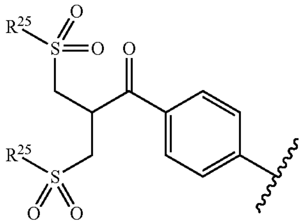

(Q65)

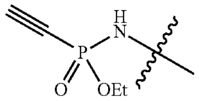

(Q66)

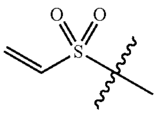

(Q67)

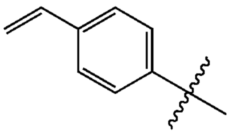

(Q68)

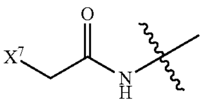

(Q69)

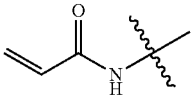

-continued (Q70)

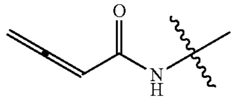

(Q71)

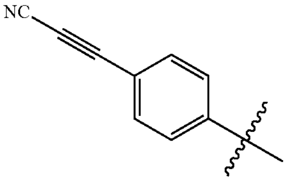

wherein:

$X^6$ is H, halogen, PhS, MeS, preferably a halogen, such as Cl, Br, I;

$X^7$ is halogen, PhS, MeS, preferably a halogen, such as Cl, Br, I;

$R^{24}$ is H or $C_{1-12}$ alkyl, preferably H or $C_{1-6}$ alkyl;

$R^{25}$ is H, $C_{1-12}$ alkyl, $C_{1-12}$ aryl, $C_{1-12}$ alkaryl or $C_{1-12}$ aralkyl, preferably H or para-methylphenyl;

wherein the aromatic ring of (Q61) and (Q63) may optionally be a heteroaromatic ring, such as a phenyl or pyridine ring.

In a preferred embodiment of thiol-reactive probe (Q57), the probe Q is selected from the group consisting of (Q72)-(Q74) depicted here below.

(Q72)

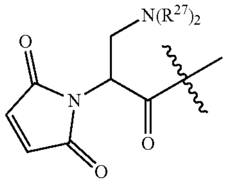

(Q73)

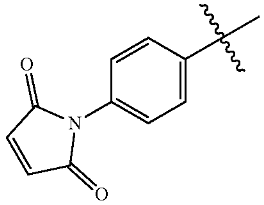

(Q74)

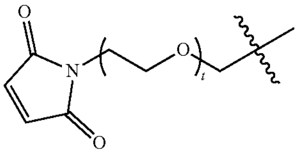

wherein:

$R^{27}$ is $C_{1-12}$ alkyl, $C_{1-12}$ aryl, $C_{1-12}$ alkaryl or $C_{1-12}$ aralkyl;

t is an integer in the range of 0-15, preferably 1-10.

In an alternative preferred embodiment, Q is an amine-reactive probe. In this embodiment, Q is a reactive group compatible with lysine conjugation. Such probes are known in the art and may be selected from the group consisting of N-hydroxysuccinimidyl groups, isocyanate groups, isothiocyanate groups and benzoyl halide groups. Most preferably, Q comprises or is an N-hydroxysuccinimidyl esters or a p-nitrophenyl carbonate moiety.

In a further preferred embodiment, probe Q is selected from the group consisting of (Q75)-(Q79) depicted here below.

(Q75)

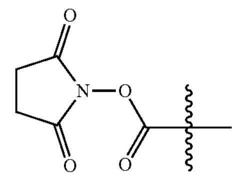

(Q76)

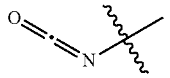

(Q77)

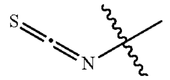

(Q78)

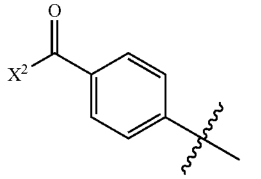

(Q79)

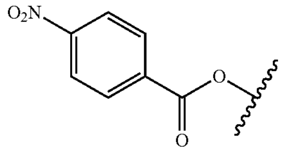

Herein, $X^2$ is halogen, preferably F.

In a preferred embodiment, Q is selected from the group consisting of (Q1)-(Q79).

Antibody According to General Structure (3)

The antibody has general structure (3):

$$AB\text{-}[(L^6)_b\text{-}\{F\}_x]_y \quad (3)$$

wherein:

AB is an antibody capable of targeting CEA-expressing tumours;

b is 0 or 1;

$L^6$ is $\text{-GlcNAc(Fuc)}_w\text{-(G)}_j\text{-S-(}L^7)_{w'}\text{-}$, wherein G is a monosaccharide, j is an integer in the range of 0-10, S is a sugar or a sugar derivative, GlcNAc is N-acetylglucosamine and Fuc is fucose, w is 0 or 1, w' is 0, 1 or 2 and $L^7$ is —N(H)C(O)$CH_2$—, —N(H)C(O)$CF_2$— or —$CH_2$—;

F is a reactive moiety;

x is 1 or 2; and y is 1, 2, 3 or 4.

The antibody of general structure (3) may also be referred to as a "(modified) antibody", for being an antibody containing reactive groups F, wherein the reactive groups F are naturally present or the antibody is modified to incorporate the reactive groups F. The (modified) antibody according to general formula (2) can be prepared by the skilled person using standard organic and/or enzymatic synthesis techniques, and as exemplified in the examples. Antibody AB, linker $L^6$, b, x and y are defined above in the context of the conjugate according to structure (1).

Reactive Moiety F

F is reactive towards Q in the conjugation reaction defined below, preferably wherein the conjugation reaction is a cycloaddition or a nucleophilic reaction. As the skilled person will understand, the options for F are the same as those for Q, provided that F and Q are reactive towards each other. Thus, F preferably comprises a click probe, a thiol, a thiol-reactive moiety, an amine or an amine-reactive moiety, more preferably F is a click probe, a thiol or an amine, most preferably F is a click probe. The click probe is reactive in a cycloaddition (click reaction) and is preferably selected from an azide, a tetrazine, a triazine, a nitrone, a nitrile oxide, a nitrile imine, a diazo compound, an ortho-quinone, a dioxothiophene, a sydnone, an alkene moiety and an alkyne moiety. Preferably, the click probe comprises or is an azide, a tetrazine, a triazine, a nitrone, a nitrile oxide, a nitrile imine, a diazo compound, an ortho-quinone, a dioxothiophene or a sydnone, most preferably an azide. Typical thiol-reactive moieties are selected from maleimide moiety, a haloacetamide moiety, an allenamide moiety, a phosphonamidite moiety, a cyanoethynyl moiety, an ortho-quinone moiety, a vinylsulfone, a vinylpyridine moiety or a methylsulfonylphenyloxadiazole moiety. Most preferably, the thiol-reactive moiety comprises or is a maleimide moiety. Typical amine-reactive moieties are selected from N-hydroxysuccinimidyl esters, isocyanates, isothiocyanates and benzyl halides. In a preferred embodiment, F is a click probe or a thiol, more preferably F is an azide or a thiol, most preferably F is an azide.

More than one reactive group F may be present in the antibody. The reactive group F in the antibody may be naturally present or may be placed in the antibody by a specific technique, for example a (bio)chemical or a genetic technique. The reactive group that is placed in the antibody is prepared by chemical synthesis, for example an azide or a terminal alkyne. Methods of preparing modified antibodies are known in the art, e.g. from WO 2014/065661, WO 2016/170186 and WO 2016/053107, which are incorporated herein by reference. From the same documents, the conjugation reaction between the modified antibody and a linker-drug construct is known to the skilled person.

Preferably, F is a click probe reactive towards a (hetero) cycloalkene and/or a (hetero)cycloalkyne, and is typically selected from the group consisting of azide, tetrazine, triazine, nitrone, nitrile oxide, nitrile imine, diazo compound, ortho-quinone, dioxothiophene and sydnone. Preferred structures for the reactive group are structures (F1)-(F10) depicted here below.

(F1)

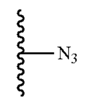

(F2)

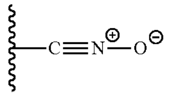

(F3)

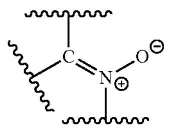

(F4)

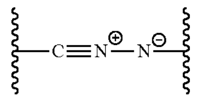

-continued (F5)

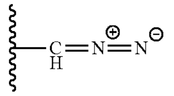

(P6)

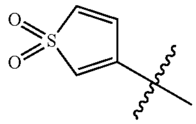

(F7)

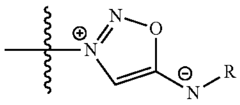

(F8)

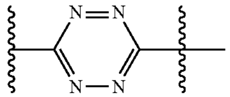

(F9)

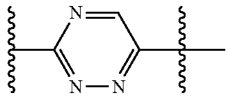

(F10)

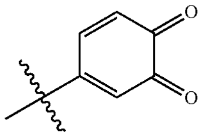

Herein, the wavy bond represents the connection to the payload. For (F3), (F4), (F8) and (F9), the payload can be connected to any one of the wavy bonds. The other wavy bond may then be connected to an R group selected from hydrogen, $C_1$-$C_{24}$ alkyl groups, $C_2$-$C_{24}$ acyl groups, $C_3$-$C_{24}$ cycloalkyl groups, $C_2$-$C_{24}$ (hetero)aryl groups, $C_3$-$C_{24}$ alkyl (hetero)aryl groups, $C_3$-$C_{24}$ (hetero)arylalkyl groups and $C_1$-$C_{24}$ sulfonyl groups, each of which (except hydrogen) may optionally be substituted and optionally interrupted by one or more heteroatoms selected from O, S and $NR^{32}$ wherein $R^{32}$ is independently selected from the group consisting of hydrogen and $C_1$-$C_4$ alkyl groups. The skilled person understands which R groups may be applied for each of the groups F. For example, the R group connected to the nitrogen atom of (F3) may be selected from alkyl and aryl, and the R group connected to the carbon atom of (F3) may be selected from hydrogen, alkyl, aryl, acyl and sulfonyl. Preferably, the reactive moiety F is selected from azides or tetrazines. Most preferably, the reactive moiety F is an azide.

In a second preferred embodiment, F is a thiol or precursor thereof. Thiol or precursor thereof F is used in the conjugation reaction to connect the linker-drug construct to the (modified) antibody. F is reactive towards thiol-reactive probe Q in a thiol ligation. The thiol preferably the thiol of the side chain of a cysteine amino acid, which are naturally present within the antibody AB, in which case linker $L^6$ is not present (b=0), although it may also be synthetically introduced, optionally via a linker $L^6$. Thiol precursors in the context of bioconjugation are known in the art, and include disulfides, which may be naturally occurring disulfide bridges present in the antibody or synthetically introduced disulfides, which are reduced as known in the art. Preferably, F is a thiol group of a cysteine side chain.

In a third preferred embodiment, F is an amine or precursor thereof, preferably an amine. Amine or precursor thereof F is used in the conjugation reaction to connect the linker-drug construct to the (modified) antibody. F is reactive towards amine-reactive probe Q in nucleophilic substitution. The amine is typically a primary amine, preferably the amine of the side chain of a lysine amino acid, which are naturally present within the antibody AB, in which case linker $L^6$ is not present (b=0), although it may also be synthetically introduced, optionally via a linker $L^6$. Preferably, F is a primary amine group of a lysine side chain.

Process for Synthesising the Antibody-Conjugate According to General Structure (1)

In a further aspect, the present invention relates to a process for the preparation of the antibody-conjugate according to the invention, the process comprising the step of reacting Q of the compound according to the invention with a reactive group F of an antibody. The compound according to general structure (2), and preferred embodiments thereof, are described in more detail above. The present process occurs under conditions such that Q is reacted with F to covalently link the antibody AB (3) to the payload D. In the process according to the invention, Q reacts with F, forming a covalent connection between the antibody and the compound according to the invention. Complementary reactive groups Q and reactive groups F are known to the skilled person and are described in more detail below.

Any conjugation technique known in the art can be employed to prepare the multifunctional antibody constructs according to the invention. Suitable conjugation techniques include thiol ligation, lysine ligation, cycloadditions (e.g. copper-catalysed click reaction, strain-promoted azide-alkyne cycloaddition, strain-promoted quinone-alkyne cycloaddition). Preferred conjugation techniques used in the context of the present invention include nucleophilic reactions and cycloadditions, preferably wherein the cycloaddition is a [4+2]cycloaddition or a [3+2]cycloaddition and the nucleophilic reaction is a Michael addition or a nucleophilic substitution. Suitable conjugation techniques are for example disclosed in G. T. Hermanson, "Bioconjugate Techniques", Elsevier, 3rd Ed. 2013 (ISBN:978-0-12-382239-0), WO 2014/065661, van Geel et al., *Bioconj. Chem.* 2015, 26, 2233-2242, PCT/EP2021/050594, PCT/EP2021/050598 and NL 2026947.

Thus, in a preferred embodiment of the conjugation process according to the invention, conjugation is accomplished via a nucleophilic reaction, such as a nucleophilic substitution or a Michael reaction. A preferred nucleophilic reaction is the acylation of a primary amino group with an activated ester. A preferred Michael reaction is the maleimide-thiol reaction, which is widely employed in bioconjugation.

Thus, in a preferred embodiment of the conjugation process according to the invention, conjugation is accomplished via a cycloaddition. Preferred cycloadditions are a (4+2)-cycloaddition (e.g. a Diels-Alder reaction) or a (3+2)-cycloaddition (e.g. a 1,3-dipolar cycloaddition). Preferably, the conjugation reaction is the Diels-Alder reaction or the 1,3-dipolar cycloaddition. The preferred Diels-Alder reaction is the inverse-electron demand Diels-Alder cycloaddition. In another preferred embodiment, the 1,3-dipolar cycloaddition is used, more preferably the alkyne-azide cycloaddition, and most preferably wherein Q is or comprises an alkyne group and F is an azido group. Cycloadditions, such as Diels-Alder reactions and 1,3-dipolar cycloadditions are known in the art, and the skilled person knowns how to perform them.

The process according to the present aspect preferably concerns a click reaction, more preferably a 1,3-dipolar cycloaddition, most preferably an alkyne/azide cycloaddition. Most preferably, Q is or comprises an alkyne group and F is an azido group. Click reactions, such as 1,3-dipolar cycloadditions, are known in the art, and the skilled person knows how to perform them.

Thus, the process for preparing the antibody-conjugate according to the invention according to this aspect comprises reacting the modified antibody of structure (3) with a compound according to structure (2), to obtain the antibody-conjugate of structure (1).

In a preferred embodiment, the process for preparing the antibody-conjugate according to the invention comprises:

(i) contacting an antibody comprising y core N-acetylglucosamine (GlcNAc) moieties, wherein y=1, 2, 3 or 4, with a compound of the formula $S(F)_x$—P in the presence of a catalyst, wherein $S(F)_x$ is a sugar derivative comprising x reactive groups F capable of reacting with a reactive group Q, x is 1 or 2 and P is a nucleoside mono- or diphosphate, and wherein the catalyst is capable of transferring the $S(F)_x$ moiety to the core-GlcNAc moiety, to obtain a modified antibody according to Formula (26):

$$AB\text{-}[GlcNAc(Fuc)_w\text{-}S\{F\}_x]_y \quad (26)$$

wherein

AB is an antibody capable of targeting CEA-expressing tumours;

Fuc is fucose;

w is 0 or 1; and (ii) reacting the modified antibody with a compound according to structure (2):

$$Q\text{-}L\text{-}D \quad (2)$$

wherein:

Q is a reactive moiety;

L is a linker that links Z to D;

D is selected from the group consisting of anthracyclines, camptothecins, tubulysins, enediynes, amanitins, duocarmycins, maytansinoids, auristatins, eribulins, BCL-XL inhibitors, hemiasterlins, KSP inhibitors, TLR agonists, indolinobenzodiazepine dimers or pyrrolobenzodiazepine dimers (PBDs), and analogues or prodrugs thereof;

to obtain the antibody-conjugate according to structure (1).

Step (i)

In step (i), an antibody comprising 1, 2, 3 or 4 core N-acetylglucosamine moieties is contacted with a compound of the formula $S(F)_x$—P in the presence of a catalyst, wherein $S(F)_x$ is a sugar derivative comprising x reactive groups F capable of reacting with a reactive group Q, x is 1 or 2 and P is a nucleoside mono- or diphosphate, and wherein the catalyst is capable of transferring the $S(F)_x$ moiety to the core-GlcNAc moiety. Herein, the antibody is typically an antibody that has been trimmed to a core-GlcNAc residue as described further below. Step (i) affords a modified antibody according to Formula (26).

The starting material, i.e. the antibody comprising a core-GlcNAc substituent, is known in the art and can be prepared by methods known by the skilled person. In one embodiment, the process according to the invention further comprises the deglycosylation of an antibody glycan having a core N-acetylglucosamine, in the presence of an endoglycosidase, in order to obtain an antibody comprising a core N-acetylglucosamine substituent, wherein said core N-acetylglucosamine and said core N-acetylglucosamine substituent are optionally fucosylated. Depending on the nature of the glycan, a suitable endoglycosidase may be selected. The endoglycosidase is preferably selected from the group consisting of EndoS, EndoA, EndoE, EfEndo18A, EndoF, EndoM, EndoD, EndoH, EndoT and EndoSH and/or a combination thereof, the selection of which depends on the nature of the glycan. EndoSH is described in PCT/EP2017/052792, see Examples 1-3, and SEQ. ID No: 1, which is incorporated by reference herein.

Structural features S and x are defined above for the antibody-conjugate according to the invention, which equally applies to the present aspect. Compounds of the formula $S(F)_x$—P, wherein a nucleoside monophosphate or a nucleoside diphosphate P is linked to a sugar derivative $S(F)_x$, are known in the art. For example Wang et al., *Chem. Eur. J.* 2010, 16, 13343-13345, Piller et al., *ACS Chem. Biol.* 2012, 7, 753, Piller et al., *Bioorg. Med. Chem. Lett.* 2005, 15, 5459-5462 and WO 2009/102820, all incorporated by reference herein, disclose a number of compounds $S(F)_x$—P and their syntheses. In a preferred embodiment nucleoside mono- or diphosphate P in $S(F)_x$—P is selected from the group consisting of uridine diphosphate (UDP), guanosine diphosphate (GDP), thymidine diphosphate (TDP), cytidine diphosphate (CDP) and cytidine monophosphate (CMP), more preferably P is selected from the group consisting of uridine diphosphate (UDP), guanosine diphosphate (GDP) and cytidine diphosphate (CDP), most preferably P=UDP. Preferably, $S(F)_x$—P is selected from the group consisting of GalNAz-UDP, F2-GalNAz-UDP (N-(azidodifluoro)acetyl-galactosamine), 6-AzGal-UDP, 6-AzGalNAc-UDP (6-azido-6-deoxy-N-acetylgalactosamine-UDP), 4-AzGalNAz-UDP, 6-AzGalNAz-UDP, GlcNAz-UDP, 6-AzGlc-UDP, 6-AzGlcNAz-UDP and 2-(but-3-yonic acid amido)-2-deoxy-galactose-UDP. Most preferably, $S(F)_x$—P is GalNAz-UDP or 6-AzGalNAc-UDP.

Suitable catalyst that are capable of transferring the $S(F)_x$ moiety to the core-GlcNAc moiety are known in the art. A suitable catalyst is a catalyst wherefore the specific sugar derivative nucleotide $S(F)_x$—P in that specific process is a substrate. More specifically, the catalyst catalyses the formation of a β(1,4)-glycosidic bond. Preferably, the catalyst is selected from the group of galactosyltransferases and N-acetylgalactosaminyltransferases, more preferably from the group of β(1,4)—N-acetylgalactosaminyltransferases (GalNAcT) and β(1,4)-galactosyltransferases (GalT), most preferably from the group of β(1,4)-N-acetylgalactosaminyltransferases having a mutant catalytic domain. Suitable catalysts and mutants thereof are disclosed in WO 2014/065661, WO 2016/022027 and WO 2016/170186, all incorporated herein by reference. In one embodiment, the catalyst is a wild-type galactosyltransferase or N-acetylgalactosaminyltransferase, preferably an N-acetylgalactosaminyl-transferase. In an alternative embodiment, the catalyst is a mutant galactosyltransferase or N-acetylgalactosaminyltransferases, preferably a mutant N-acetylgalactosaminyltransferase. Mutant enzymes described in WO 2016/022027 and WO 2016/170186 are especially preferred. These galactosyltransferase (mutant) enzyme catalysts are able to recognize internal sugars and sugar derivatives as an acceptor. Thus, sugar derivative $S(F)_x$ is linked to the core-GlcNAc substituent in step (i), irrespective of whether said GlcNAc is fucosylated or not.

Step (i) is preferably performed in a suitable buffer solution, such as for example phosphate, buffered saline (e.g. phosphate-buffered saline, tris-buffered saline), citrate, HEPES, tris and glycine. Suitable buffers are known in the art. Preferably, the buffer solution is phosphate-buffered saline (PBS) or tris buffer. Step (i) is preferably performed at a temperature in the range of about 4 to about 50° C., more preferably in the range of about 10 to about 45° C., even more preferably in the range of about 20 to about 40° C., and most preferably in the range of about 30 to about 37° C. Step (i) is preferably performed a pH in the range of about 5 to about 9, preferably in the range of about 5.5 to about 8.5, more preferably in the range of about 6 to about 8. Most preferably, step (i) is performed at a pH in the range of about 7 to about 8.

Step (ii)

In step (ii), the modified antibody is reacted with a compound according to general structure (2), comprising a reactive group Q capable of reacting with reactive group F and a payload D, to obtain the antibody-conjugate according to structure (1), containing connecting group Z resulting from the reaction between Q and F. Such reaction occurs under condition such that reactive group Q is reacted with the reactive group F of the biomolecule to covalently link the antibody to the compound according to general structure (2). Step (ii) may also be referred to as the conjugation reaction.

In a preferred embodiment, in step (ii) an azide on an azide-modified antibody reacts with an alkynyl group, preferably a terminal alkynyl group, or a (hetero)cycloalkynyl group of the compound according to general structure (2), via a cycloaddition reaction. This cycloaddition reaction of a molecule comprising an azide with a molecule comprising a terminal alkynyl group or a (hetero)cycloalkynyl group is one of the reactions that is known in the art as "click chemistry". In the case of a linker-conjugate comprising a terminal alkynyl group, said cycloaddition reaction needs to be performed in the presence of a suitable catalyst, preferably a Cu(I) catalyst. However, in a preferred embodiment, the linker-conjugate comprises a (hetero)cycloalkynyl group, more preferably a strained (hetero)cycloalkynyl group. When the (hetero)cycloalkynyl is a strained (hetero) cycloalkynyl group, the presence of a catalyst is not required, and said reaction may even occur spontaneously by a reaction called strain-promoted azide-alkyne cycloaddition (SPAAC). This is one of the reactions known in the art as "metal-free click chemistry".

Application

The invention further concerns a method for the treatment of a subject in need thereof, comprising the administration of the antibody-conjugate according to the invention as defined above. The subject in need thereof is typically a cancer patient. The use of antibody-conjugates, such as antibody-drug conjugates, is well-known in the field of cancer treatment, and the antibody-conjugates according to the invention are especially suited in this respect. The method as described is typically suited for the treatment of cancer. In the method according to this aspect, the antibody-conjugate is typically administered in a therapeutically effective dose. The present aspect of the invention can also be worded as an antibody-conjugate according to the invention for use in the treatment of a subject in need thereof, preferably for the treatment of cancer. In other words, this aspect concerns the use of an antibody-conjugate according to the invention for the preparation of a medicament or pharmaceutical composition for use in the treatment of a subject in need thereof, preferably for use in the treatment of cancer. In the present context, treatment of cancer is envisioned to encompass treating, imaging, diagnosing, preventing the proliferation of, containing and reducing tumours.

This aspect of the present invention may also be worded as a method for targeting CEA-expressing cells, in particular CEA-expressing tumour cells, comprising contacting the antibody-conjugate according to the invention with cells that may possibly be CEA-expressing. The method according to this aspect is thus suitable to determine whether the cells are CEA-expressing. These CEA-expressing cells may be present in a subject, in which case the method comprises administering to a subject in need thereof the antibody-conjugate according to the invention. In a preferred embodiment, the cells that may possibly be CEA-expressing are CEA-expressing cells. The targeting of CEA-expressing cells preferably includes one or more of treating, imaging, diagnosing, preventing the proliferation of, containing and reducing CEA-expressing cells, in particular CEA-expressing tumour cells. The method according to this embodiment may be medical or non-medical. Non-medical methods according to the present aspect may be directed to in vitro or ex vivo targeting CEA-expressing cells, wherein the cells that may possibly be CEA-expressing are present in a sample, e.g. taken from a patient. Such a non-medical method is typically used for the diagnosis of cancer, in particular CEA-positive cancer.

The CEA-expressing cells preferably express CEACAM1, CEACAM3, CEACAM4, CEACAM5, CEACAM6, CEACAM7, CEACAM8, CEACAM16, CEACAM18, CEACAM19, CEACAM20, CEACAM21, most preferably they express CEACAM5. In the context of the present invention, the subject may suffer from a disorder selected from colorectal cancer, gastric cancer, lung cancer, uterine cancer or pancreatic cancer. Thus, the treatment of a subject in need thereof preferably refers to the treatment of colorectal cancer, gastric cancer, lung cancer or uterine cancer.

The inventors have surprisingly found that the antibody-conjugates according to the invention are superior to conventional CEA-targeting antibody-conjugates in terms of safety and/or efficacy, such that the therapeutic index of the antibody-conjugate according to the invention is increased with respect to conventional CEA-targeting antibody-conjugates.

Mode of Conjugation

In the context of the present invention, the "mode of conjugation" refers to the process that is used to conjugate a payload D to an antibody AB, as well as to the structural features of the resulting antibody-conjugate, in particular of the linker that connects the payload to the antibody, that are a direct consequence of the process of conjugation. Thus, in one embodiment, the mode of conjugation refers to a process for conjugation a payload to an antibody. In an alternative embodiment, the mode of conjugation refers to structural features of the linker and/or to the attachment point of the linker to the antibody that are a direct consequence of the process for conjugation a payload to an antibody.

In a further aspect, the invention concerns the use of a mode of conjugation for increasing the therapeutic index of an antibody-conjugate in the treatment of CEA-expressing tumours, wherein the mode of conjugation is being used to connect antibody AB with payload D via a linker L. The mode of conjugation mode of conjugation comprises:

(i) contacting an antibody comprising y core N-acetylglucosamine (GlcNAc) moieties, wherein y=1, 2, 3 or 4, with a compound of the formula $S(F)_x$—P in the presence of a catalyst, wherein $S(F)_x$ is a sugar derivative comprising x reactive groups F capable of reacting with a reactive group Q, x is 1 or 2 and P is a nucleoside mono- or diphosphate, and wherein the catalyst is capable of transferring the $S(F)_x$ moiety to the core-GlcNAc moiety, to obtain a modified antibody according to Formula (26):

$$AB\text{-}[GlcNAc(Fuc)_w\text{-}S\{F\}_x]_y \quad (26)$$

wherein

AB is an antibody capable of targeting CEA-expressing tumours;

Fuc is fucose;

w is 0 or 1; and (ii) reacting the modified antibody with a compound according to structure (2):

$$Q\text{-}L\text{-}D \quad (2)$$

wherein:

Q is a reactive moiety;

L is a linker that links Z to D;

D is selected from the group consisting of anthracyclines, camptothecins, tubulysins, enediynes, amanitins, duocarmycins, maytansinoids, auristatins, eribulins, BCL-XL inhibitors, hemiasterlins, KSP inhibitors, TLR agonists, indolinobenzodiazepine dimers or pyrrolobenzodiazepine dimers (PBDs), and analogues or prodrugs thereof; to obtain the antibody-conjugate according to structure (1)

Preferably, increasing the therapeutic index of an antibody-conjugate is selected from:

(a) increasing the therapeutic efficacy of the antibody-conjugate; and/or (b) increasing the tolerability of the antibody-conjugate.

Increase in therapeutic efficacy of the antibody-conjugates according to the invention may take the form of a reduction in tumour size and/or a prolonged period of regression, when compared to conventional CEA-targeting ADC. Increase in tolerability of the antibody-conjugates according to the invention may take the form of a reduction in signs of toxicity, compared to administration of a CEA-targeting ADC made with a conventional technology. The reduction in sings may also be referred to as a reduction in symptoms or side-effects of cancer treatment, and may involve one or more clinical signs such as reduced reduction in body weight, reduced reduction in mobility, reduced reduction in food intake and/or one or more toxicity parameters, such as improved blood chemistry, hematology, and/or histopathology.

EXAMPLES

General procedure for transient expression and purification of monoclonal antibodies: Various IgGs (tusamitamab, labetuzumab or B12) were transiently expressed in CHO K1 cells by Evitria (Zurich, Switzerland) at 2 L, 250 mL and 5 L scale respectively. The supernatant was purified using a HiTrap MabSelect sure column. The supernatant was loaded onto the column followed by washing with at least 10 column volumes of 25 mM Tris pH 7.5, 150 mM NaCl (TBS). Retained protein was eluted with 0.1 M AcOH pH 2.7. The eluted product was immediately neutralized with 2.5 M Tris-HCl pH 8.8 and dialyzed against 20 mM histidine, 150 mM NaCL, pH 7.5. Next the IgG was concentrated (>20 mg/mL) using a Vivaspin Turbo 15 ultrafiltration unit (Sartorius). The sequences of the IgGs is given here below:

tusamitamab (I) light chain (SEQ ID No. 43):
DIQMTQSPASLSASVDRVTITCRASENIFSYLAWYQQKPGKSPKLLVYNT
RTLAEGVPSRFSGSGSGTDFSLTISSLQPEDFATYYCQHHYGTPFTFGSG
TKLEIKRTVAAPSVFIFPPSDEQLKSGTASVVCLLNNFYPREAKVQWKVD
NALQSGNSQESVTEQDSKDSTYSLSSTLTLSKADYEKHKVYACEVTHQGL
SSPVTKSFNRGEC tusamitamab (I) heavy chain (SEQ ID No. 41):
EVQLQESGPGLVKPGGSLSLSCAASGFVFSSYDMSWVRQTPERGLEWVAY
ISSGGGITYAPSTVKGRFTVSRDNAKNTLYLQMNSLTSEDTAVYYCAAHY
FGSSGPFAYWGQGTLVTVSSASTKGPSVFPLAPSSKSTSGGTAALGCLVK
DYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQ
VYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPG labetuzumab (II) light chain (SEQ ID No. 38):
DIQLTQSPSSLSASVGDRVTITCKASQDVGTSVAWYQQKPGKAPKLLIYW
TSTRHTGVPSRFSGSGSGTDFTFTISSLQPEDIATYYCQQYSLYRSFGQG
TKVEIKRTVAAPSVFIFPPSDEQLKSGTASVVCLLNNFYPREAKVQWKVD
NALQSGNSQESVTEQDSKDSTYSLSSTLTLSKADYEKHKVYACEVTHQGL
SSPVTKSFNRGEC labetuzumab (II) heavy chain (SEQ ID No. 36):
EVQLVESGGGVVQPGRSLRLSCSASGFDFTTYWMSWVRQAPGKGLEWIGE
IHPDSSTINYAPSLKDRFTISRDNAKNTLFLQMDSLRPEDTGVYFCASLY
FGFPWFAYWGQGTPVTVSSASTKGPSVFPLAPSSKSTSGGTAALGCLVKD
YFPEPVTVSWNSGALTSGVHTFPAVLQSSGLYSLSSVVTVPSSSLGTQTY
ICNVNHKPSNTKVDKRVEPKSCDKTHTCPPCPAPELLGGPSVFLFPPKPK
DTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPGK B12 (III) light chain (SEQ ID No. 52):
EIVLTQSPGTLSLSPGERATFSCRSSHSIRSRRVAWYQHKPGQAPRLVIH
GVSNRASGISDRFSGSGSGTDFTLTITRVEPEDFALYYCQVYGASSYTFG
QGTKLERKRTVAAPSVFIFPPSDEQLKSGTASVVCLLNNFYPREAKVQWK
VDNALQSGNSQESVTEQDSKDSTYSLSSTLTLSKADYEKHKVYACEVTHQ
GLSSPVTKSFNRGEC B12 (III) heavy chain (SEQ ID No. 53):
QVQLVQSGAEVKKPGASVKVSCQASGYRFSNFVIHWVRQAPGQRFEWMGW
INPYNGNKEFSAKFQDRVTFTADTSANTAYMELRSLRSADTAVYYCARVG
PYSWDDSPQDNYYMDVWGKGTTVIVSSASTKGPSVFPLAPSSKSTSGGTA
ALGCLVKDYFPEPVTVSWNSGALTSGVHTFPAVLQSSGLYSLSSVVTVPS
SSLGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAK
GQPREPQVYTLPPSRDELTKNQVSLTCLVKGFYPSDIAVEWESNGQPENN
YKTTPPVLDSDGSFFLYSKLTVDKSRWQQGNVFSCSVMHEALHNHYTQKS
LSLSPGK General procedure for analytical RP-UPLC (DTT treated samples): Prior to RP-UPLC analysis, IgG (10 µL, 1 mg/mL in PBS pH 7.4) was added to 12.5 mM DTT, 100 mM TrisHCl pH 8.0 (40 µL) and incubated for 15 minutes at 37° C. The reaction was quenched by adding 49% acetonitrile, 49% water, 2% formic acid (50 µL). RP-UPLC analysis was performed on a Waters Acquity UPLC-SQD. The sample (5 µL) was injected with 0.4 mL/min onto Bioresolve RP mAb 2.1*150 mm 2.7 µm (Waters) with a column temperature of 70° C. A linear gradient was applied in 9 minutes from 30 to 54% acetonitrile in 0.1% TFA and water. Absorbance of eluted peaks was measured at 215 nm followed by automated integration (MassLynx, Waters) to determine reaction conversion.

General procedure for mass spectral analysis of (modified) monoclonal antibodies: Prior to mass spectral analysis, IgG was treated with IdeS, which allows analysis of the Fc/2 fragment. For analysis of both light and heavy chain, a solution of 20 µg (modified) IgG was incubated for 5 minutes at 37° C. with 100 mM DTT in a total volume of 4 µL. If present, azide-functionalities are reduced to amines under these conditions. For analysis of the Fc/2 fragment, a solution of 20 μg (modified) IgG was incubated for 1 hour at 37° C. with IdeS/Fabricator™ (1.25 U/μL) in phosphate-buffered saline (PBS) pH 6.6 in a total volume of 10 μL. Samples were diluted to 80 μL followed by analysis electrospray ionization time-of-flight (ESI-TOF) on a JEOL AccuTOF. Deconvoluted spectra were obtained using Magtran software.

Figure 3:
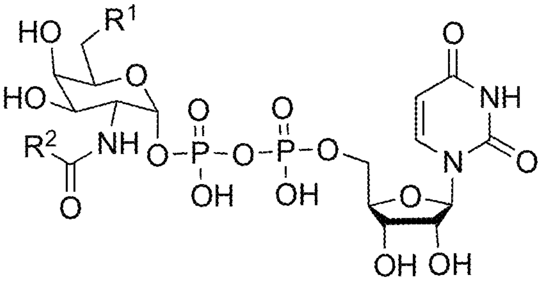
FIG. 3 shows several structures of derivatives of UDP sugars of galactosamine, which may be modified with e.g. a 3-mercaptopropionyl group (2a), an azidoacetyl group (2b), or an azidodifluoroacetyl group (2c) at the 2-position, or with an azido group at the 6-position of N-acetyl galactosamine (2d).
Figure 4:
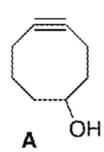
FIG. 4 shows cyclooctynes (A-T) suitable for metal-free click chemistry, which are preferred options for reactive moiety Q.
Figure 4:
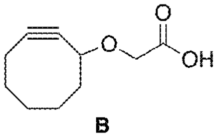
Figure 4:
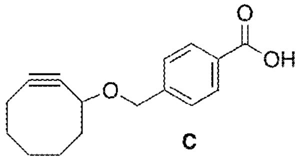
Figure 4:
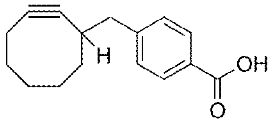
Figure 4:
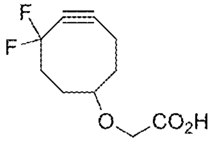
Figure 4:
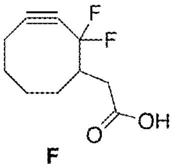
Figure 4:
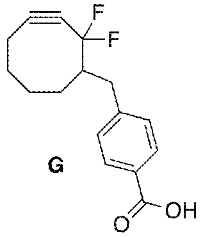
Figure 4:
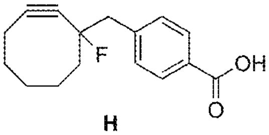
Figure 4:
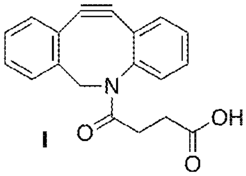
Figure 4:
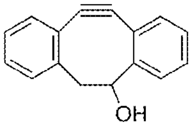
Figure 4:
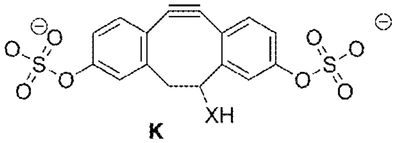
Figure 4:
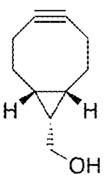
Figure 4:
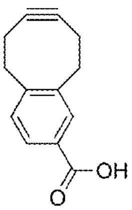
Figure 4:
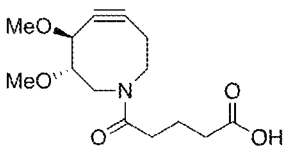
Figure 4:
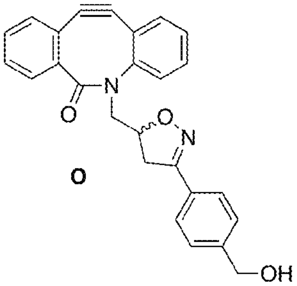
Figure 4:
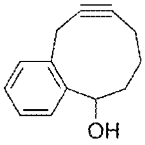
Figure 4:
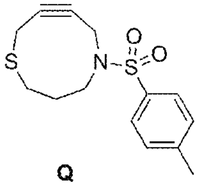
Figure 4:
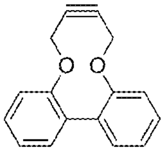
Figure 4:
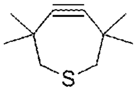
Figure 4:
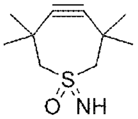
Figure 5:
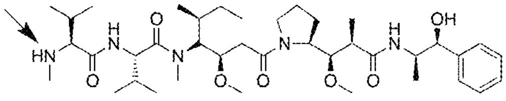
FIG. 5 shows a set of exemplary toxic payloads for conjugation to various CEA-targeting monoclonal antibodies according to the invention. Point of attachment of a linker (to an amino group present in the payload) is indicated with an arrow. Preferred conjugates according to the present invention contain the payloads, including point of attachment, as shown in FIG. 5.
Figure 5:
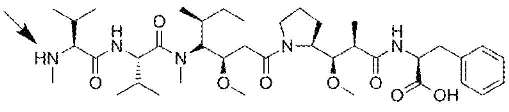
Figure 5:
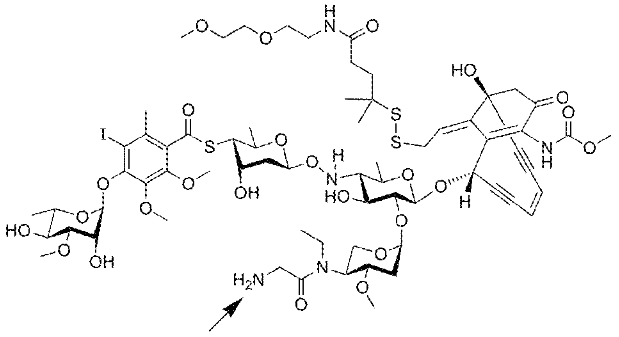
Figure 5:
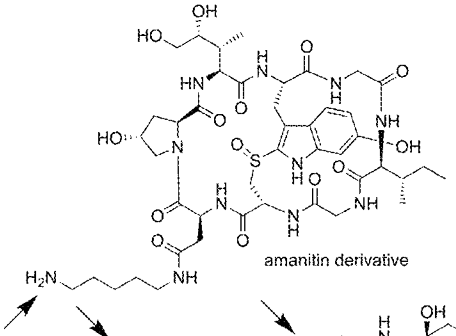
Figure 5:
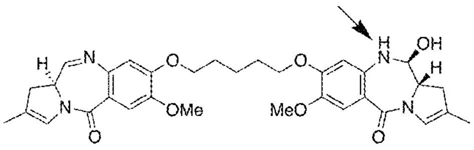
Figure 5:
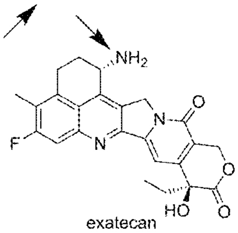
Figure 5:
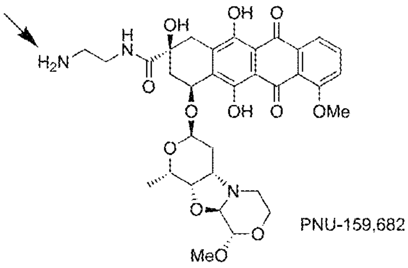
Figure 5:
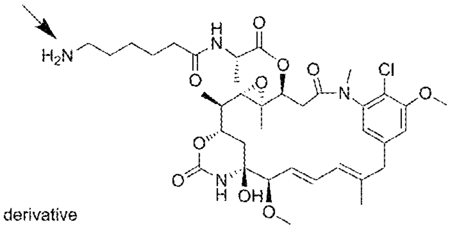

General procedure for enzymatic remodeling of IgG to mAb-(6-$N_3$-GalNAc)$_2$: IgG (15 mg/mL) was incubated with 1% w/w EndoSH (as described in PCT/EP2017/052792, see Examples 1-3, and SEQ. ID No: 1, which is incorporated by reference herein), 3% w/w His-TnGalNAcT (as described in PCT/EP2016/059194, see Examples 3 and 4, and SEQ. ID No: 49, which is incorporated by reference herein), 0.01% AP (Roche) and UDP 6-N3-GalNAc (compound 2d in FIG. 3, 25 eq compared to IgG) in 6 mM $MnCl_2$ and TBS for 16 hours at 30° C. Next, the functionalized IgG was purified using a HiTrap MabSelect sure 5 mL column. After loading of the reaction mixture the column was washed with TBS+ 0.2% triton and TBS. The IgG was eluted with 0.1 M AcOH pH 2.7 and neutralized with 2.5 M Tris-HCl pH 8.8. After three times dialysis to 20 mM histidine, 150 mM NaCl pH 7.5, the IgG was concentrated to 15-20 mg/mL using a Vivaspin Turbo 15 ultrafiltration unit (Sartorius).

Preparation of Azide-Functionalized Antibodies: Examples 1-3

Example 1: Preparation of tusamitamab-(6-$N_3$-GalNAc)$_2$ (I-$N_3$)

According to the general procedure for enzymatic remodeling, tusamitamab was converted to tusamitamab-(6-$N_3$-GalNAc)$_2$ Mass spectral analysis of a sample after IdeS treatment showed one major Fc/2 product (observed mass 24329 Da, approximately 95% of total Fc/2), corresponding to the expected product.

Example 2: Preparation of labetuzumab-(6-$N_3$-GalNAc)$_2$ (II-$N_3$)

According to the general procedure for enzymatic remodeling, labetuzumab was converted to labetuzumab-(6-$N_3$-GalNAc)$_2$ Mass spectral analysis of a sample after IdeS treatment showed one major Fc/2 product (observed mass 24360 Da, approximately 90% of total Fc/2), corresponding to the expected product.

Example 3: Preparation of B12-(6-$N_3$-GalNAc)$_2$ (III-$N_3$)

According to the general procedure for enzymatic remodeling, B12 was converted to B12-(6-$N_3$-GalNAc)$_2$ Mass spectral analysis of a sample after IdeS treatment showed one major Fc/2 product (observed mass 24330 Da, approximately 90% of total Fc/2), corresponding to the expected product.

Examples 4-8: Synthesis of Linker Conjugates 3, 4, 5b and 9

Example 4: Preparation of Compound 11

Compound 10 (163 mg, 240 μmol) was added to a mixture of exatecan mesylate (125 mg, 235 μmol) and DIPEA (61 mg, 82 μL, 0.47 mmol) in dry DMF (0.9 mL). After 20 h, the reaction mixture was diluted to 9 mL DCM and purified by gradient column chromatography (0→40% MeOH/DCM) to afford 11 (155 mg, 159 μmol, 68%). LCMS (ESI+) calculated for $C_{55}H_{54}FN_6O_{10}^+$ (M+H)$^+$ 977.39, found 977.72. In addition to 11, free base of exatecan (82.4 mg, 189 μmol, 20%) was recovered. LCMS (ESI+) calculated for $C_{24}H_{23}FN_3O_4^+$ (M+H)$^+$ 436.46, found 436.54.

Example 5. Preparation of Compound 3

The synthesis of BCN-HS-(va-PABC-Ex)$_2$ (3) is also described in PCT/EP2021/075401 (example 4), incorporated herein. To a solution of compound 11 (155 mg, 159 μmol) in DMF (1.6 mL) were added $Et_3N$ (73 mg, 101 μL, 0.72 mmol) and a solution of compound 12 (65 mg, 72 μmol) in DMF (1.4 mL). The reaction mixture was stirred for 18 h, diluted with DCM (20 mL) and purified by gradient column chromatography (0→40% MeOH/DCM) to afford 3 as a pale-yellow solid (94 mg, 44 μmol, 28%). LCMS (ESI+) calculated for $C_{102}H_{118}F_2N_{16}O_{29}S_2^{2+}$ (M/2$^+$H)$^+$ 1066.88, found 1067.12.

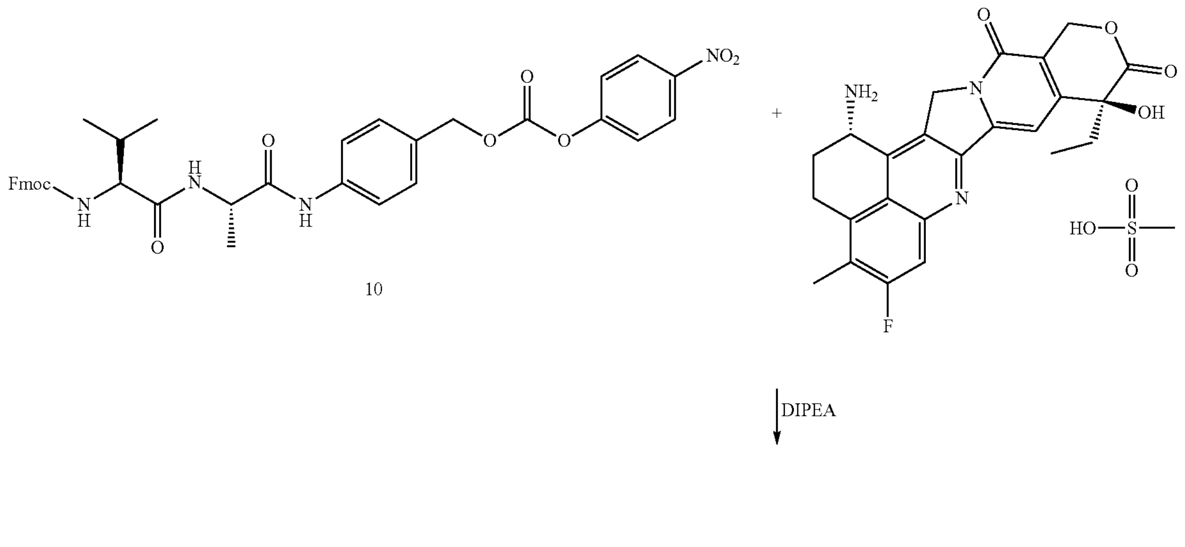

10

-continued
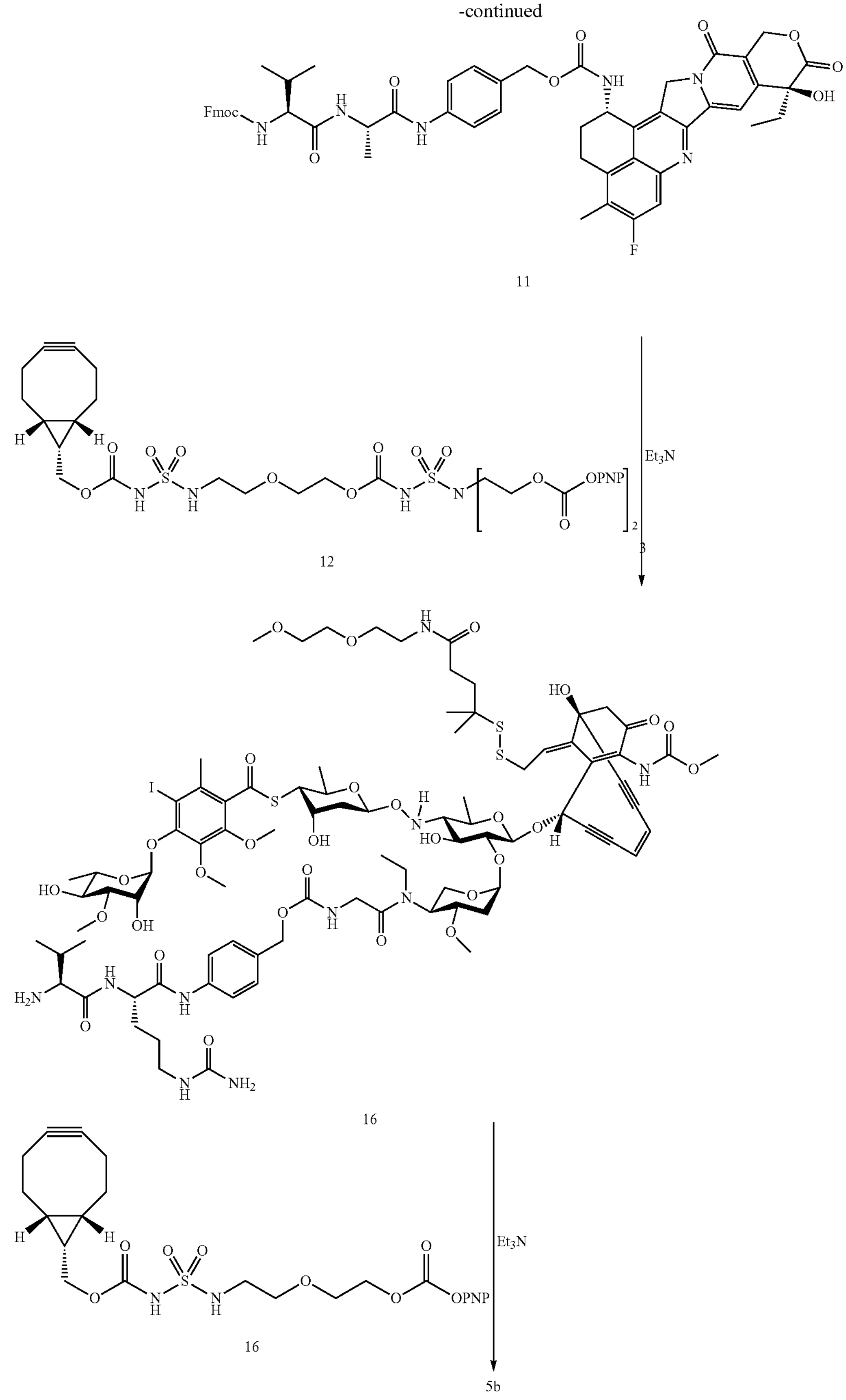
11
12
16
16
5b

Example 6: Synthesis of Linker Conjugate 5b

Compound BCN-HS-vc-PABC-CM (5b) was prepared according to the procedures described in WO2019110725, incorporated herein. A solution of compound 16 (172 μL, 21.5 mg, 38.1 μmol) was added to a solution of compound 15 (190 μL, 82.6 mg, 38.1 μmol, 1.0 equiv.) followed by addition of $Et_3N$ (53 μL, 38.6 mg, 381 μmol, 10.0 equiv.). The reaction was left to stand for 14.5 hours at room temperature. The reaction mixture was diluted with DCM to a volume of 6 mL and then purified by automated silicagel flash chromatography (0%→20% MeOH in DCM) affording unpure product (72.2 mg, 31.0 μmol) as an off-white film. The unpure product was further purified by prepHPLC (30%→90% $CH_3CN/H_2O$+1% $CH_3COOH$, Column Xbridge prep C18 5 um OBD, 30×100 mm, runtime 16 minutes), followed by a $2^{nd}$ purification by automated silicagel flash chromatography (0%→20% MeOH in DCM) affording compound 5b (45.2 mg, 19.4 μmol, yield 47%) as a colorless film. LCMS (ESI+) calculated for $C_{100}H_{1441}N_{11}O_{36}S_4^{2+}$ (M+2H$^+$)/2 1165.39, found 1165.71.

Example 7. Synthesis of Linker Conjugate 6

The synthesis of BCN-HS-PEG2-HS-(vc-PABA-Ahx-May)$_2$ (6) is also described in PCT/NL2015/050697 (example 55), incorporated herein. A solution of 18 (3.9 mg, 4.3 μmol) and $Et_3N$ (3.0 μL, 2.2 mg, 21.5 μmol) in DMF (1 mL) was added to a solution of H-Val-Cit-PABA-Ahx-maytansin 17 (10 mg, 8.6 μmol) in DMF (100 μL). The mixture was allowed to react overnight and concentrated. The residue was purified via reversed phase (C18) HPLC chromatography (30→90% MeCN, 1% AcOH) in $H_2O$ (1% AcOH) to give product 6 (3.9 mg, 1.32 μmol, 31%). LRMS (ESI$^+$) m/z calcd for $C_{136}H_{196}Cl_2N_{22}O_{43}S_2$ (M+2H$^+$)/2=1480.13; found 1480.35. As a side-product, the mono-substituted Ahx-maytansin derivative of 6 was isolated (not depicted). LRMS (ESI$^+$) calcd for $C_{85}H_{119}ClN_{14}O_{31}S_2^{2+}$ m/z 965.36 found 965.54.

Example 8. Preparation of Compound 9

A solution of BCN-HS-PEG$_2$-b-(Glu(OFm)—OH)$_2$ (8, 12.1 mg, 10 μmol, 1.0 eq) dissolved in anhydrous DMF (180 μL) was added to a solution of $NH_2$-Val-Ala-PABC-exatecan (5b, Fmoc-deprotected 5, 19 mg, 25 μmol, 2.5 eq) in anhydrous DCM (180 μL), DIPEA (11 μL, 63 μmol, 6.2 eq) and HATU (8.9 mg, 23 μmol, 2.3 eq). After stirring for 2 h at room temperature, the reaction mixture was further diluted with DCM (800 μL) and purified by flash column chromatography over silicagel (0%→20% MeOH in DCM) to give the product as a clear oil (difficult to determine yield due to presence of DMF). LCMS (ESI+) calculated for $C_{140}H_{150}F_2N_{17}O_{33}S^+$ (M/2$^+$H$^+$) 1334.01, found 1334.79.

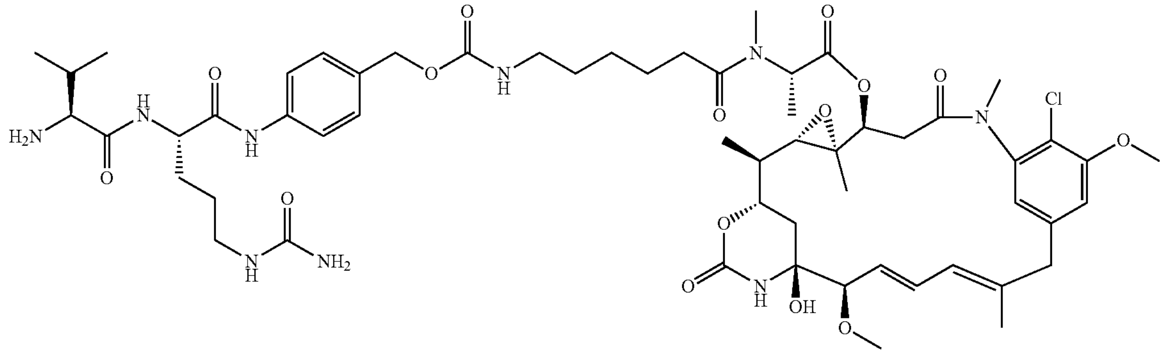

17

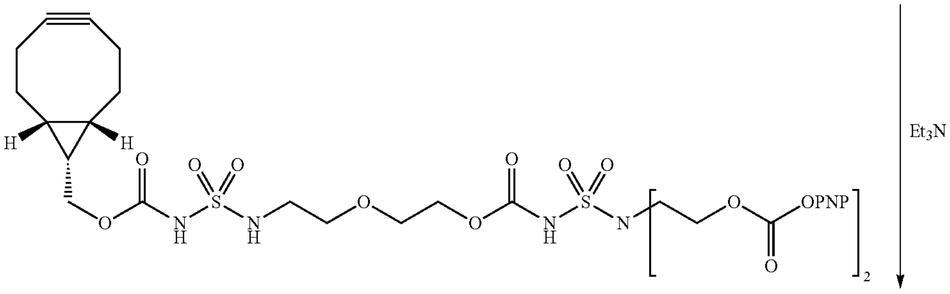

18

6

This compound was dissolved in DMF (300 μL) and triethylamine (21 μL, 150 μmol, 15 eq) was added. After 17 h at room temperature, the reaction mixture was diluted with DCM (700 μL) and purified by flash column chromatography over silicagel (0%→45% MeOH in DCM) to give compound 9 in 44% yield as a yellow solid (10.2 mg, 4.4 μL). LCMS (ESI+) calculated for $C_{112}H_{130}F_2N_{17}O_{33}S^+$ (M/2$^+$H$^+$) 1156.2, found 1156.74.

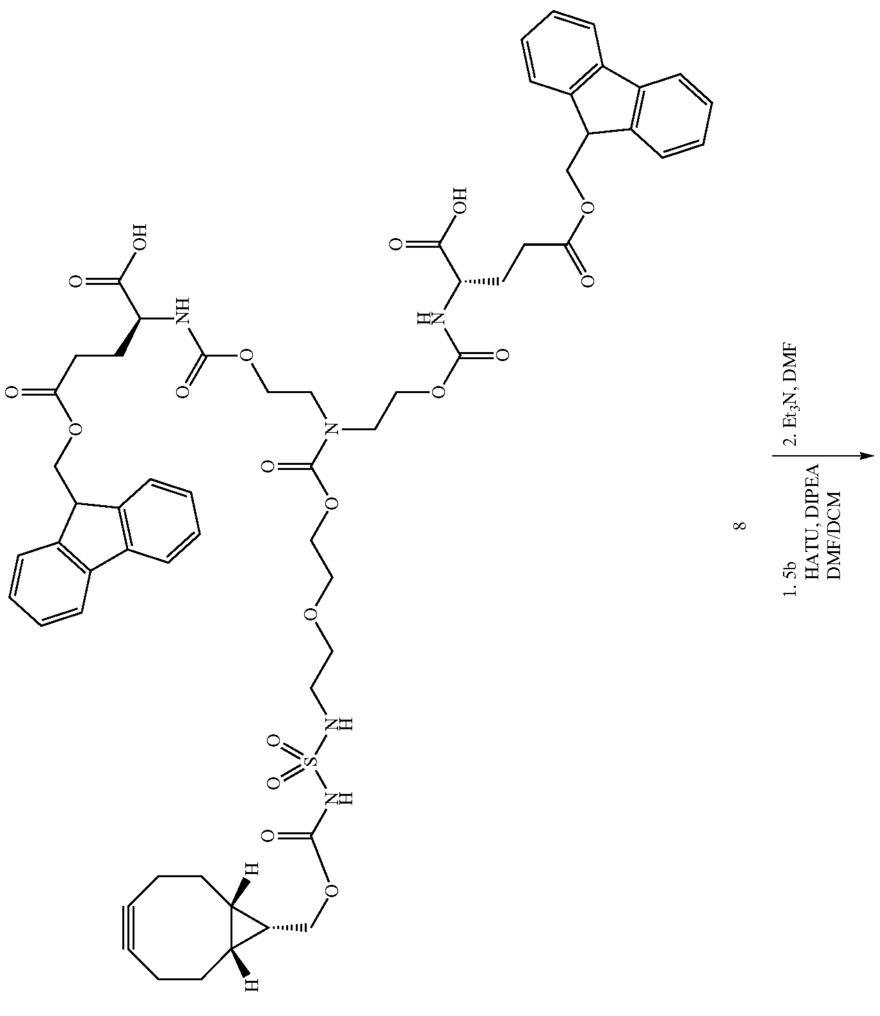
8
1. 5b
HATU, DIPEA
DMF/DCM
2. $Et_3N$, DMF

-continued
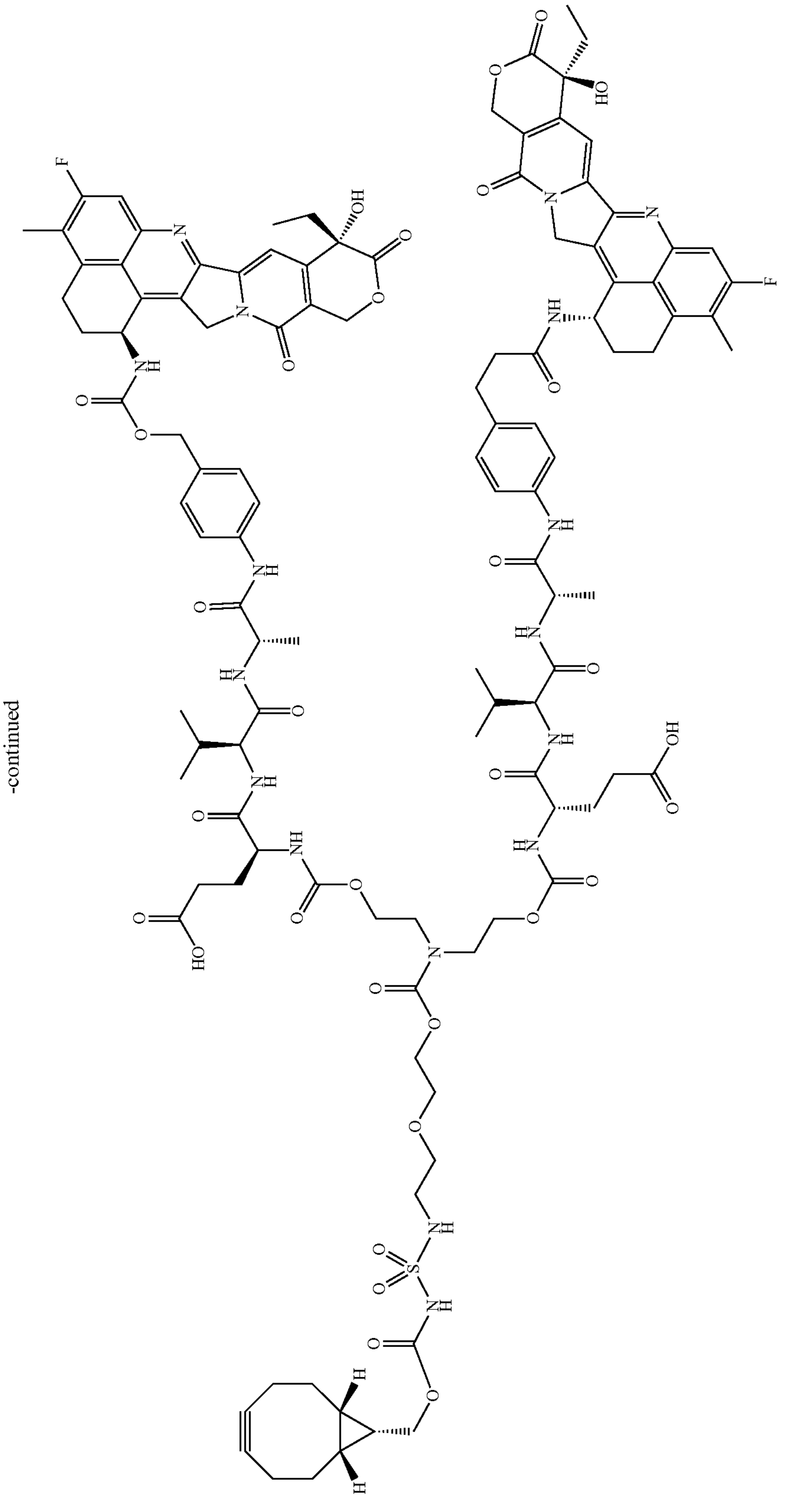
9

Examples 9-15: Conjugation of Linker-Payloads to (Modified) Monoclonal Antibodies Example 9: Conjugation of labetuzumab(6-$N_3$-GalNAc)$_2$ with BCN-HS-PEG2-HS-(va-PAB-Ex)$_2$ 3 to Obtain Conjugate Labetuzumab-3

To a solution of labetuzumab(6-$N_3$-GalNAc)$_2$ (844 μL, 18.0 mg, 23.71 mg/ml in TBS pH 7.5) was added sodium deoxycholate (200 μL, 110 mM) and BCN-HS-PEG2-HS-(va-PAB-Ex)$_2$ 3 (53 μL, 10 mM solution in DMF) and propylene glycol (547 μL). The reaction was incubated overnight at rt. Next the conjugate was purified on a HiLoad 16/600 Superdex200 PG column (Cytiva) on an AKTA Pure (Cytiva). To remove the excess of free payload, 4 mg of active charcoal (Carbon RHC, Filtrox AG) was added and rotated for 3 h. The charcoal was removed by centrifugation and subsequently filtered over a PES syringe filter (pore 0.20 μm, Corning). Subsequently the solution was buffer exchanged using a HiTrap 26-10 desalting column (Cytiva), rinsed with 0.1M NaOH and equilibrated with 20 mM histidine, 6% sucrose buffer pH 6.0, and concentrated using a Vivaspin Turbo 4 10 kDa MWCO ultrafiltration unit (Sartorius). 0.04% Tween-20 was added before filter sterilization. Mass spectral analysis of the sample after IdeS treatment showed one major Fc/2 product (observed mass 26492 Da, approximately 90% of total Fc/2), corresponding to the conjugate labetuzumab-3. RP-UPLC analysis of the sample under reducing conditions showed an average DAR of 3.90.

Example 10: Conjugation of tusamitamab(6-$N_3$-GalNAc)$_2$ with BCN-HS-PEG2-HS-(va-PAB-Ex)$_2$3 to Obtain Conjugate Tusamitamab-3

To a solution of tusamitamab(6-$N_3$-GalNAc)$_2$ (1762 μL, 37.0 mg, 21.06 mg/ml in TBS pH 7.5) was added sodium deoxycholate (247 μL, 110 mM) and BCN-HS-PEG2-HS-(va-PAB-Ex)$_2$ 3 (74 μL, 10 mM solution in DMF) and propylene glycol (421 μL). The reaction was incubated overnight at rt. Next the conjugate was purified on a HiLoad 16/600 Superdex200 PG column (Cytiva) on an AKTA Pure (Cytiva). To remove the excess of free payload, 19 mg of active charcoal (Carbon RHC, Filtrox AG) was added and rotated for 3 h. The charcoal was removed by centrifugation and subsequently filtered over a PES syringe filter (pore 0.20 μm, Corning). Subsequently the solution was buffer exchanged using a HiTrap 26-10 desalting column (Cytiva), rinsed with 0.1M NaOH and equilibrated with 20 mM histidine, 6% sucrose buffer pH 6.0, and concentrated using a Vivaspin Turbo 4 10 kDa MWCO ultrafiltration unit (Sartorius). 0.04% Tween-20 was added before filter sterilization. Mass spectral analysis of the sample after IdeS treatment showed one major Fc/2 product (observed mass 26461 Da, approximately 90% of total Fc/2), corresponding to the conjugate tusamitamab-3. RP-UPLC analysis of the sample under reducing conditions showed an average DAR of 3.89.

Example 11: Conjugation of tusamitamab(6-$N_3$-GalNAc)$_2$ with BCN-HS-vc-PABC-calicheamicin 5b to Obtain Conjugate Tusamitamab-5b To a solution of tusamitamab(6-$N_3$-GalNAc)$_2$ (1424 μL, 30.0 mg, 21.06 mg/ml in TBS pH 7.5) was added sodium deoxycholate (200 μL, 110 mM) and BCN-HS-vc-PABC-calicheamicin 5b (15 μL, 40 mM solution in DMF) and DMF (185 μL). The reaction was incubated overnight at rt. Next the conjugate was purified on a HiLoad 16/600 Superdex200 PG column (Cytiva) on an AKTA Pure (Cytiva). Subsequently the solution was buffer exchanged using a HiTrap 26-10 desalting column (Cytiva), rinsed with 0.1 M NaOH and equilibrated with 20 mM histidine, 6% sucrose buffer pH 6.0, and concentrated using a Vivaspin Turbo 4 10 kDa MWCO ultrafiltration unit (Sartorius). 0.04% Tween-20 was added before filter sterilization. Mass spectral analysis of the sample after IdeS treatment showed one major Fc/2 product (observed mass 26715 Da, approximately 90% of total Fc/2), corresponding to the conjugate tusamitamab-5b. RP-UPLC analysis of the sample under reducing conditions showed an average DAR of 1.94.

Example 12: Conjugation of tusamitamab(6-$N_3$-GalNAc)$_2$ with BCN-HS-PEG2-HS-(vc-PABA-Ahx-May)$_2$ 6 to Obtain Conjugate Tusamitamab-6

To a solution of tusamitamab(6-$N_3$-GalNAc)$_2$ (1424 μL, 30.0 mg, 21.06 mg/ml in TBS pH 7.5) was added BCN-HS-PEG2-HS-(vc-PABA-Ahx-May)$_2$ 6 (80 μL, 10 mM solution in DMF) and DMF (420 μL). The reaction was incubated overnight at rt. Next the conjugate was purified on a HiLoad 16/600 Superdex200 PG column (Cytiva) on an AKTA Pure (Cytiva). Subsequently the solution was buffer exchanged using a HiTrap 26-10 desalting column (Cytiva), rinsed with 0.1M NaOH and equilibrated with 20 mM histidine, 6% sucrose buffer pH 6.0, and concentrated using a Vivaspin Turbo 4 10 kDa MWCO ultrafiltration unit (Sartorius). 0.04% Tween-20 was added before filter sterilization. Mass spectral analysis of the sample after IdeS treatment showed one major Fc/2 product (observed mass 27289 Da, approximately 90% of total Fc/2), corresponding to the conjugate tusamitamab-6. RP-UPLC analysis of the sample under reducing conditions showed an average DAR of 3.85.

Example 13: Conjugation of B12(6-$N_3$-GalNAc)$_2$ with BCN-HS-PEG2-HS-(va-PAB-Ex)$_2$ 3 to Obtain Conjugate B12-3

To a solution of B12(6-$N_3$-GalNAc)$_2$ (6.33 mL, 150.0 mg, 23.71 mg/ml in TBS pH 7.5) was added BCN-HS-PEG2-HS-(va-PAB-Ex)$_2$ 3 (495 μL, 10 mM solution in DMF) and propylene glycol (7.0 mL). The reaction was incubated overnight at rt. Next the conjugate was purified on a HiLoad 26/600 Superdex200 PG column (Cytiva) on an AKTA Pure (Cytiva). To remove the excess of free payload, 150 mg of active charcoal (Carbon RHC, Filtrox AG) was added and rotated overnight. The charcoal was removed by centrifugation and subsequently filtered over a PES syringe filter (pore 0.20 μm, Corning). Subsequently the solution was dialysed to 20 mM histidine, 6% sucrose buffer pH 6.0 for two hours at rt and overnight at 4° C. The solution was concentrated using a Vivaspin Turbo 4 10 kDa MWCO ultrafiltration unit (Sartorius) and 0.04% Tween-20 was added before filter sterilization. Mass spectral analysis of the sample after IdeS treatment showed one major Fc/2 product (observed mass 26462 Da, approximately 90% of total Fc/2), corresponding to the conjugate B12-3. RP-UPLC analysis of the sample under reducing conditions showed an average DAR of 3.75.

Example 14: Production of Tusamitamab-DM4

Tusamitamab (17.5 mg, 2.11 mg/ml in PBS) was charged with DMA to give 5% v/v and 7 molar equivalents SPDB- DM4 (20 mM in DMA) and incubated at rt overnight. The conjugate was purified by preparative SEC (HiLoad 26/600 Superdex pg) into 20 mM histidine/80 mM NaCl/6% sucrose. Concentration and buffer exchange into 20 mM histidine/6% sucrose/pH 6 was performed via discontinuous diafiltration in Vivaspins. 0.04% Tween-20 was added before filter sterilization. The average DAR was measured and was 3.4.

Example 15: Conjugation of labetuzumab(6-$N_3$-GalNAc)$_2$ with BCN-HS-PEG2-(eva-PAB-Ex)$_2$ 9 to Obtain Conjugate Labetuzumab-9

To a solution of labetuzumab(6-$N_3$-GalNAc)$_2$ (26 μL, 0.5 mg, 19.35 mg/ml in TBS pH 7.5) was added sodium deoxycholate (5 μL, 110 mM) and BCN-HS-PEG2-(eva-PAB-Ex)$_2$ 9 (1 μL, 10 mM solution in DMF) and propylene glycol (9 μL). The reaction was incubated overnight at rt. Mass spectral analysis of the sample after IdeS treatment showed one major Fc/2 product (observed mass 26674 Da, approximately 95% of total Fc/2), corresponding to the conjugate labetuzumab-9. RP-UPLC analysis of the conjugate under reducing conditions showed an average DAR of 3.88.

Examples 16-19: In Vitro Studies

Figure 9:
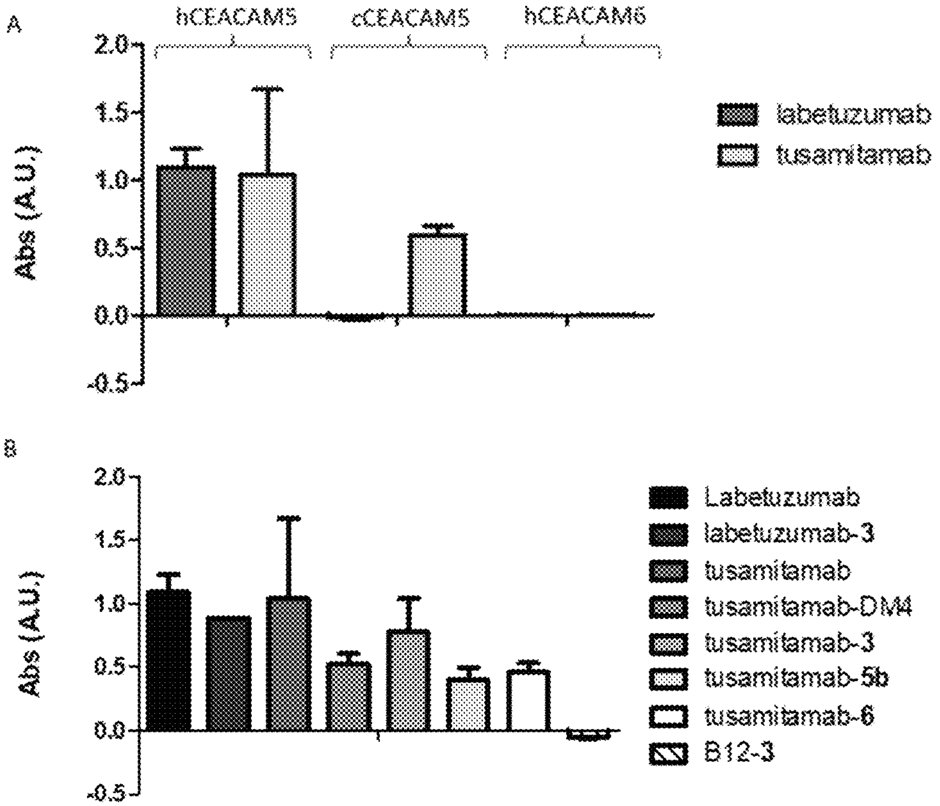
FIG. 9 shows: (A) binding of tusamitamab and labetuzumab to hCEACAM5 (hCD66e), cCEACAM5 (cCD66e) and hCEACAM6 (hCD66c) corrected for the background. Both mAbs show similar affinity for hCEACAM5, do not show any binding to hCEACAM6 and only tusamitamab shows affinity for cCEACAM5 and (B) shows binding of tusamitamab and labetuzumab-based ADCs to hCEACAM5. All ADCs still show binding to hCEACAM5, comparable to the corresponding mAb.

Example 16. hCEACAM5, cCEACAM5 and hCEACAM6 Binding Assay to mAbs and ADCs Using ELISA Nickel NTA plates (Pierce™ Nickel coated plated, ThermoScientific™) were washed three times prior to use. Human CEACAM5 (CD66e protein, His Tag, Sino Biological), human CEACAM6 (CD66c protein, His Tag, Sino Biological) and cynomolgus CEACAM5 (CD66e protein, His Tag, Sino Biological) were dissolved at a concentration of 0.05 μg/mL in 0.1% BSA in PBS (PBA). 100 μL was added to each well and incubated while shaking for 1 hour at room temperature. After removal, the plate was washed 3× with 0.05% Tween-20 in PBS (washing buffer). ADCs were diluted in 0.1% PBA to a final concentration of 8 μg/mL and 100 μL was added to each well (in triplo). ADCs were incubated for 1 h at room temperature. Prior to the addition of 100 μL 1:100 dilution of secondary antibody (Goat anti-human IgG, HRP conjugate, Invitrogen) the plate was washed 3× with washing buffer. The plate was incubated again for 1 h at room temperature and subsequently washed 3× with washing buffer and 3× with PBS. Finally, 100 μL TMB ELISA substrate (1 Step™ Turbo TMB ELISA substrate, ThermoScientific™) was added and incubated for 1 minute. The absorbance of the colorimetric signal was measured with Infinite® M1000 (Tecan) at 605 nm. Data was plotted corrected for the background (see FIGS. 9).

Example 17: In Vitro Cytotoxicity

MKN-45 (CEACAM+, DSMZ ACC-409) cells were diluted in 80% RPMI 1640+20% FBS. The cells were dispensed in a 384-well plate, at a density of 200 cells per well in 45 μl medium. The margins of the plate were filled with phosphate-buffered saline. Plated cells were incubated in a humidified atmosphere of 5% CO2 at 37° C. After 24 hours, 5 μl of compound dilution was added and plates were further incubated. At t=end, 24 μl of ATPlite 1Step™ (PerkinElmer) solution was added to each well, and subsequently shaken for 2 minutes. After 5 minutes of incubation in the dark, the luminescence was recorded on an Envision multimode reader (PerkinElmer).

Controls: t=0 signal. On a parallel plate, 45 μl cells were dispensed and incubated in a humidified atmosphere of 5% CO2 at 37° C. After 24 hours 5 μl DMSO-containing HEPES buffer and 24 μl ATPlite 1 Step™ solution were mixed, and luminescence measured after 5 minutes incubation (=luminescence$_{t=0}$). Cell growth control. The cellular doubling times of all cell lines are calculated from the t=0 hours and t=end growth signals of the untreated cells. If the doubling time is out of specification (0.5-2.0 times deviating from historic average) the assay is invalidated. Maximum signals. For each cell line, the maximum luminescence was recorded after incubation until t=end without compound in the presence of 0.4% DMSO (=luminescence$_{untreated,t=end}$).

Figure 10:
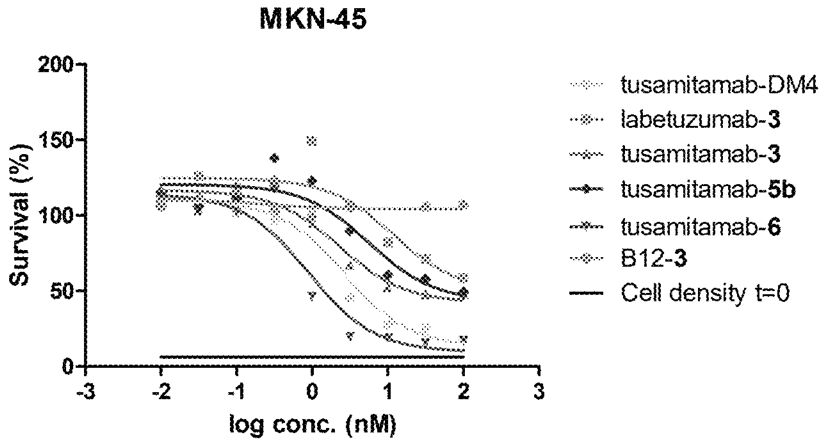
FIG. 10 shows the cytotoxicity data on CEACAM5 expressing MKN-45 cells. All ADCs, except negative control B12-3, induce cytotoxicity with increasing concentrations.

Data analysis: IC50s were calculated by non-linear regression using IDBS XLfit 5. The percentage growth after incubation until t=end (%-growth) was calculated as follows: 100%×(luminescence$_{t=end}$/luminescence$_{untreated,t=end}$). This was fitted to the $^{10}$ log compound concentration (conc) by a 4-parameter logistics curve: %-growth=bottom+(top−bottom)/(1+$10^{(log\ IC50-conc)*hill}$)) where hill is the Hill-coefficient, and bottom and top the asymptotic minimum and maximum cell growth that the compound allows in that assay. Survival plots show data normalized to cell viability percentage by setting wells without cells at 0% viability and wells with untreated cells at 100% viability (see FIG. 10). $IC_{50}$ values for ADCs are shown in the table below:

TABLE 1

$IC_{50}$ values for several ADCs and mAbs for MKN-45 cells

| | MKN-45, $IC_{50}$ (nM) |
|---|---|
| labetuzumab-3 | 6.5 |
| tusamitamab-DM4 | 2.6 |
| tusamitamab-3 | 3.4 |
| tusamitamab-5b | 1.9 |
| tusamitamab-6 | 0.88 |
| B12-3 | >100 |

Example 18. Human and Mouse Serum Stability

Stability of ADCs in mice and human plasma was tested. Prior to the assay, the plasma was depleted from all IgG using CaptivA® Protein A agarose (1 mL agarose/mL serum). ADCs were added to the depleted human/mouse serum to a final concentration of 0.1 mg/mL followed by incubation at 37° C. At each time point, 0.5 mL was snap frozen and stored at −80° C. until further analysis. To isolate the ADCs after incubation, 20 μl CaptivA® Protein A agarose resin was added to the samples and incubated for 1 hour at room temperature. The resin was washed three times with PBS and subsequently 0.1 M Glycine-HCl pH 2.7 (0.4 mL) was added to elute the ADCs. After elution, the samples were immediately neutralized with 1.0 M Tris pH 8.0 (0.1 mL). The samples were spin-filtered against PBS for three times using Amicon Ultra spin-filter 0.5 mL MWCO 10 kDa (Merck Millipore) and the volume was reduced to 40 μL, yielding a final ADC concentration of approximately 1 mg/mL. Samples were analyzed on RP-UPLC (DTT reduced) at specific days to determine the DAR and the results are shown in the table below. At t=14 days, the difference with t=0 days is given in percentage.

TABLE 2

| Stability in human and mouse plasma | | | | | |
|---|---|---|---|---|---|
| Plasma | Conjugate | DAR t = 0 | DAR t = 3 | DAR t = 7 | DAR t = 14 |
| Human | Tusamitamab-DM4 | 3.40 | 3.30 | 3.10 | 3.00 (88%) |
| Human | labetuzumab-3 | 3.90 | 3.86 | 3.79 | 3.70 (95%) |
| Mouse | Tusamitamab-DM4 | 3.40 | 3.35 | 3.13 | 3.21 (94%) |
| Mouse | labetuzumab-3 | 3.84 | 3.78 | 3.78 | 3.69 (96%) |

Example 19. Thermostability in Physiological and Enhance Stress Conditions

The stability of ADCs was tested at elevated temperatures either at physiological conditions (PBS, pH 7.4, 37° C.) or enhanced stress conditions (citrate buffered saline, CBS, pH 5.0, 40° C.). The ADCs were buffer exchanged using a HiTrap 26-10 desalting column (Cytiva), rinsed with 0.1M NaOH and equilibrated with either PBS or CBS on an AKTA Pure (Cytiva). The solution was concentrated using a Vivaspin Turbo 4 10 kDa MWCO ultrafiltration unit (Sartorius) to a concentration >1 mg/mL. The concentration of the ADCs was measured, they were diluted to 1 mg/mL and the first measurement, t=0, was taken for SE-HPLC analysis as described above. The samples were placed at either 37° C. or 40° C. and samples were taken at several timepoints t (in days) and aggregation levels were determined, see tables below.

TABLE 3

| Physiological conditions, monomer levels (in percentage): | | | | | | | | |
|---|---|---|---|---|---|---|---|---|
| | t = 0 | t = 1 | t = 2 | t = 5 | t = 7 | t = 14 | t = 21 | t = 28 |
| Tusamitamab-DM4 | 99.0% | 99.0% | 99.0% | 98.9% | 98.7% | 96.8% | 97.0% | 95.0% |
| labetuzumab-3 | 98.5% | 98.7% | 98.5% | 98.9% | 98.0% | 99.0% | 98.6% | 98.4% |

TABLE 3

| Enhanced stress conditions, monomer levels (in percentage): | | | | | | | | |
|---|---|---|---|---|---|---|---|---|
| | t = 0 | t = 1 | t = 2 | t = 5 | t = 7 | t = 14 | t = 21 | t = 28 |
| Tusamitamab-DM4 | 99.0% | 85.3% | 89.3% | 83.6% | 80.3% | 75.5% | 70.5% | 62.5% |
| labetuzumab-3 | 98.8% | 98.5% | 99.0% | 98.4% | 98.6% | 08.7% | 98.4% | 97.7% |

Examples 20-23: In Vivo Studies

Example 20: In Vivo Efficacy Study

Fragments of the patient-derived tumors, frozen in DMSO/SVF/RPMI 1640 medium (5/10/85) and stored in liquid nitrogen, were thawed at 37° C. for 5 min. Then they were rinsed twice in RPMI 1640 medium before subcutaneous implantation in immunodeficient mice and then serially transplanted in immunodeficient mice. The CR-IGR-034P, a colorectal PDX cell line was amplified in fifteen healthy female CB17 SCID (CB17/lcr-Prkdcscid/lcrlcoCrl) mice, 6-weeks old at reception (obtained from Charles River), by implantation subcutaneously into the right flank of each animal. When tumor volumes reached 500-1500 $mm^3$, tumors were surgically excised for the engraftment.

CB17 SCID mice (female) of 6-7 weeks old (obtained from Charles River) received a subcutaneous injection in the right flank region with tumor fragments amplified as described above. When tumors reached an average size of 100-200 $mm^3$, randomization was performed into 10 groups of 8 mice and treatment began. Homogeneity between groups was tested by an analysis of variance (ANOVA).

The test article administration was performed via intravenous injection through tail vein, and the dosing volume was 10 mL/kg. Treatment was initiated on the same day of randomization. Dosing was conducted in a Laminar Flow Cabinet.

After tumor cells inoculation, the animals were checked daily for morbidity and mortality. At the time of routine monitoring, the animals are checked for any adverse effects of tumor growth and treatments on normal behavior such as mobility, visual estimation of food and water consumption, body weight gain/loss, eye/hair matting and any other abnormal effects and are recorded in the Vivo Manager database (Biosystemes, France). Tumor volumes are measured every 3-4 days in two dimensions using an caliper, and the volume data are expressed in $mm^3$ using the formula: V=(L×W×W)/2, where V is tumor volume, L is tumor length (the longest tumor dimension) and W is tumor width (the longest tumor dimension perpendicular to L). Dosing as well as tumor and body weight measurements will be conducted in a Laminar Flow Cabinet. The endpoint of the experiment is a tumor volume of 2,000 $mm^3$, body weight loss over 20% or 28 days, whichever comes first.

TABLE 5

| Overview of test items and dose levels included in in vivo study | | | | |
|---|---|---|---|---|
| Test item | Dose levels (mg/kg) | Group (N = 8) | Administration | Dosing Schedule |
| vehicle | — | 1 | IV | Single dose |
| tusamitamab-DM4 | 5.7 | 2 | IV | Single dose |
| labetuzumab-3 | 5 | 3 | IV | Single dose |
| | 10 | 4 | IV | Single dose |
| tusamitamab-3 | 5 | 5 | IV | Single dose |
| | 10 | 6 | IV | Single dose |
| tusamitamab-5b | 3 | 8 | IV | Single dose |
| | 5 | 9 | IV | Single dose |
| tusamitamab-6 | 5 | 7 | IV | Single dose |
| B12-3 | 10 | 10 | IV | Single dose |

Figure 11:
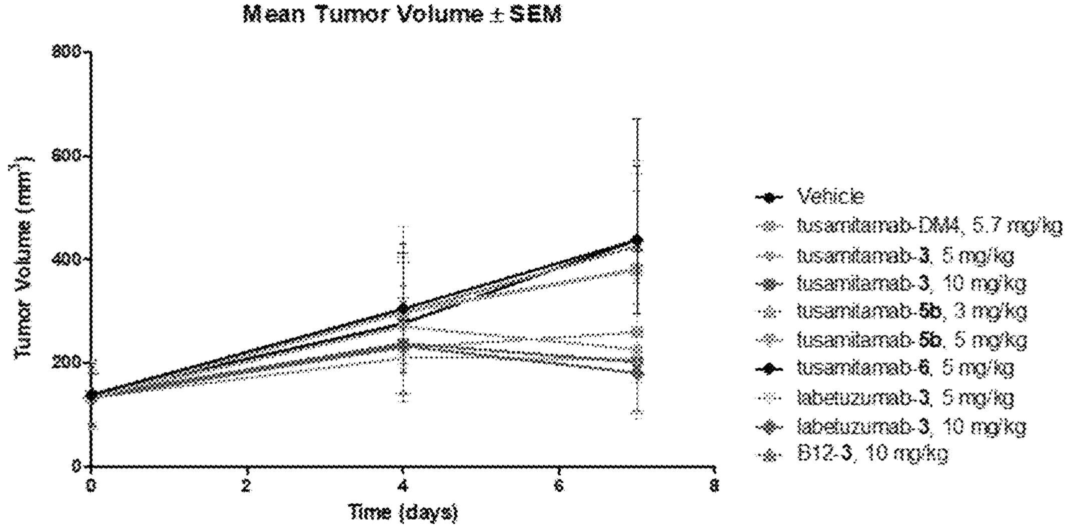
FIG. 11 shows: (A) the in vivo efficacy data of the colorectal IGR-034P PDX model and (B) the body weight plot. First effects of tumour regression is observed for both tusamitamab-3 and labetuzumab-3 after 7 days.
Figure 11:
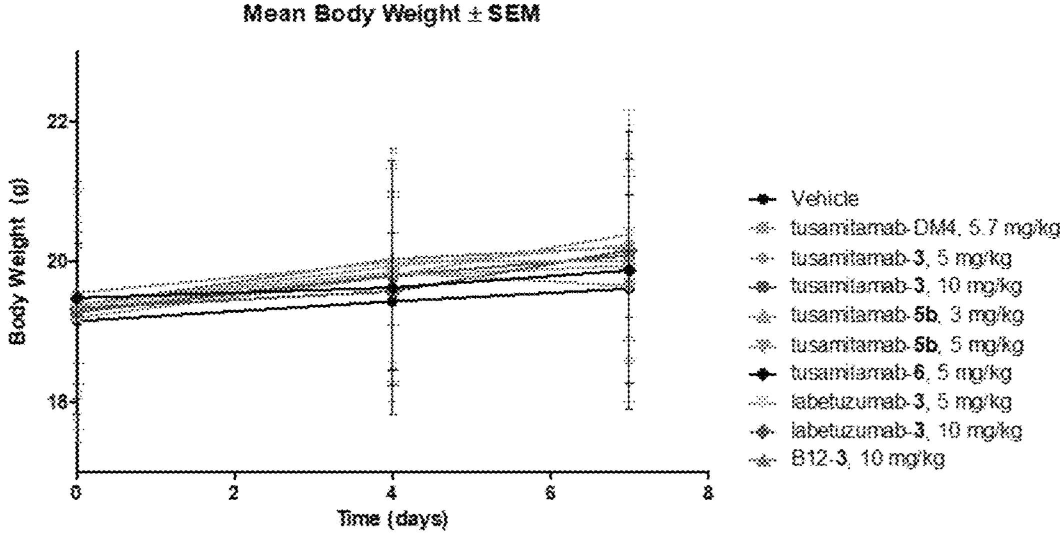
Figure 11C:
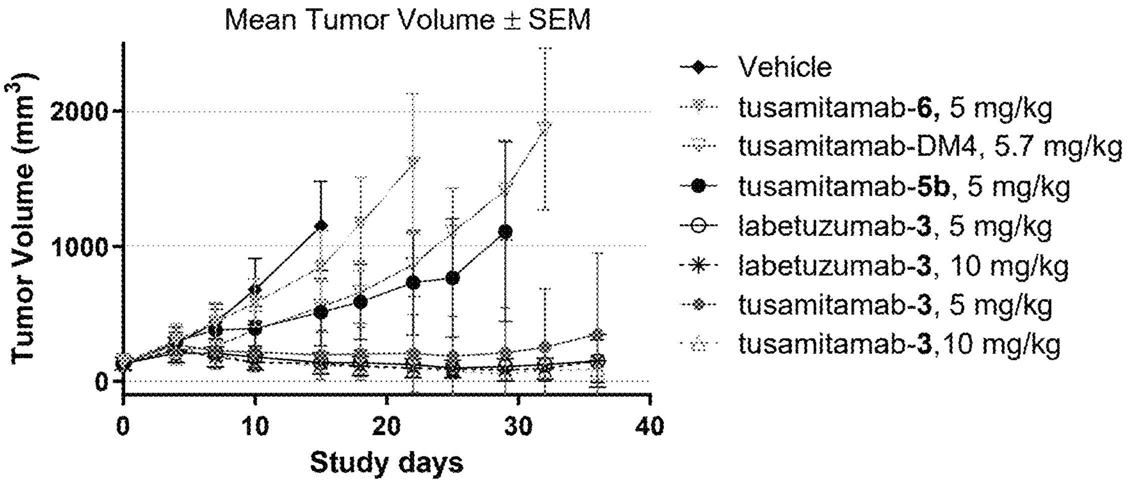
FIGS. 11C and 11D show the same plots for the full experiment (35 days).
Figure 11D:
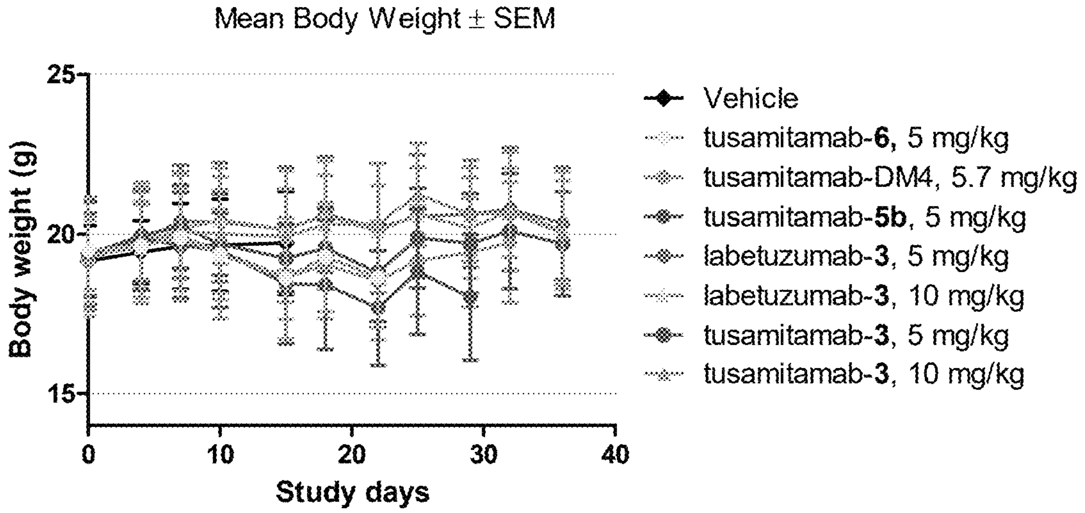

Data for efficacy study with the test items above is depicted in FIGS. 11-11*d*.

Example 21: In Vivo Efficacy Study

Fragments of the patient-derived tumors, frozen in DMSO/SVF/RPMI 1640 medium (5/10/85) and stored in liquid nitrogen, were thawed at 37° C. for 5 min. Then they were rinsed twice in RPMI 1640 medium before subcutaneous implantation in immunodeficient mice and then serially transplanted in immunodeficient mice. The CR-IGR-002P, a colorectal PDX cell line was amplified in fifteen healthy female CB17 SCID (CB17/lcr-Prkdcscid/lcrlcoCrl) mice, 6-weeks old at reception (obtained from Charles River), by implantation subcutaneously into the right flank of each animal. When tumor volumes reached 500-1500 $mm^3$, tumors were surgically excised for the engraftment.

CB17 SCID mice (female) of 6-7 weeks old (obtained from Charles River) received a subcutaneous injection in the right flank region with tumor fragments amplified as described above. When tumors reached an average size of 100-200 $mm^3$, randomization was performed into 5 groups of 6 mice and treatment began. Homogeneity between groups was tested by an analysis of variance (ANOVA).

The test article administration was performed via intravenous injection through tail vein, and the dosing volume was 10 mL/kg. Treatment was initiated on the same day of randomization. Dosing was conducted in a Laminar Flow Cabinet.

After tumor cells inoculation, the animals were checked daily for morbidity and mortality. At the time of routine monitoring, the animals are checked for any adverse effects of tumor growth and treatments on normal behavior such as mobility, visual estimation of food and water consumption, body weight gain/loss, eye/hair matting and any other abnormal effects and are recorded in the Vivo Manager database (Biosystemes, France). Tumor volumes are measured every 3-4 days in two dimensions using an caliper, and the volume data are expressed in $mm^3$ using the formula: V=(L×W×W)/2, where V is tumor volume, L is tumor length (the longest tumor dimension) and W is tumor width (the longest tumor dimension perpendicular to L). Dosing as well as tumor and body weight measurements will be conducted in a Laminar Flow Cabinet. The endpoint of the experiment is a tumor volume of 2,000 $mm^3$, body weight loss over 20% or 29 days, whichever comes first.

TABLE 6

Overview of test items and dose levels included in in vivo study

| Test item | Dose levels (mg/kg) | Group (N = 8) | Administration | Dosing Schedule |
|---|---|---|---|---|
| vehicle | — | 1 | IV | Single dose |
| tusamitamab-DM4 | 5 | 2 | IV | Single dose |
| labetuzumab-3 | 10 | 3 | IV | Single dose |
| tusamitamab-3 | 10 | 4 | IV | Single dose |
| B12-3 | 10 | 5 | IV | Single dose |

Figure 12A:
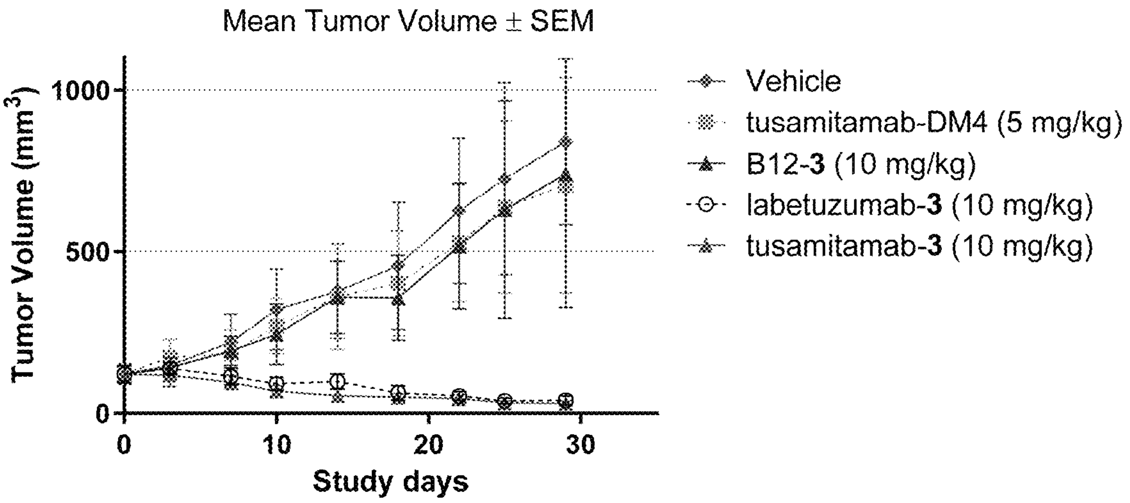
FIG. 12*a* shows the in vivo efficacy data of the colorectal IGR-002P PDX model. Tumor regression is observed for both labetuzumab-3 and tusamitamab-3 at 10 mg/kg. No effect was observed for tusamitamab-DM4, nor for B12-3 the negative control in this model.
Figure 12B:
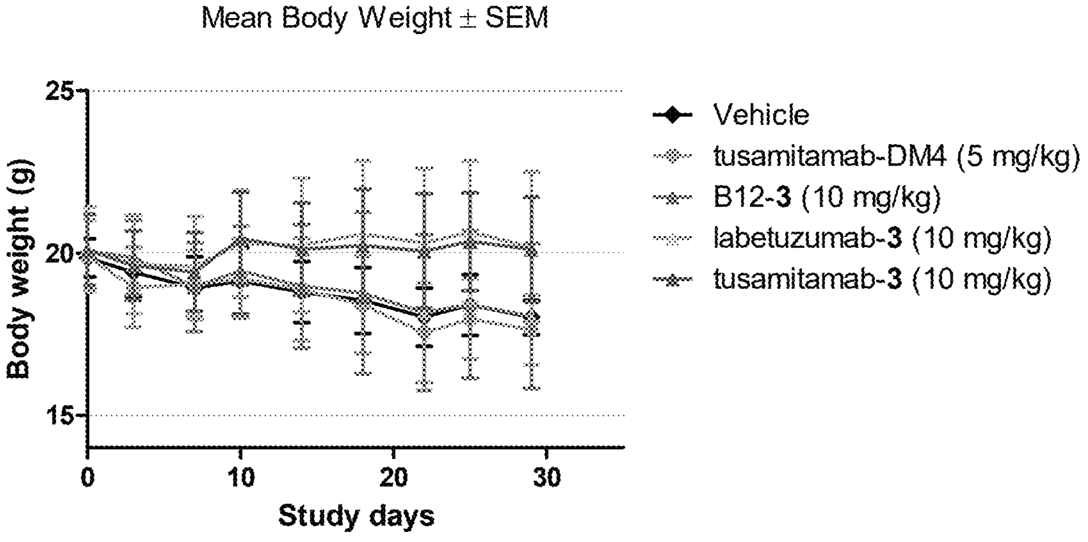
FIG. 12*b* shows body weight loss for the three groups in which no tumor growth inhibition was observed. This is due to the cachectic nature of the PDX model. Body weight was very constant for the groups that responded well to the treatment.

Data for efficacy study with the test items above is depicted in FIGS. 12A and 12B.

Example 22: In Vivo Efficacy Study of Several PDX Models, a Single Mouse Trial

Fragments of the patient-derived tumors, frozen in DMSO/SVF/RPMI 1640 medium (5/10/85) and stored in liquid nitrogen, were thawed at 37° C. for 5 min. Then they were rinsed twice in RPMI 1640 medium before subcutaneous implantation in immunodeficient mice and then serially transplanted in immunodeficient mice. The PDX cell lines, see table below, were amplified in 12 healthy female CB17 SCID (CB17/lcr-Prkdcscid/lcrlcoCrl) mice, 6-weeks old at reception (obtained from Charles River) and 9 healthy NSG (NOD.Cg.PrkdcSCID Il2rgtmWijl/SzJ, obtained from Charles River), by implantation subcutaneously into the right flank of each animal. When tumor volumes reached 500-1500 $mm^3$, tumors were surgically excised for the engraftment.

CB17 SCID mice (female) of 6-7 weeks old (obtained from Charles River) received a subcutaneous injection in the right flank region with tumor fragments amplified as described above. When tumors reached an average size of 100-200 $mm^3$, randomization was performed and treatment began. Homogeneity between groups was tested by an analysis of variance (ANOVA).

The test article administration was performed via intravenous injection through tail vein, and the dosing volume was 10 mL/kg. Dose was either vehicle or 10 mg/kg labetuzumab-3. Treatment was initiated on the same day of randomization. Dosing was conducted in a Laminar Flow Cabinet.

After tumor cells inoculation, the animals were checked daily for morbidity and mortality. At the time of routine monitoring, the animals are checked for any adverse effects of tumor growth and treatments on normal behavior such as mobility, visual estimation of food and water consumption, body weight gain/loss, eye/hair matting and any other abnormal effects and are recorded in the Vivo Manager database (Biosystemes, France). Tumor volumes are measured every 3-4 days in two dimensions using an caliper, and the volume data are expressed in $mm^3$ using the formula: V=(L×W×W)/2, where V is tumor volume, L is tumor length (the longest tumor dimension) and W is tumor width (the longest tumor dimension perpendicular to L). Dosing as well as tumor and body weight measurements will be conducted in a Laminar Flow Cabinet. The endpoint of the experiment is a tumor volume of 2,000 $mm^3$, body weight loss over 20% or 1.5 times survival over the vehicle, whichever comes first.

Tumor growth inhibition is calculated with the following equation:

$$\frac{T}{C}\% = 100 \times \frac{\text{Median tumor volume of treated group at Dx}}{\text{Median tumor volume of vehicle treated group at Dx}}$$

Where DX: Day of tumor volume measurement. The optimal value is the minimal T/C % ratio reflecting the maximal tumor growth inhibition achieved. Tumor growth inhibition is classified as follows:

<20%: high inhibition 21-40%: moderately high inhibition 41-80%: moderate inhibition >81%: low inhibition

TABLE 7

| []Overview and characteristics of the PDX models | | | | | |
|---|---|---|---|---|---|
| PDX model | Animals for amplification | Indication | CEACAM expression level (H-score) | Intensity of staining (IHC) | Irinotecan sensitive* |
| CR-IC-003P | SCID mice | Colorectal | ND | 2+ | no |
| CR-LRB-010P | SCID mice | Colorectal | ND | 1+ | yes |
| LUN-NIC-014 | SCID mice | Lung | 120 | 2+ | unknown |
| IM-PAN-007 | NSG mice | Pancreatic | 270 | 3+ | yes |
| SA-PAN-083 | NSG mice | Pancreatic | 70 | 1+ | yes |

*Yes means >40% irinotecan response

Figure 13A:
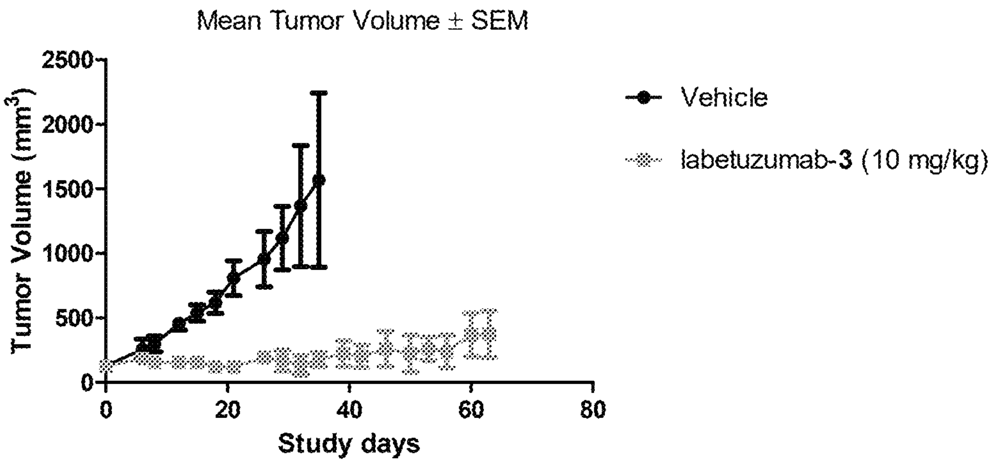
FIGS. 13(A)-(O) show the in vivo efficacy data obtained with labetuzumab-3 for several PDX models.
Figure 13B:
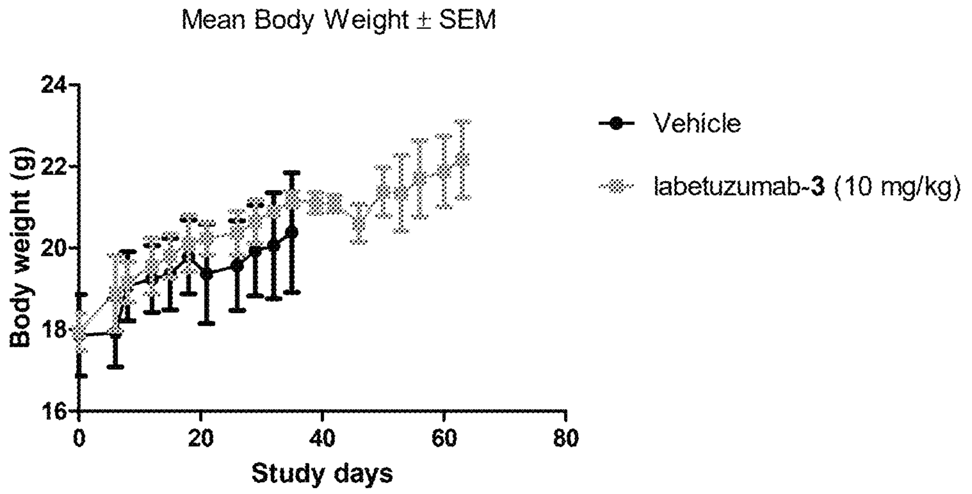
Figure 13C:
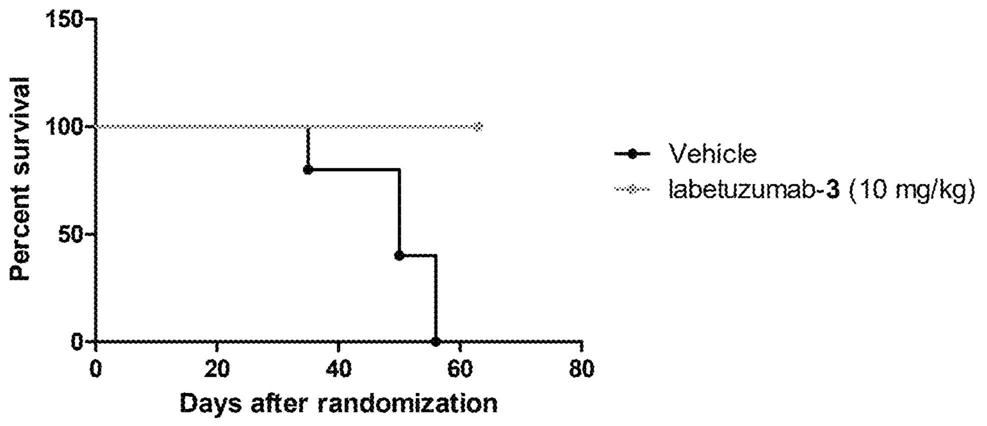
Figure 13D:
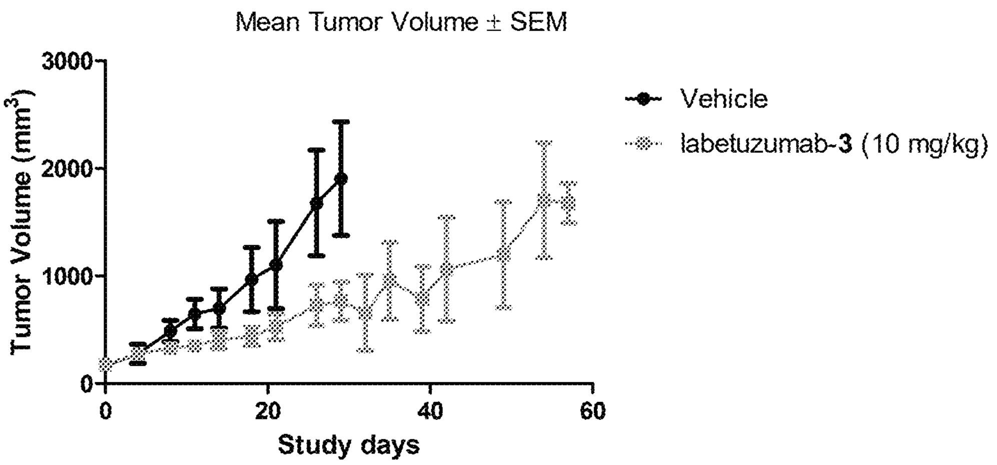
FIGS. 13(D)-(F) show the plots corresponding to colorectal LRB-010P PDX model. Tumor growth inhibition was observed in the treated group, with a greatly enhanced overall survival (at least 1.5× compared to vehicle).
Figure 13E:
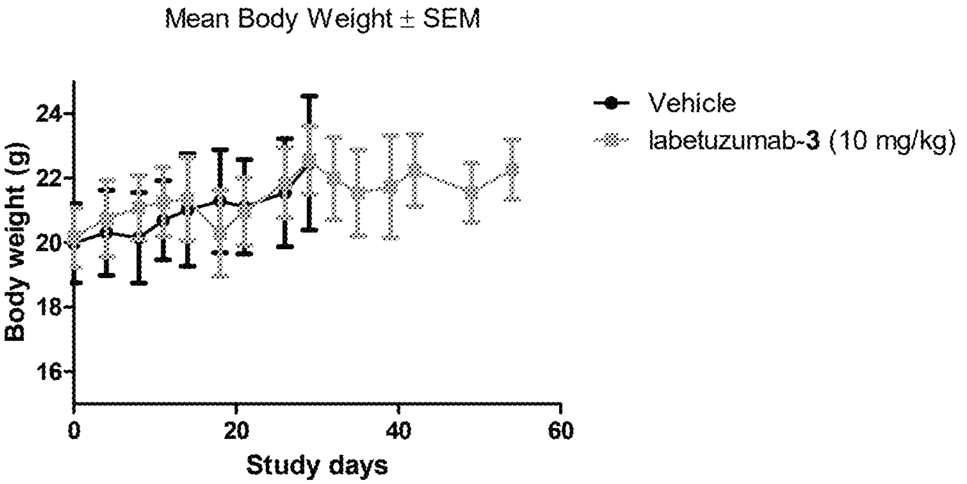
Figure 13F:
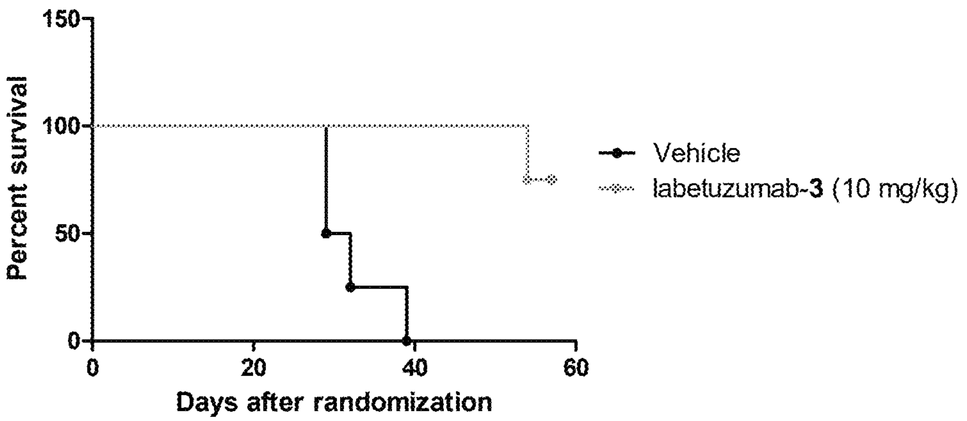
Figure 13G:
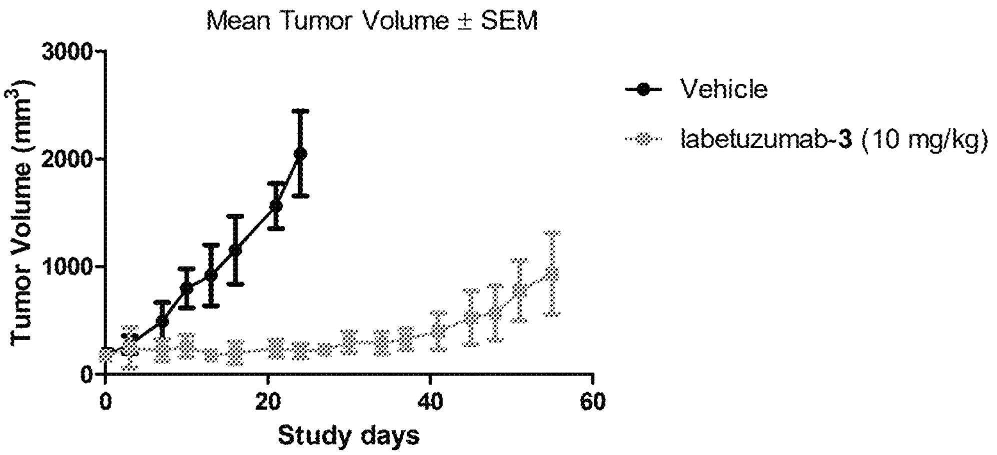
FIGS. 13(G)-(I) show the plots corresponding to lung NIC-014 PDX model. Tumor regression is observed for this fast growing model with at least a twofold increased overall survival.
Figure 13H:
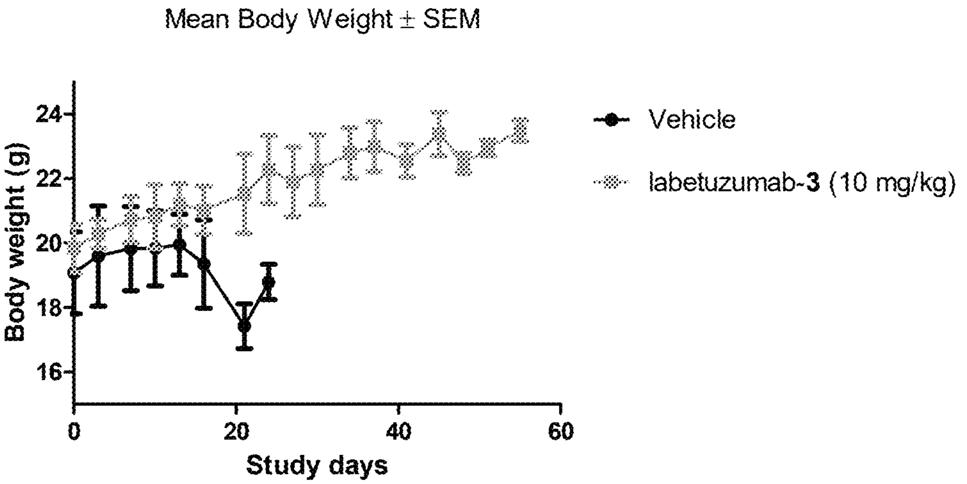
Figure 13I:
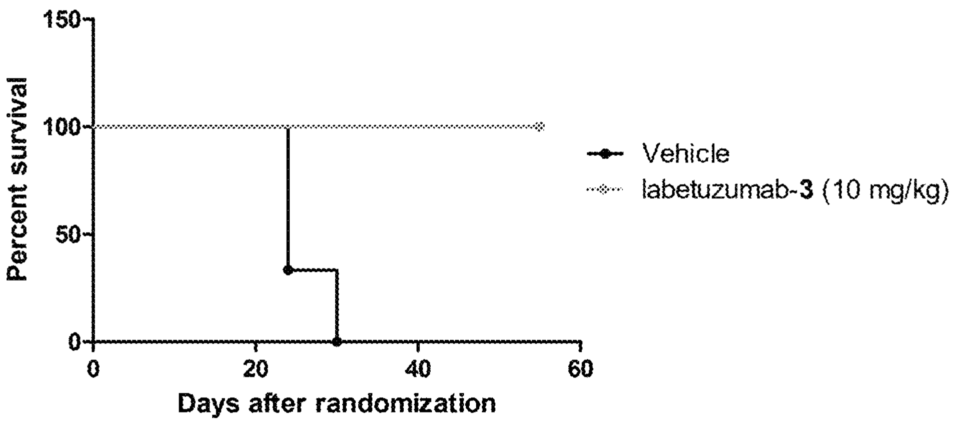
Figure 13J:
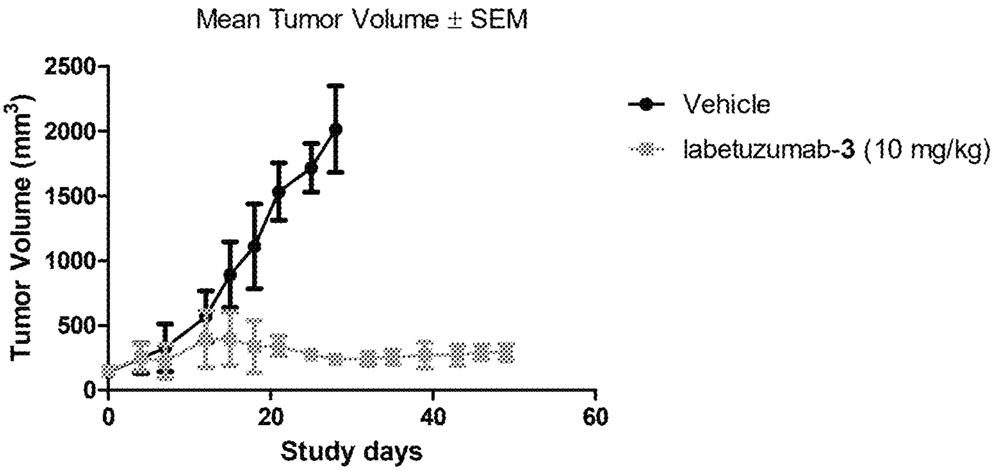
FIGS. 13(J)-(L) show the plots corresponding to pancreatic SA-083 PDX model. Tumor growth inhibition is also observed for this indication. Tumor growth inhibition is confirmed in another pancreatic PDX model.
Figure 13K:
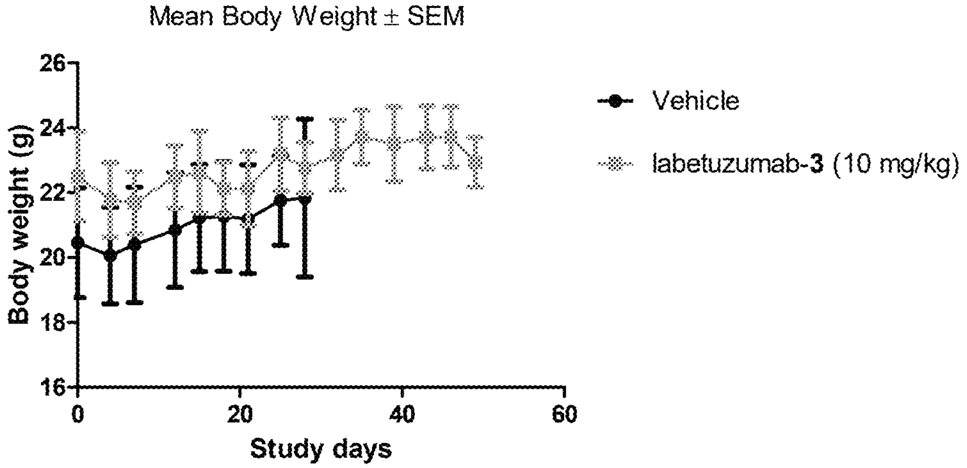
Figure 13L:
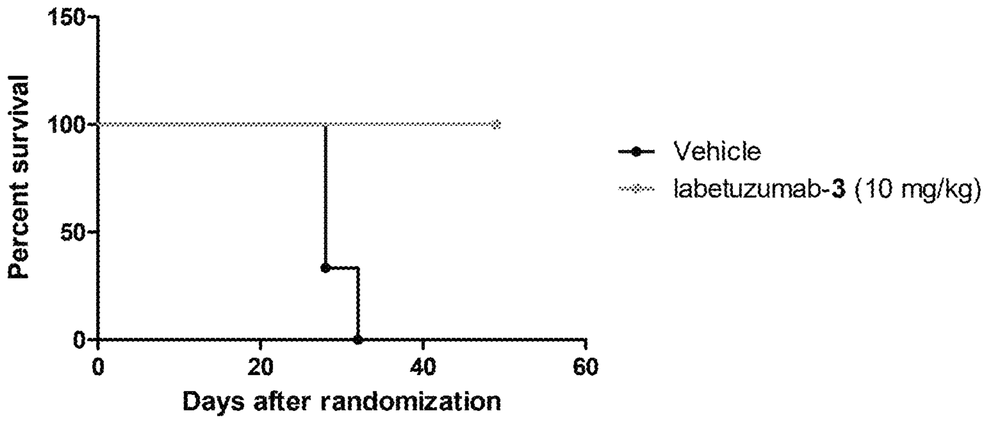
Figure 13M:
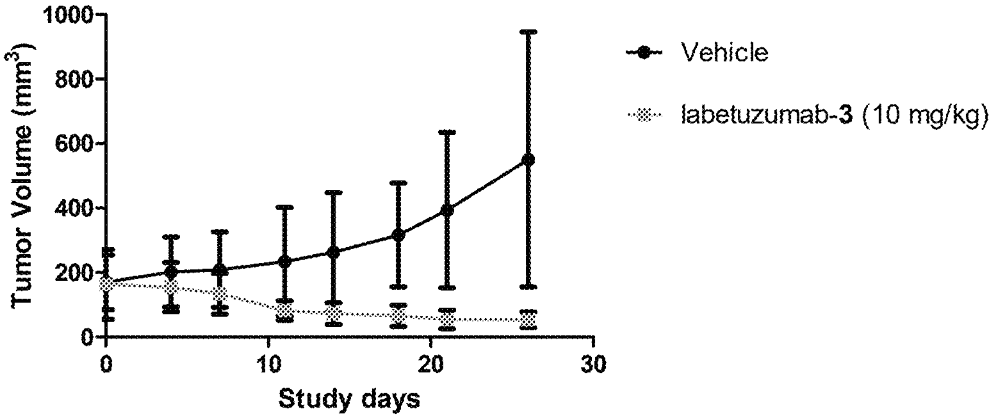
Figure 13N:
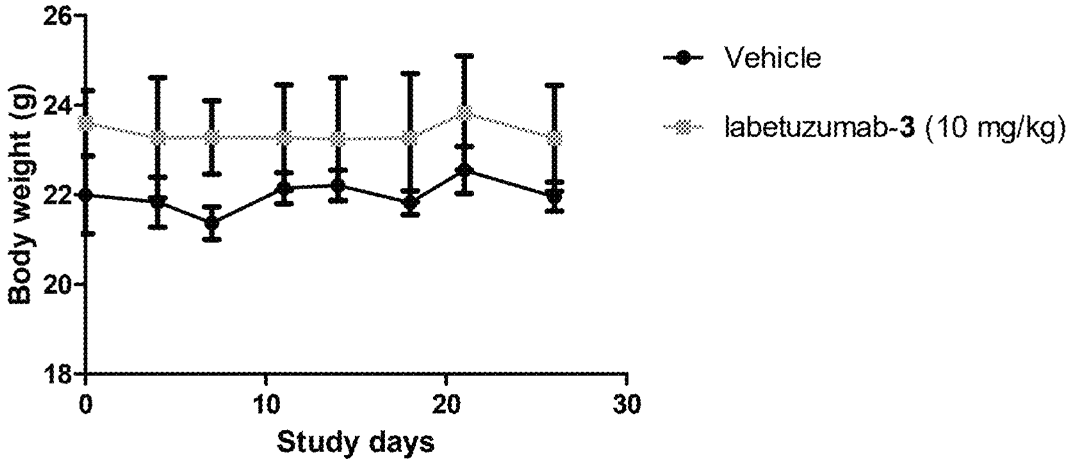
Figure 13O:
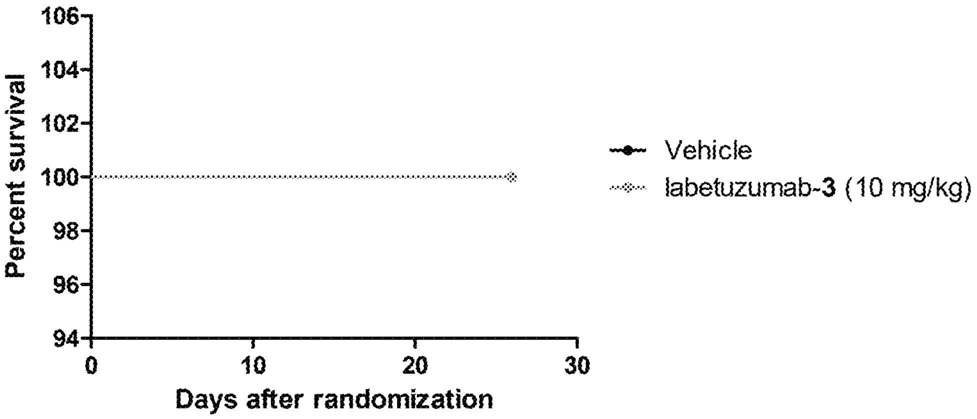

FIGS. 13A-13O show the efficacy plots, body weight plots and Kaplan-Meier plots per PDX model. Table 8 below shows the TGI % per model.

TABLE 8

| TGI % per model | | |
|---|---|---|
| PDX model | TGI % | Classification |
| CR-IC-003P | 8.3% | High inhibition |
| CR-LRB-010P | 29.4% | Moderately high inhibition |
| LUN-NIC-014 | 11.9% | High inhibition |
| IM-PAN-007 | 11.8% | High inhibition |
| SA-PAN-083 | 11.2% | High inhibition |

Example 23: In Vivo Tolerability Study

Sprague Dawley rats (female) of 6-7 weeks old acclimatized for a week before being enrolled in the study.

Randomization: In the tolerability study totally 15 rats were enrolled and randomly allocated to 5 study groups with 3 rats per group. Randomization was performed based on "Matched distribution" method (StudyDirector™ software, version 3.1.399.19). The date of randomization was denoted as day 0.

Test Article Administration: The treatment was initiated on the same day of randomization (day 0) per study design. Chosen dose levels were 80, 100, 120 and 140 mg/kg, single dose. All animals were dosed via slow intravenous injection (10 mL/kg).

Observation and Data Collection After randomization: The animals were checked daily for morbidity and mortality. During routine monitoring, the animals were checked for any effects of treatments on behavior such as mobility, food and water consumption, body weight gain/loss, eye/hair matting and any other abnormalities. Mortality and observed clinical signs were recorded for individual animals in detail. Dosing as well as body weight measurements were conducted in a Laminar Flow Cabinet. The body weights were measured daily by using StudyDirector™ software (version 3.1.399.19).

Figure 14:
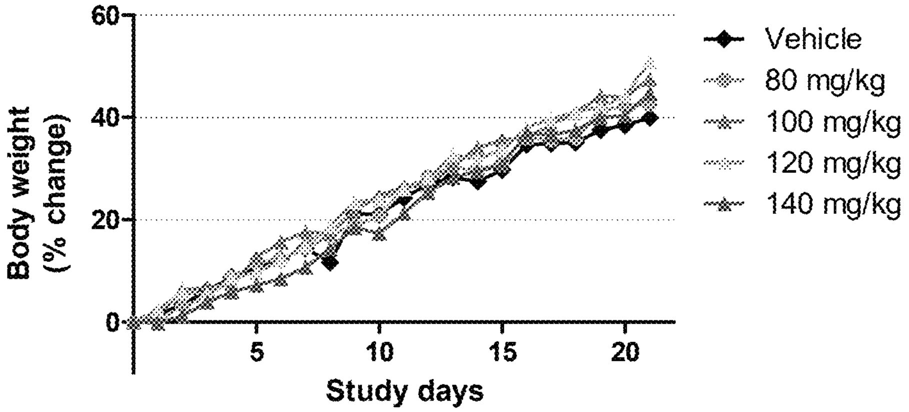
FIG. 14 shows the in vivo tolerability data obtained with labetuzumab-3. The body weight change (%) over time is depicted, which was more or less equal for all doses tested. Even up to a dose of 140 mg/kg, no toxicity was observed. Hence the MTD is above 140 mg/kg.

Body weight of the rats over time with labetuzumab-3 as test item at several dose levels are depicted in FIG. 14.

SEQUENCE LISTING

```
Sequence total quantity: 54
SEQ ID NO: 1            moltype = AA  length = 123
FEATURE                 Location/Qualifiers
REGION                  1..123
                        note = CEA6 VH
source                  1..123
                        mol_type = protein
                        organism = synthetic construct
SEQUENCE: 1
EVQLVESGGG VVRPGGSLRL SCAASGFTFD DYGMSWVRQA PGKGLEWVSS IIPSFGTANY  60
AQKFQGRLTI TADESTSTAY MELSSLRSED TAVYYCAGRS HNYELYYYYM DVWGQGTMVT  120
VSS                                                               123

SEQ ID NO: 2            moltype = AA  length = 108
FEATURE                 Location/Qualifiers
REGION                  1..108
                        note = CEA6 VL
source                  1..108
                        mol_type = protein
                        organism = synthetic construct
SEQUENCE: 2
DIQMTQSPSS LSASIGDRVT ITCRADEGIY HWLAWYQQKP GKAPKLLIYK ASSLASGAPS  60
RFSGSGSGTD FTLTISSLQP DDFATYYCQQ YSNYPLTFGG GTKLEIKR              108

SEQ ID NO: 3            moltype = AA  length = 121
FEATURE                 Location/Qualifiers
REGION                  1..121
                        note = M5A VH1
source                  1..121
                        mol_type = protein
                        organism = synthetic construct
SEQUENCE: 3
```

-continued

```
EVQLVESGGG LVQPGGSLRL SCAASGFNIK DTYMHWVRQA PGKGLEWVAR IDPANGNSKY  60
ADSVKGRFTI SADTSKNTAY LQMNSLRAED TAVYYCAPFG YYVSDYAMAY WGQGTLVTVS  120
S                                                                  121

SEQ ID NO: 4           moltype = AA  length = 451
FEATURE                Location/Qualifiers
REGION                 1..451
                       note = M5A HC
source                 1..451
                       mol_type = protein
                       organism = synthetic construct
SEQUENCE: 4
EVQLVESGGG LVQPGGSLRL SCAASGFNIK DTYMHWVRQA PGKGLEWVAR IDPANGNSKY  60
ADSVKGRFTI SADTSKNTAY LQMNSLRAED TAVYYCAPFG YYVSDYAMAY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKRVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRE  360
EMTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                 451

SEQ ID NO: 5           moltype = AA  length = 121
FEATURE                Location/Qualifiers
REGION                 1..121
                       note = M5B VH2
source                 1..121
                       mol_type = protein
                       organism = synthetic construct
SEQUENCE: 5
EVQLVESGGG LVQPGGSLRL SCAASGFNIK DTYMHWVRQA PGKGLEWVAR IDPANGNSKY  60
VPKFQGRATI SADTSKNTAY LQMDSLRAED TAVYYCAPFG YYVSDYAMAY WGQGTLVTVS  120
S                                                                  121

SEQ ID NO: 6           moltype = AA  length = 111
FEATURE                Location/Qualifiers
REGION                 1..111
                       note = M5B VL
source                 1..111
                       mol_type = protein
                       organism = synthetic construct
SEQUENCE: 6
DIQLTQSPSS LSASVGDRVT ITCRAGESVD IFGVGFLHWY QQKPGKAPKL LIYRASNLES  60
GVPSRFSGSG SRTDFTLTIS SLQPEDFATY YCQQTNEDPY TFGQGTKVEI K           111

SEQ ID NO: 7           moltype = AA  length = 451
FEATURE                Location/Qualifiers
REGION                 1..451
                       note = M5B HC
source                 1..451
                       mol_type = protein
                       organism = synthetic construct
SEQUENCE: 7
EVQLVESGGG LVQPGGSLRL SCAASGFNIK DTYMHWVRQA PGKGLEWVAR IDPANGNSKY  60
VPKFQGRATI SADTSKNTAY LQMDSLRAED TAVYYCAPFG YYVSDYAMAY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKRVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRE  360
EMTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                 451

SEQ ID NO: 8           moltype = AA  length = 218
FEATURE                Location/Qualifiers
REGION                 1..218
                       note = M5B LC
source                 1..218
                       mol_type = protein
                       organism = synthetic construct
SEQUENCE: 8
DIQLTQSPSS LSASVGDRVT ITCRAGESVD IFGVGFLHWY QQKPGKAPKL LIYRASNLES  60
GVPSRFSGSG SRTDFTLTIS SLQPEDFATY YCQQTNEDPY TFGQGTKVEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 9           moltype = AA  length = 121
FEATURE                Location/Qualifiers
REGION                 1..121
                       note = A5B7 VH
source                 1..121
```

-continued

```
                        mol_type = protein
                        organism = synthetic construct
SEQUENCE: 9
EVQLVESGGG LVQPGRSLRL SCAASGFTVS SYWMHWVRQA PGKGLEWVGF IRNKANGGTT  60
EYAASVKGRF TISRDDSKNT LYLQMNSLRA EDTAVYYCAR DRGLRFYFDY WGQGTTVTVS  120
S                                                                  121

SEQ ID NO: 10           moltype = AA  length = 116
FEATURE                 Location/Qualifiers
REGION                  1..116
                        note = A5B7 VL
source                  1..116
                        mol_type = protein
                        organism = synthetic construct
SEQUENCE: 10
QAVLTQPASL SASPGASASL TCTLRRGINV GAYSIYWYQQ KPGSPPQYLL RYKSDSDKQQ  60
GSGVSSRFSA SKDASANAGI LLISGLQSED EADYYCMIWH SGASAVFGGG TKLTVL      116

SEQ ID NO: 11           moltype = AA  length = 119
FEATURE                 Location/Qualifiers
REGION                  1..119
                        note = A5/A240VL VH
source                  1..119
                        mol_type = protein
                        organism = synthetic construct
SEQUENCE: 11
EVQLVESGGG VVQPGRSLRL SCAASGFTLS TYAMHWVRQA PGKGLEWVAL ISNDGSNKYY  60
ADSVKGRFTI SRDNSKNTLY LQMNSLRAED TAVYYCARDR GLRFYFDYWG QGTTVTVSS   119

SEQ ID NO: 12           moltype = AA  length = 449
FEATURE                 Location/Qualifiers
REGION                  1..449
                        note = A5/A240VL HC
source                  1..449
                        mol_type = protein
                        organism = synthetic construct
SEQUENCE: 12
EVQLVESGGG VVQPGRSLRL SCAASGFTLS TYAMHWVRQA PGKGLEWVAL ISNDGSNKYY  60
ADSVKGRFTI SRDNSKNTLY LQMNSLRAED TAVYYCARDR GLRFYFDYWG QGTTVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                    449

SEQ ID NO: 13           moltype = AA  length = 119
FEATURE                 Location/Qualifiers
REGION                  1..119
                        note = D8/A240VL VH
source                  1..119
                        mol_type = protein
                        organism = synthetic construct
SEQUENCE: 13
QVQLVESGGG VVQPGRSLRL SCAASGFTLS TYAMHWVRQA PGKGLEWVAL ISNDGSNKYY  60
ADSVKGRFTI SRDNSKNTLY LQMNSLRAED TAVYYCTRDR GLRFYFDYWG QGTTVTVSS   119

SEQ ID NO: 14           moltype = AA  length = 449
FEATURE                 Location/Qualifiers
REGION                  1..449
                        note = D8/A240VL HC
source                  1..449
                        mol_type = protein
                        organism = synthetic construct
SEQUENCE: 14
QVQLVESGGG VVQPGRSLRL SCAASGFTLS TYAMHWVRQA PGKGLEWVAL ISNDGSNKYY  60
ADSVKGRFTI SRDNSKNTLY LQMNSLRAED TAVYYCTRDR GLRFYFDYWG QGTTVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                    449

SEQ ID NO: 15           moltype = AA  length = 223
FEATURE                 Location/Qualifiers
REGION                  1..223
                        note = D8/A240VL LC
source                  1..223
```

-continued

```
                        mol_type = protein
                        organism = synthetic construct
SEQUENCE: 15
QAVLTQPASL SASPGASASL TCTLRRGINV GAYSIYWYQQ KPGSPPQYLL RYKSDSDKQQ  60
GSGVSSRFSA SKDASANAGI LLISGLQSED EADYYCMIWH SGASAVFGGG TKLTVLRTVA  120
APSVFIFPPS DEQLKSGTAS VVCLLNNFYP REAKVQWKVD NALQSGNSQE SVTEQDSKDS  180
TYSLSSTLTL SKADYEKHKV YACEVTHQGL SSPVTKSFNR GEC                   223

SEQ ID NO: 16           moltype = AA  length = 120
FEATURE                 Location/Qualifiers
REGION                  1..120
                        note = SM3E VH
source                  1..120
                        mol_type = protein
                        organism = synthetic construct
SEQUENCE: 16
QVKLEQSGAG VVKPGASVKL SCKASGFNIK DSYMHWLRQG PGQRLEWIGW IDPENGDTEY  60
APKFQGKATF TTDTSANTAY LGLSSLRPED TAVYYCNEGT PTGPYYFDYW GQGTLVTVSS  120

SEQ ID NO: 17           moltype = AA  length = 108
FEATURE                 Location/Qualifiers
REGION                  1..108
                        note = SM3E VL
source                  1..108
                        mol_type = protein
                        organism = synthetic construct
SEQUENCE: 17
QNVLTQSPSS MSVSVGDRVT IACSASSSVP YMHWLQQKPG KSPKLLIYLT SNLASGVPSR  60
FSGSGSGTDY SLTISSVQPE DAATYYCQQR SSYPLTFGGG TKLEIKAA              108

SEQ ID NO: 18           moltype = AA  length = 450
FEATURE                 Location/Qualifiers
REGION                  1..450
                        note = SM3E HC
source                  1..450
                        mol_type = protein
                        organism = synthetic construct
SEQUENCE: 18
QVKLEQSGAG VVKPGASVKL SCKASGFNIK DSYMHWLRQG PGQRLEWIGW IDPENGDTEY  60
APKFQGKATF TTDTSANTAY LGLSSLRPED TAVYYCNEGT PTGPYYFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKRVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                  450

SEQ ID NO: 19           moltype = AA  length = 213
FEATURE                 Location/Qualifiers
REGION                  1..213
                        note = SM3E LC
source                  1..213
                        mol_type = protein
                        organism = synthetic construct
SEQUENCE: 19
QNVLTQSPSS MSVSVGDRVT IACSASSSVP YMHWLQQKPG KSPKLLIYLT SNLASGVPSR  60
FSGSGSGTDY SLTISSVQPE DAATYYCQQR SSYPLTFGGG TKLEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                              213

SEQ ID NO: 20           moltype = AA  length = 121
FEATURE                 Location/Qualifiers
REGION                  1..121
                        note = hRP1A3 VH
source                  1..121
                        mol_type = protein
                        organism = synthetic construct
SEQUENCE: 20
QVQLVQSGSE LKKPGASVKV SCKASGYTFT VFGMNWVRQA PGQGLEWMGW INTKTGEATY  60
VEEFKGRFVF SLDTSVSTAY LQISSLKADD TAVYYCARWD FAYYVEAMDY WGQGTTVTVS  120
S                                                                 121

SEQ ID NO: 21           moltype = AA  length = 109
FEATURE                 Location/Qualifiers
REGION                  1..109
                        note = hRP1A3 VL
source                  1..109
                        mol_type = protein
                        organism = synthetic construct
```

```
SEQUENCE: 21
DIQMTQSPSS LSASVGDRVT ITCKASQNVG TNVAWYQQKP GKAPKLLIYS ASYRYSGVPS  60
RFSGSGSGTD FTFTISSLQP EDIATYYCHQ YYTYPLFTFG QGTKVEIKR              109

SEQ ID NO: 22          moltype = AA  length = 451
FEATURE                Location/Qualifiers
REGION                 1..451
                       note = hRP1A3 HC
source                 1..451
                       mol_type = protein
                       organism = synthetic construct
SEQUENCE: 22
QVQLVQSGSE LKKPGASVKV SCKASGYTFT VFGMNWVRQA PGQGLEWMGW INTKTGEATY  60
VEEFKGRFVF SLDTSVSTAY LQISSLKADD TAVYYCARWD FAYYVEAMDY WGQGTTVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKRVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRE  360
EMTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                 451

SEQ ID NO: 23          moltype = AA  length = 215
FEATURE                Location/Qualifiers
REGION                 1..215
                       note = hRP1A3 LC
source                 1..215
                       mol_type = protein
                       organism = synthetic construct
SEQUENCE: 23
DIQMTQSPSS LSASVGDRVT ITCKASQNVG TNVAWYQQKP GKAPKLLIYS ASYRYSGVPS  60
RFSGSGSGTD FTFTISSLQP EDIATYYCHQ YYTYPLFTFG QGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 24          moltype = AA  length = 121
FEATURE                Location/Qualifiers
REGION                 1..121
                       note = CH1A1A/CH7A VH
source                 1..121
                       mol_type = protein
                       organism = synthetic construct
SEQUENCE: 24
QVQLVQSGAE VKKPGASVKV SCKASGYTFT EFGMNWVRQA PGQGLEWMGW INTKTGEATY  60
VEEFKGRVTF TTDTSTSTAY MELRSLRSDD TAVYYCARWD FYDYVEAMDY WGQGTTVTVS  120
S                                                                  121

SEQ ID NO: 25          moltype = AA  length = 451
FEATURE                Location/Qualifiers
REGION                 1..451
                       note = CH1A1A/CH7A HC
source                 1..451
                       mol_type = protein
                       organism = synthetic construct
SEQUENCE: 25
QVQLVQSGAE VKKPGASVKV SCKASGYTFT EFGMNWVRQA PGQGLEWMGW INTKTGEATY  60
VEEFKGRVTF TTDTSTSTAY MELRSLRSDD TAVYYCARWD FYDYVEAMDY WGQGTTVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKRVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRE  360
EMTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                 451

SEQ ID NO: 26          moltype = AA  length = 121
FEATURE                Location/Qualifiers
REGION                 1..121
                       note = CH1A1B VH
source                 1..121
                       mol_type = protein
                       organism = synthetic construct
SEQUENCE: 26
QVKLQQSGAE VKKPGASVKV SCKASGYTFT EFGMNWVRQA PGQGLEWMGW INTKTGEATY  60
VEEFKGRVTM TTDTSTSTAY MELRSLRSDD TAVYYCARWD FYDYVEAMDY WGQGTTVTVS  120
S                                                                  121

SEQ ID NO: 27          moltype = AA  length = 451
FEATURE                Location/Qualifiers
REGION                 1..451
                       note = CH1A1B HC
```

```
source                  1..451
                        mol_type = protein
                        organism = synthetic construct
SEQUENCE: 27
QVKLQQSGAE VKKPGASVKV SCKASGYTFT EFGMNWVRQA PGQGLEWMGW INTKTGEATY  60
VEEFKGRVTM TTDTSTSTAY MELRSLRSDD TAVYYCARWD FYDYVEAMDY WGQGTTVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKRVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRE  360
EMTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                 451

SEQ ID NO: 28           moltype = AA  length = 110
FEATURE                 Location/Qualifiers
REGION                  1..110
                        note = pAC18/2F1 VL
source                  1..110
                        mol_type = protein
                        organism = synthetic construct
SEQUENCE: 28
DIQMTGSPSS LSASVGDRVT ITCKASAAVG TYVAWYQQKP GKAPKLLIYS ASYRKRGVPS  60
RFSGSGSGTD FTLTISSLQP EDFATYYCHQ YYTYPLFTFG YGTKLEIKRT             110

SEQ ID NO: 29           moltype = AA  length = 215
FEATURE                 Location/Qualifiers
REGION                  1..215
                        note = pAC18/2F1 LC
source                  1..215
                        mol_type = protein
                        organism = synthetic construct
SEQUENCE: 29
DIQMTGSPSS LSASVGDRVT ITCKASAAVG TYVAWYQQKP GKAPKLLIYS ASYRKRGVPS  60
RFSGSGSGTD FTLTISSLQP EDFATYYCHQ YYTYPLFTFG YGTKLEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 30           moltype = AA  length = 121
FEATURE                 Location/Qualifiers
REGION                  1..121
                        note = anti-CEA VH
source                  1..121
                        mol_type = protein
                        organism = synthetic construct
SEQUENCE: 30
QVQLVQSGSE LKKPGASVKV SCKASGYTFT EYGMNWVRQA PGQGLEWMGW INTKSGEATY  60
VEEFKGRFVF SLDTSVSTAY LQISSLKAED TAVYYCARWD FYDYVEAMDY WGQGTTVTVS  120
S                                                                 121

SEQ ID NO: 31           moltype = AA  length = 110
FEATURE                 Location/Qualifiers
REGION                  1..110
                        note = anti-CEA VL
source                  1..110
                        mol_type = protein
                        organism = synthetic construct
SEQUENCE: 31
DIQMTQSPSS LSASVGDRVT ITCKASQTVS ANVAWYQQKP GKAPKLLIYL ASYRYRGVPS  60
RFSGSGSGTD FTLTISSLQP EDFATYYCHQ YYTYPLFTFG QGTKLEIKRT             110

SEQ ID NO: 32           moltype = AA  length = 451
FEATURE                 Location/Qualifiers
REGION                  1..451
                        note = anti-CEA HC
source                  1..451
                        mol_type = protein
                        organism = synthetic construct
SEQUENCE: 32
QVQLVQSGSE LKKPGASVKV SCKASGYTFT EYGMNWVRQA PGQGLEWMGW INTKSGEATY  60
VEEFKGRFVF SLDTSVSTAY LQISSLKAED TAVYYCARWD FYDYVEAMDY WGQGTTVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKRVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRE  360
EMTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                 451

SEQ ID NO: 33           moltype = AA  length = 215
FEATURE                 Location/Qualifiers
```

-continued

```
REGION                  1..215
                        note = anti-CEA LC
source                  1..215
                        mol_type = protein
                        organism = synthetic construct
SEQUENCE: 33
DIQMTQSPSS LSASVGDRVT ITCKASQTVS ANVAWYQQKP GKAPKLLIYL ASYRYRGVPS  60
RFSGSGSGTD FTLTISSLQP EDFATYYCHQ YYTYPLFTFG QGTKLEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                           215

SEQ ID NO: 34           moltype = AA  length = 119
FEATURE                 Location/Qualifiers
REGION                  1..119
                        note = labetuzumab VH
source                  1..119
                        mol_type = protein
                        organism = synthetic construct
SEQUENCE: 34
EVQLVESGGG VVQPGRSLRL SCSASGFDFT TYWMSWVRQA PGKGLEWIGE IHPDSSTINY  60
APSLKDRFTI SRDNAKNTLF LQMDSLRPED TGVYFCASLY FGFPWFAYWG QGTPVTVSS   119

SEQ ID NO: 35           moltype = AA  length = 106
FEATURE                 Location/Qualifiers
REGION                  1..106
                        note = labetuzumab VL
source                  1..106
                        mol_type = protein
                        organism = synthetic construct
SEQUENCE: 35
DIQLTQSPSS LSASVGDRVT ITCKASQDVG TSVAWYQQKP GKAPKLLIYW TSTRHTGVPS  60
RFSGSGSGTD FTFTISSLQP EDIATYYCQQ YSLYRSFGQG TKVEIK               106

SEQ ID NO: 36           moltype = AA  length = 449
FEATURE                 Location/Qualifiers
REGION                  1..449
                        note = labetuzumab HC
source                  1..449
                        mol_type = protein
                        organism = synthetic construct
SEQUENCE: 36
EVQLVESGGG VVQPGRSLRL SCSASGFDFT TYWMSWVRQA PGKGLEWIGE IHPDSSTINY  60
APSLKDRFTI SRDNAKNTLF LQMDSLRPED TGVYFCASLY FGFPWFAYWG QGTPVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                  449

SEQ ID NO: 37           moltype = AA  length = 449
FEATURE                 Location/Qualifiers
REGION                  1..449
                        note = labetuzumab HC*
source                  1..449
                        mol_type = protein
                        organism = synthetic construct
SEQUENCE: 37
EVQLVESGGG VVQPGRSLRL SCSASGFDFT TYWMSWVRQA PGKGLEWIGE IHPDSSTINY  60
APSLKDRFTI SRDNAKNTLF LQMDSLRPED TGVYFCASLY FGFPWFAYWG QGTPVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCDKTHTCPP CPAPELLGGP  240
SVFLFPPKPK DTLYITREPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                  449

SEQ ID NO: 38           moltype = AA  length = 213
FEATURE                 Location/Qualifiers
REGION                  1..213
                        note = labetuzumab LC
source                  1..213
                        mol_type = protein
                        organism = synthetic construct
SEQUENCE: 38
DIQLTQSPSS LSASVGDRVT ITCKASQDVG TSVAWYQQKP GKAPKLLIYW TSTRHTGVPS  60
RFSGSGSGTD FTFTISSLQP EDIATYYCQQ YSLYRSFGQG TKVEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                             213
```

```
SEQ ID NO: 39          moltype = AA  length = 120
FEATURE                Location/Qualifiers
REGION                 1..120
                       note = tusamitamab VH
source                 1..120
                       mol_type = protein
                       organism = synthetic construct
SEQUENCE: 39
EVQLQESGPG LVKPGGSLSL SCAASGFVFS SYDMSWVRQT PERGLEWVAY ISSGGGITYA  60
PSTVKGRFTV SRDNAKNTLY LQMNSLTSED TAVYYCAAHY FGSSGPFAYW GQGTLVTVSS  120

SEQ ID NO: 40          moltype = AA  length = 106
FEATURE                Location/Qualifiers
REGION                 1..106
                       note = tusamitamab VL
source                 1..106
                       mol_type = protein
                       organism = synthetic construct
SEQUENCE: 40
DIQMTQSPAS LSASVDRVTI TCRASENIFS YLAWYQQKPG KSPKLLVYNT RTLAEGVPSR  60
FSGSGSGTDF SLTISSLQPE DFATYYCQHH YGTPFTFGSG TKLEIK                106

SEQ ID NO: 41          moltype = AA  length = 449
FEATURE                Location/Qualifiers
REGION                 1..449
                       note = tusamitamab HC
source                 1..449
                       mol_type = protein
                       organism = synthetic construct
SEQUENCE: 41
EVQLQESGPG LVKPGGSLSL SCAASGFVFS SYDMSWVRQT PERGLEWVAY ISSGGGITYA  60
PSTVKGRFTV SRDNAKNTLY LQMNSLTSED TAVYYCAAHY FGSSGPFAYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPG                                   449

SEQ ID NO: 42          moltype = AA  length = 449
FEATURE                Location/Qualifiers
REGION                 1..449
                       note = tusamitamab HC*
source                 1..449
                       mol_type = protein
                       organism = synthetic construct
SEQUENCE: 42
EVQLQESGPG LVKPGGSLSL SCAASGFVFS SYDMSWVRQT PERGLEWVAY ISSGGGITYA  60
PSTVKGRFTV SRDNAKNTLY LQMNSLTSED TAVYYCAAHY FGSSGPFAYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLYITREP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPG                                   449

SEQ ID NO: 43          moltype = AA  length = 213
FEATURE                Location/Qualifiers
REGION                 1..213
                       note = tusamitamab LC
source                 1..213
                       mol_type = protein
                       organism = synthetic construct
SEQUENCE: 43
DIQMTQSPAS LSASVDRVTI TCRASENIFS YLAWYQQKPG KSPKLLVYNT RTLAEGVPSR  60
FSGSGSGTDF SLTISSLQPE DFATYYCQHH YGTPFTFGSG TKLEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                              213

SEQ ID NO: 44          moltype = AA  length = 120
FEATURE                Location/Qualifiers
REGION                 1..120
                       note = huMAb2-4 VH
source                 1..120
                       mol_type = protein
                       organism = synthetic construct
SEQUENCE: 44
EVQLQESGPG LVKPGGSLSL SCAASGFVFS SYDMSWVRQT PERRLEWVAY ISSGGGITYF  60
```

-continued

```
PSTVKGRFTV SRDNAKNTLY LQMNSLTSED TAIYYCAAHY FGSSGPFAYW GQGTLVTVSA  120

SEQ ID NO: 45          moltype = AA  length = 106
FEATURE                Location/Qualifiers
REGION                 1..106
                       note = huMAb2-4 VL
source                 1..106
                       mol_type = protein
                       organism = synthetic construct
SEQUENCE: 45
DIQMTQSPAS LSASVDTVTI TCRASENIFS YLAWYQQKPG KSPKLLVYNT RTLAEGVPSR  60
FSGSGSGTQF SLTISSLQPE DFGSYYCQHH YGTPFTFGSG TKLEIK                106

SEQ ID NO: 46          moltype = AA  length = 449
FEATURE                Location/Qualifiers
REGION                 1..449
                       note = huMAb2-4 HC
source                 1..449
                       mol_type = protein
                       organism = synthetic construct
SEQUENCE: 46
EVQLQESGPG LVKPGGSLSL SCAASGFVFS SYDMSWVRQT PERRLEWVAY ISSGGGITYF  60
PSTVKGRFTV SRDNAKNTLY LQMNSLTSED TAIYYCAAHY FGSSGPFAYW GQGTLVTVSA  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPG                                   449

SEQ ID NO: 47          moltype = AA  length = 213
FEATURE                Location/Qualifiers
REGION                 1..213
                       note = huMAb2-4 LC
source                 1..213
                       mol_type = protein
                       organism = synthetic construct
SEQUENCE: 47
DIQMTQSPAS LSASVDTVTI TCRASENIFS YLAWYQQKPG KSPKLLVYNT RTLAEGVPSR  60
FSGSGSGTQF SLTISSLQPE DFGSYYCQHH YGTPFTFGSG TKLEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                              213

SEQ ID NO: 48          moltype = AA  length = 125
FEATURE                Location/Qualifiers
REGION                 1..125
                       note = VH
source                 1..125
                       mol_type = protein
                       organism = synthetic construct
SEQUENCE: 48
EVQLVESGGG LVQPGGSLKL SCAASGFTFN TYAMNWVRQA PGKGLEWVGR IRSKYNNYAT  60
YYADSVKDRF TISRDDSKNT AYLQMNSLKT EDTAVYYCVR HGNFGNSYVS WFAYWGQGTL  120
VTVSS                                                             125

SEQ ID NO: 49          moltype = AA  length = 109
FEATURE                Location/Qualifiers
REGION                 1..109
                       note = AB17 VL
source                 1..109
                       mol_type = protein
                       organism = synthetic construct
SEQUENCE: 49
EIVLTQSPAT LSLSPGERAT LSCRASQSVN SNLNWYQQKP GQAPRLLIYH GSNRATGIPA  60
RFSGSGSGTD FTLTISSLEP EDFAVYYCQQ FDYFKEHNTF GQGTKVEIK             109

SEQ ID NO: 50          moltype = AA  length = 109
FEATURE                Location/Qualifiers
REGION                 1..109
                       note = AB72 VL
source                 1..109
                       mol_type = protein
                       organism = synthetic construct
```

-continued

```
SEQUENCE: 50
EIVKTQSPAT LSLSPGERAT LSCRASQSVN SNLNWYQQKP GQAPRLLIYH STNRPRGIPA  60
RFSGSGSGTD FTLTISSLEP EDFAVYYCQQ FDYFKEYNTF GQGTKVEIK             109

SEQ ID NO: 51          moltype = AA  length = 109
FEATURE                Location/Qualifiers
REGION                 1..109
                       note = AB73 VL
source                 1..109
                       mol_type = protein
                       organism = synthetic construct
SEQUENCE: 51
EIVLTQSPAT LSLSPGERAT LSCRASQSVN SNLNWYQQKP GQAPRLLIYH SNNRPHGIPA  60
RFSGSGSGTD FTLTISSLEP EDFAVYYCQQ FDYFREYNTF GQGTKVEIK             109

SEQ ID NO: 52          moltype = AA  length = 215
FEATURE                Location/Qualifiers
REGION                 1..215
                       note = B12 LC
source                 1..215
                       mol_type = protein
                       organism = synthetic construct
SEQUENCE: 52
EIVLTQSPGT LSLSPGERAT FSCRSSHSIR SRRVAWYQHK PGQAPRLVIH GVSNRASGIS  60
DRFSGSGSGT DFTLTITRVE PEDFALYYCQ VYGASSYTFG QGTKLERKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                            215

SEQ ID NO: 53          moltype = AA  length = 457
FEATURE                Location/Qualifiers
REGION                 1..457
                       note = B12 HC
source                 1..457
                       mol_type = protein
                       organism = synthetic construct
SEQUENCE: 53
QVQLVQSGAE VKKPGASVKV SCQASGYRFS NFVIHWVRQA PGQRFEWMGW INPYNGNKEF  60
SAKFQDRVTF TADTSANTAY MELRSLRSAD TAVYYCARVG PYSWDDSPQD NYYMDVWGKG  120
TTVIVSSAST KGPSVFPLAP SSKSTSGGTA ALGCLVKDYF PEPVTVSWNS GALTSGVHTF  180
PAVLQSSGLY SLSSVVTVPS SSLGTQTYIC NVNHKPSNTK VDKKVEPKSC DKTHTCPPCP  240
APELLGGPSV FLFPPKPKDT LMISRTPEVT CVVVDVSHED PEVKFNWYVD GVEVHNAKTK  300
PREEQYNSTY RVVSVLTVLH QDWLNGKEYK CKVSNKALPA PIEKTISKAK GQPREPQVYT  360
LPPSRDELTK NQVSLTCLVK GFYPSDIAVE WESNGQPENN YKTTPPVLDS DGSFFLYSKL  420
TVDKSRWQQG NVFSCSVMHE ALHNHYTQKS LSLSPGK                           457

SEQ ID NO: 54          moltype = AA  length = 4
FEATURE                Location/Qualifiers
REGION                 1..4
                       note = Artificial Sequence
source                 1..4
                       mol_type = protein
                       organism = synthetic construct
SEQUENCE: 54
GGFG                                                              4
```

The invention claimed is:

1. An antibody-conjugate according to general structure (1):

$$AB\text{-}[(L^6)_b\text{-}\{Z\text{-}L\text{-}D\}_x]_y, \quad (1)$$

wherein:

AB is an anti-CEA antibody comprising a light chain and a heavy chain comprising the amino acid sequences set forth in SEQ ID NO: 38 and 36, respectively;

$L^6$ is -GlcNAc(Fuc)$_w$-S—;

S is GalNAc;

GlcNAc is N-acetylglucosamine;

Fuc is fucose;

w is 0 or 1;

b is 0 or 1;

x is 1 or 2;

y is 1, 2, 3 or 4;

-Z-L-D is:

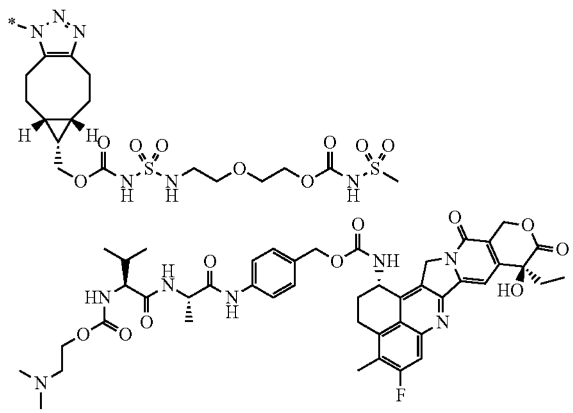

-continued
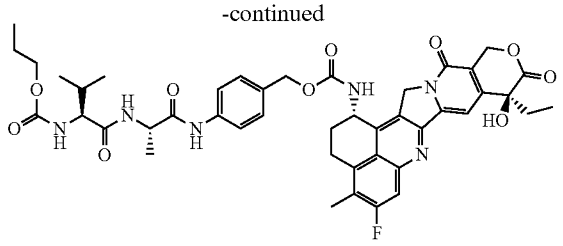
wherein * is the point of attachment of -Z-L-D to $L^6$, or a pharmaceutically acceptable salt thereof.
2. The antibody-conjugate according to claim 1, wherein x is 1.
3. The antibody-conjugate according to claim 1, wherein y is 2.
4. The antibody-conjugate of claim 1, wherein said antibody-conjugate is of the following formula:

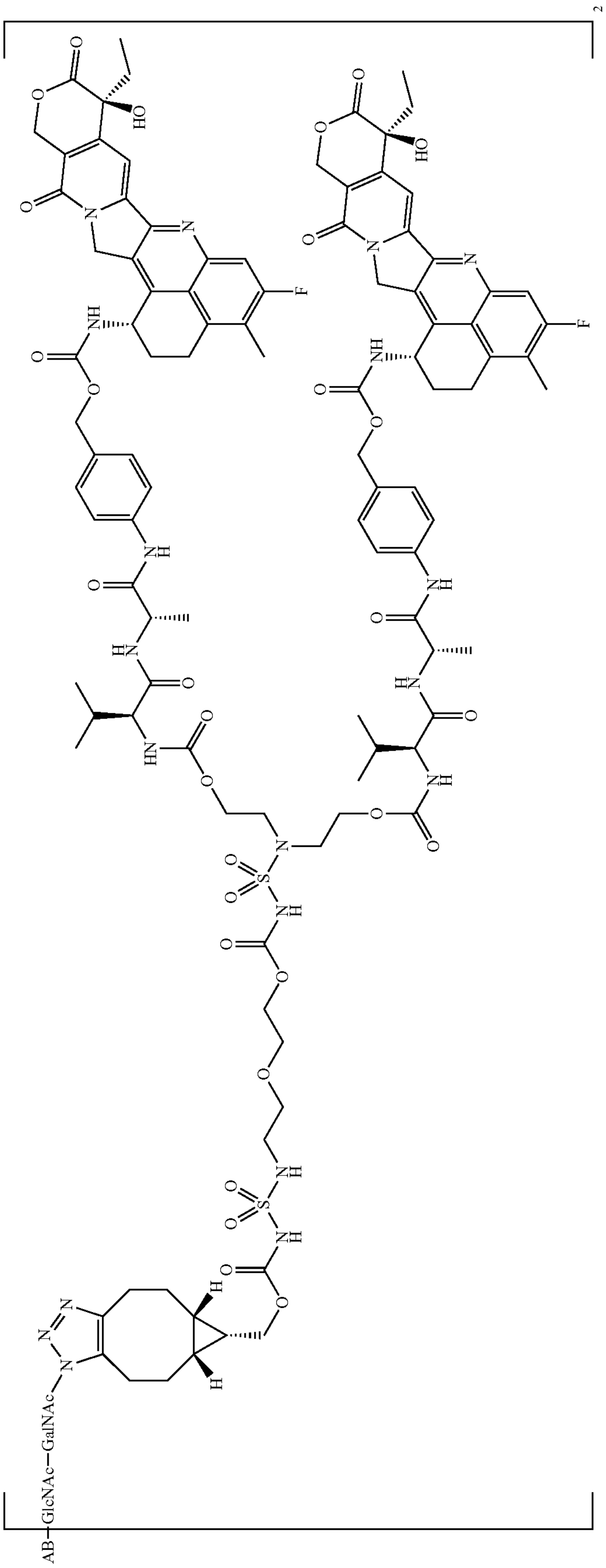

or a pharmaceutically acceptable salt thereof.

5. The antibody-conjugate of claim 1, wherein said antibody-conjugate is of the following formula:

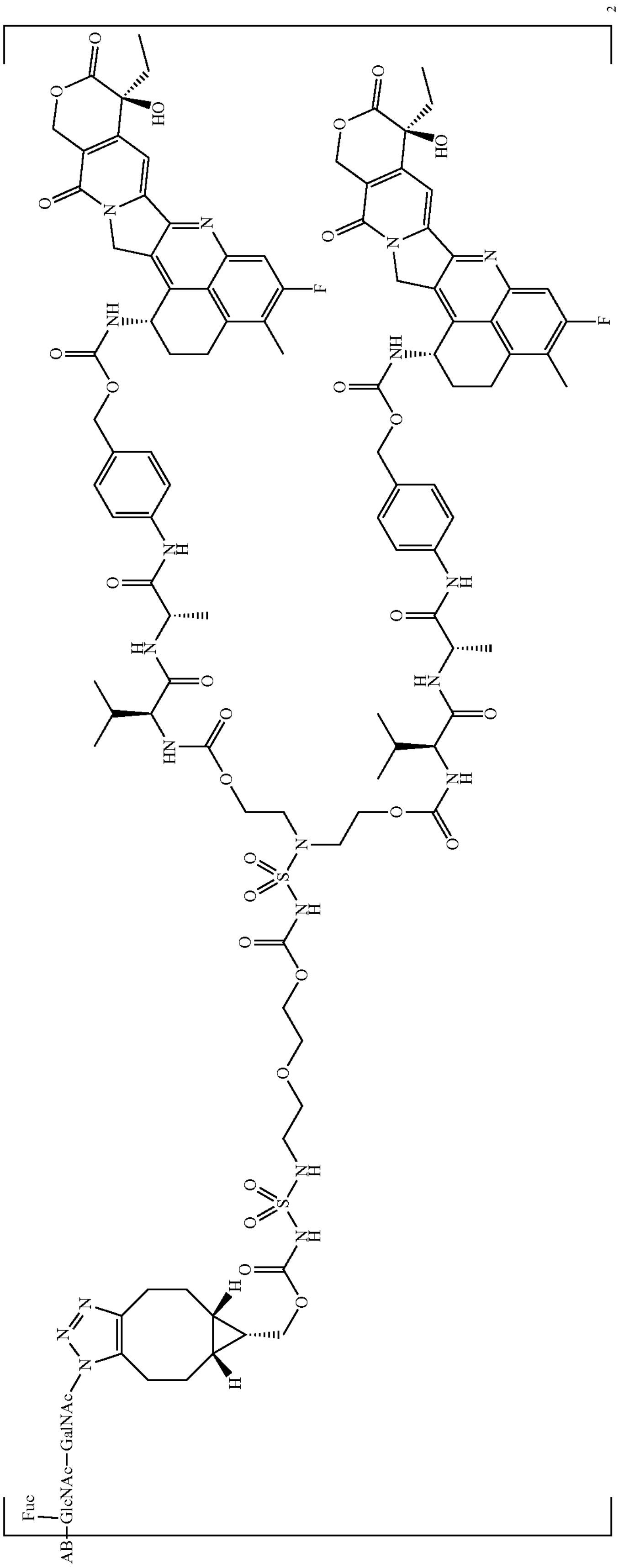

or a pharmaceutically acceptable salt thereof.

6. The antibody-conjugate according to claim 1, wherein w is 0.

7. The antibody-conjugate according to claim 1, wherein w is 1.

* * * * *